United States Patent
Belotserkovsky et al.

(10) Patent No.: US 10,807,093 B2
(45) Date of Patent: Oct. 20, 2020

(54) MICROFLUIDIC SYSTEMS

(71) Applicant: KATHOLIEKE UNIVERSITEIT LEUVEN, Leuven (BE)

(72) Inventors: Jaroslav Belotserkovsky, Oud-Heverlee (BE); Francesco Dal Dosso, Leuven (BE); Tadej Kokalj, Trzin (SI); Jeroen Lammertyn, Neerijse (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 207 days.

(21) Appl. No.: 16/055,698

(22) Filed: Aug. 6, 2018

(65) Prior Publication Data
US 2018/0345288 A1     Dec. 6, 2018

Related U.S. Application Data

(63) Continuation-in-part of application No. PCT/EP2017/052572, filed on Feb. 6, 2017.

(30) Foreign Application Priority Data

Feb. 5, 2016 (GB) .................................. 1602106.5
May 18, 2016 (GB) .................................. 1608772.8
(Continued)

(51) Int. Cl.
*B01L 3/00*     (2006.01)
*F04B 19/00*     (2006.01)
(Continued)

(52) U.S. Cl.
CPC ....... *B01L 3/502792* (2013.01); *B01L 3/5023* (2013.01); *B01L 3/50273* (2013.01);
(Continued)

(58) Field of Classification Search
CPC ............. B01L 3/502792; B01L 3/5023; B01L 3/50273; B01L 3/00; B01L 3/50;
(Continued)

(56) References Cited

U.S. PATENT DOCUMENTS 4,320,758 A    3/1982   Eckenhoff et al.
5,522,769 A    6/1996   Deguiseppi
(Continued)

FOREIGN PATENT DOCUMENTS

CN     102278293 A    12/2011
CN     102418684 A     4/2012
(Continued)

OTHER PUBLICATIONS

Andersson et al., "Hydrophobic Valves of Plasma Deposited Octafluorocyclobutane in DRIE Channels," Sensors and Actuators B, vol. 75, 2001, pp. 136-141.
(Continued)

*Primary Examiner* — Brian J. Sines
(74) *Attorney, Agent, or Firm* — Workman Nydegger

(57) ABSTRACT

The present invention relates to a fluid conduit system and manufacture thereof, for the propulsion of fluids. The micro- or millifluidic system is useful within LOC, POC diagnostics digital ELISA, drug delivery applications or sampling. The system includes a capillary pump and a fluid conduit operationally connected to the pump, and a gas-permeable liquid-sealed unit with a vent hole gas-permeable to the outside. The fluid conduit includes a first conduit zone prefilled or pre-Tillable with a first volume of trigger liquid, upstream of the unit with the vent hole, a third conduit zone with a further volume, upstream of the capillary pump, and a second conduit zone pre-filled or pre-Tillable with a working liquid between the first and third conduit zones, connected to both, and directly connected to the first conduit (Continued)

zone. The first volume is proportionally larger than or equal to the volume of the third conduit zone.

20 Claims, 39 Drawing Sheets

(30) Foreign Application Priority Data

| Sep. 9, 2016 | (GB) | ................................. | 1615339.7 |
| Aug. 4, 2017 | (GB) | ................................. | 1712561.8 |
| Aug. 4, 2017 | (GB) | ................................. | 1712562.6 |
| Aug. 4, 2017 | (GB) | ................................. | 1712564.2 |
| Dec. 22, 2017 | (GB) | ................................. | 1721699.5 |

(51) Int. Cl.

| G01N 33/52 | (2006.01) |
| G01N 33/543 | (2006.01) |
| F04B 19/16 | (2006.01) |
| F04B 19/20 | (2006.01) |

(52) U.S. Cl.
CPC ............ *F04B 19/006* (2013.01); *F04B 19/16* (2013.01); *F04B 19/20* (2013.01); *G01N 33/523* (2013.01); *G01N 33/54333* (2013.01); *B01L 2200/0668* (2013.01); *B01L 2200/146* (2013.01); *B01L 2200/16* (2013.01); *B01L 2300/0819* (2013.01); *B01L 2300/14* (2013.01); *B01L 2400/043* (2013.01); *B01L 2400/0406* (2013.01); *B01L 2400/0688* (2013.01)

(58) Field of Classification Search
CPC ........ F04B 19/006; F04B 19/16; F04B 19/20; G01N 33/523; G01N 33/54333; G01N 1/00; G01N 1/22

See application file for complete search history.

(56) References Cited

U.S. PATENT DOCUMENTS

| 5,571,633 | A | 11/1996 | Hagiuda |
| 7,226,439 | B2 | 6/2007 | Prausnitz et al. |
| 9,447,781 | B2 | 9/2016 | Deem et al. |
| 2002/0036018 | A1 | 3/2002 | McNeely et al. |
| 2005/0232817 | A1 | 10/2005 | Ahn et al. |
| 2009/0189464 | A1 | 7/2009 | Schilffarth |
| 2009/0252629 | A1 | 10/2009 | Kwon et al. |
| 2011/0216953 | A1* | 9/2011 | Callahan ................. G06K 9/00 382/128 |
| 2012/0046644 | A1 | 2/2012 | Ziaie et al. |
| 2013/0090633 | A1 | 4/2013 | Loeb |
| 2013/0337576 | A1 | 12/2013 | Zhu et al. |
| 2018/0202903 | A1* | 7/2018 | Chou ..................... G01N 21/76 |
| 2018/0246089 | A1* | 8/2018 | Chou ....................... G01N 1/30 |

FOREIGN PATENT DOCUMENTS

| DE | 102015101106 A1 | 7/2016 |
| EP | 2902784 A1 | 8/2015 |
| GB | 2474888 A | 5/2011 |
| WO | 9702849 A1 | 1/1997 |
| WO | 2010041230 A2 | 4/2010 |
| WO | 2012013472 A1 | 2/2012 |
| WO | 2013189502 A1 | 12/2013 |
| WO | 2017134313 A1 | 8/2017 |

OTHER PUBLICATIONS

Au et al., "Microvalves and Micropumps for BioMEMS," Micromachines vol. 2, 2011, pp. 179-220.

Baidya et al., "Organic Solvent-Free Fabrication of Durable and Multifunctional Superhydrophobic Paper from Waterborne Fluorinated Cellulose Nanofiber Building Blocks," ACS Nano, vol. 11, 2017, pp. 11091-11099.

Ball et al., "A Simple Check Valve for Microfluidic Point of Care Diagnostics," Royal Society of Chemistry, Lab Chip, vol. 16, 2016, pp. 4436-4444.

Balu et al., "Design of Superhydrophobic Paper/Cellulose Surfaces via Plasma Enhanced Etching and Deposition," Contact Angle, Wettability and Adhesion, vol. 6, 2009, pp. 235-249.

Bashar et al., "Superhydrophobic Surfaces with Fluorinated Cellulose Nanofiber Assemblies for Oil-Water Separation," Royal Society of Chemistry, RSC Advances, vol. 7, 2017, pp. 37168-37174.

Begolo et al., "The Pumping Lid; Investigating Multi-Material 3D Printing for Equipment-Free, Programmable Generation of Positive and Negative Pressure for Microfluidic Applications," Royal Society of Chemistry, Lab Chip vol. 14, 2014, pp. 4616-4628.

Cate et al., "Recent Developments in Paper-Based Microfluidic Devices," Analytical Chemistry, vol. 87, 2015, pp. 19-41.

Cho et al., "How the Capillary Burst Microvalve Works," Journal of Collloid and Interface Science vol. 306, 2007, pp. 379-385.

Comina et al., "Autonomous Chemical Sensing Interface for Universal Cell Phone Readout," Angewandte Communications International, vol. 54, 2015, pp. 8708-8712.

Dosso et al., "Self-Powered Programmable Microfluidic Platform for LOC Applications," Biomedical Microdevices, vol. 20, No. 2, 2018, 2 Pages.

Dosso et al., "Creasensor: SIMPLE Technology for Creatinine Detection in Plasma," Analytica Chimica Ada vol. xxx, 2017, 8 Pages.

Feng et al., "Passive Valves Based on Hydrophobic Microfluidics," Sensors and Actuators A, vol. 108, 2003, pp. 138-143.

Gerbers et al., "A New Paper-Based Platform Technology for Point-of-Care Diagnostics," Royal Society of Chemistry, Lab Chip, vol. 14, 2014, pp. 4042-4049.

Gervais et al., "Toward One-Step Point-of-Care Immunodiagnostics Using Capillary-Driven Microfluidics and PDMS Substrates," The Royal Society of Chemistry, Lab Chip, vol. 9, No. 23, Dec. 7, 2009, pp. 3330-3337.

Gervais et al., "Microfluidic Chips for Point-of-Care Immunodiagnostics," Advanced Healthcare Materials, vol. 23, 2011, H151-H176.

Hitzbleck et al., "Reagents in Microfluidics: an 'in' and 'out' Challenge," The Royal Society of Chemistry, Chem Soc Rev, vol. 42, 2013, pp. 8494-8516.

Hu et al., "Water Resistance Improvement of Paper by Superhydrophobic modification with Microsized CaCO3 and Fatty Acid Coating," Colloids and Surfaces A: Physicochem. Eng. Aspects, vol. 351, 2009, pp. 65-70.

Kokalj et al., "Self-Powered Imbibing Microfluidic Pump by Liquid Encapsulation: Simple," Royal Society of Chemistry, Lab Chip, vol. 14, 2014, pp. 4329-4333.

Lau et al., "Dynamics of Microvalve Operations in Integrated Microfluidics," Micromachines vol. 5, 2014, pp. 50-65.

Li et al., "A Capillary-Pressure-Based Air Pump for Nanoliter Liquid Handling in Microfluidic Devices," 15th International Conference on Miniaturized Systems for Chemistry and Life Sciences, Oct. 2-6, 2011, pp. 918-920.

Melin et al., "Microfluidic Large-Scale Integration: The Evolution of Design Rules for Biological Automation," Microfluidic LSI Design, Annual Review of Biophysics & Biomolecular Structure, vol. 36, 2007, pp. 213-231.

Mohammed et al., "Lab-on-a-Chip or Chip-in-a-Lab: Challenges of Commercialization Lost in Translation," Procedia Technology, vol. 20, 2015, pp. 54-59.

Novo et al., "Control of Sequential Fluid Delivery in a Fully Autonomous Capillary Microfluidic Device," RSC Publishing, Lab Chip, vol. 13, 2013, pp. 641-645.

Novo et al., "Integrated Optical Detection of Autonomous Capillary Microfluidic Immunoassays:a Hand-Held Point-of-Care Prototype," Biosensors and Bioelectronics, vol. 57, 2014, pp. 284-291.

Oh et al., "A Review of Microvalves," Journal of Micromechanics and Microengineering, vol. 16, May 2006, pp. R13-R39.

(56) References Cited

OTHER PUBLICATIONS

Qin et al., "Self-Powered Microfluidic Chips for Multiplexed Protein Assays from Whole Blood," NIH Public Access, Lab Chip, vol. 9, No. 14, Jul. 21, 2009, 11 Pages.
Qiu et al., "Finger-Actuated, Self-Contained Immunoassay Cassettes," Biomed Microdevices, vol. 11, 2009, pp. 1175-1186.
Riegger et al., "Dye-Based Coatings for Hydrophobic Valves and their Application to Polymer Labs-on-a-Chip," Journal of Micromechanics and Microengineering, vol. 20, 2010, 7 Pages.
Safavieh et al., "Capillaries: Pre-Programmed, Self-Powered Microfluidic Circuits Built form Capillary Elements, " RSC Publishing, Lab Chip, vol. 13, No. 21, 2013, pp. 4180-4189.
Samyn, "Wetting and Hydrophobic Modification of Cellulose Surfaces for Paper Applications," Journal of Materials Science, vol. 48, 2013, pp. 6455-6498.
Song et al., "Approaching Super-Hydrophobicity from Cellulosic Materials: A Review," Paper Chemistry, Nordic Pulp & Paper Research Journal vol. 28, No. 2, 2013, pp. 216-238.
Srivastava et al., "Microfluidic Pressure Sensing Using Trapped Air Compression," NIH Public Access, Lab Chip, vol. 7, No. 5, May 2007, 10 Pages.
Volpatti et al., "Commercialization of Microfluidic Devices," Trends in Biotechnology, vol. 32, No. 7, Jul. 2014, pp. 347-350.
Wang et al., "Paper Pump for Passive and Programmable Transport," Biomicrofluidics, vol. 7, 2013, 12 Pages.
Wang et al., "A Self-Powered, One-Step Chip for Rapid, Quantitative and Multiplexed Detection of Proteins from Pinpricks of Whole blood," The Royal Society of Chemistry, Lab Chip, vol. 10, 2010, pp. 3157-3162.
Yang et al. "Fabrication of a Hydrophilic Poly(dimethylsiloxane) Microporous Structure and Its Application to Portable Microfluidic Pump," Japanese Journal of Applied Physics, vol. 49, 2010, 4 Pages.
Yuen et al., "Low-Cost Rapid Prototyping of Flexible Microfluidic Devices Using a Desktop Digital Craft Cutter," The Royal Society of Chemistry, Lab Chip, vol. 10, 2010, pp. 384-387.
Zhang et al., "Micropumps, Microvalves, and Micromixers Within PCR Microfluidic Chips: Advances and Trends," Biotechnology Advances, vol. 25, 2007, pp. 483-514.
Zimmermann et al., "Capillary Pumps for Autonomous Capillary Systems," The Royal Society of Chemistry, Lab Chip, vol. 7, 2007, pp. 119-125.
Lo et al., "A Passive MEMS Drug Delivery Pump for Treatment of Ocular Diseases," Biomed Microdevices, vol. 11, Apr. 25, 2009, pp. 959-970.
International Search Report from PCT Application No. PCT/EP2017/052572, dated Jun. 19, 2017.
Great Britain Search Report from GB Application No. GB1602106.5, dated Aug. 5, 2016.
Great Britain Search Report from GB Application No. GB1712564.2, dated Feb. 1, 2018.
Great Britain Search Report from GB Application No. GB1712562.6, dated Jan. 31, 2018.
Great Britain Search Report from GB Application No. GB1712561.8, dated Feb. 9, 2018.
International Search Report from PCT Application No. PCT/EP2018/071271, dated Nov. 19, 2018.

\* cited by examiner

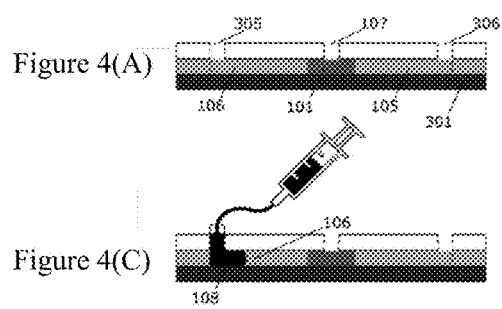
Figure 4(A)
Figure 4(C)
Figure 4(E)
Figure 4(G)
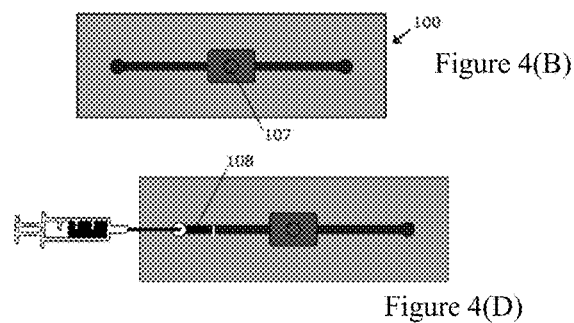
Figure 4(B)
Figure 4(D)
Figure 4(F)
Figure 4(H)
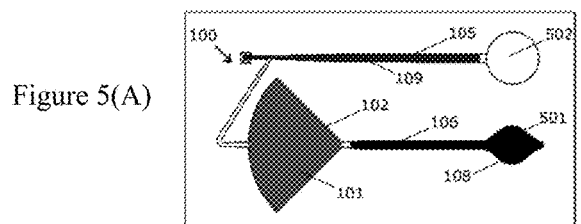
Figure 5(A)
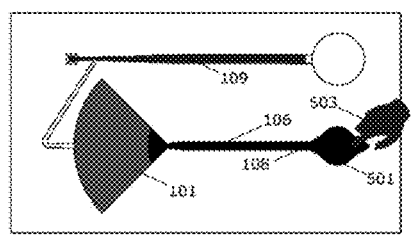
Figure 5(B)
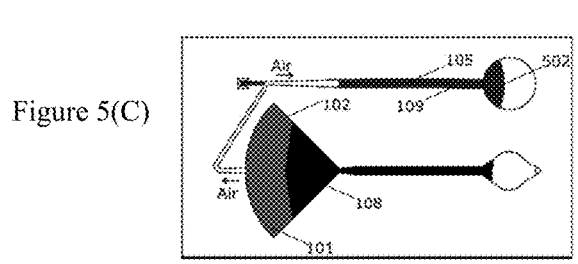
Figure 5(C)
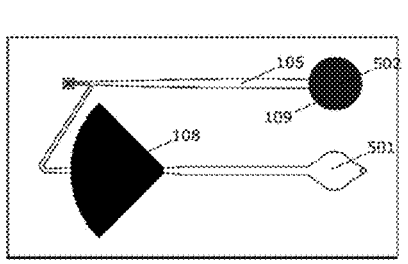
Figure 5(D)

|  | 0.404 mm | | 0.16 mm | |
|  | 26G | | 34G | |
|  | Pa | Bar | Pa | Bar |
| ΔP_0% | 0.5 | 4.8E-06 | 46.9 | 0.000 |
| ΔP_10% | 0.6 | 6.2E-06 | 61.2 | 0.001 |
| ΔP_20% | 0.8 | 8.4E-06 | 82.2 | 0.001 |
| ΔP_40% | 1.8 | 1.8E-05 | 173.7 | 0.002 |
| ΔP_60% | 5.1 | 5.1E-05 | 504.2 | 0.005 |
| ΔP_80% | 28.6 | 0.000 | 2805.6 | 0.028 |
| ΔP_90% | 104.1 | 0.001 | 10223.4 | 0.102 |
| ΔP_95% | 248.7 | 0.002 | 24414.8 | 0.244 |
| ΔP_100% | 670.5 | 0.007 | 65821.9 | 0.658 |

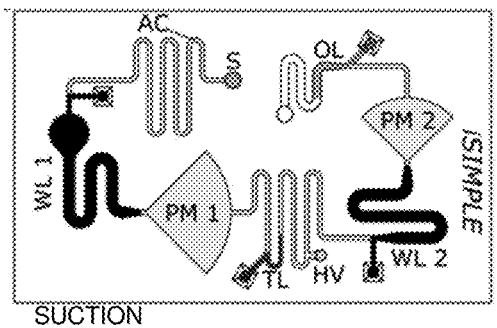
Figure 26(A)
Figure 26(B)
Figure 26(C)
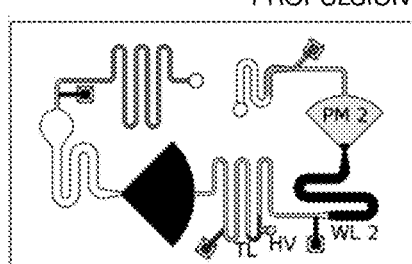
Figure 26(D)
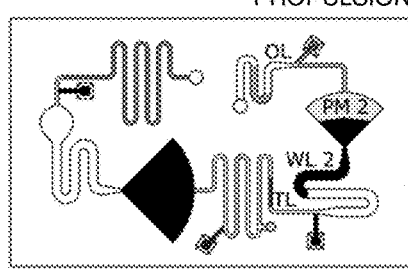
Figure 26(E)
Figure 26(F)

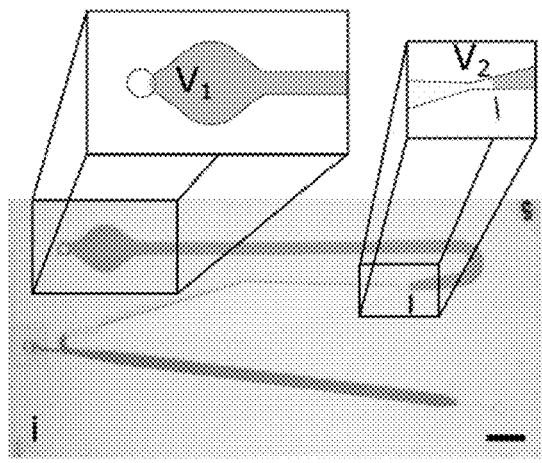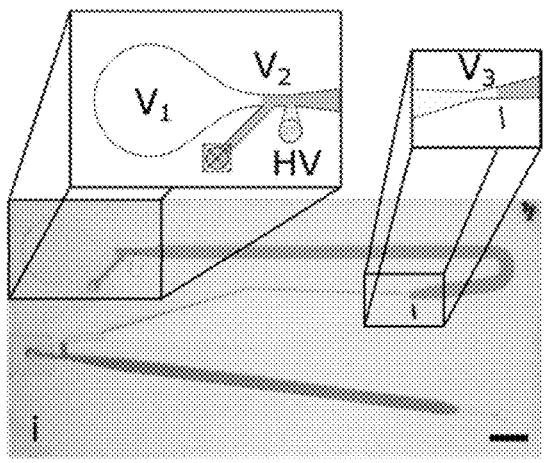
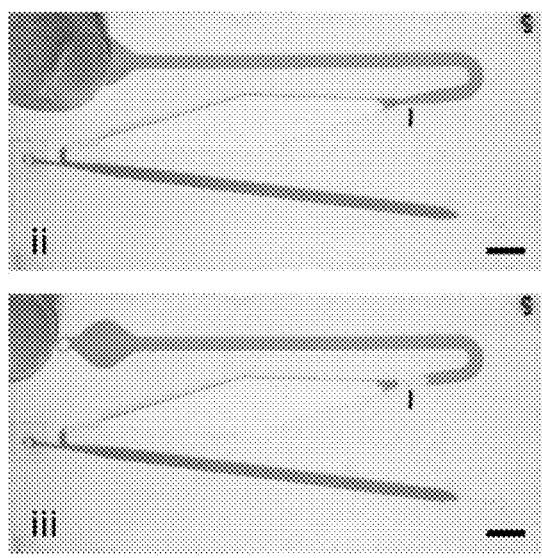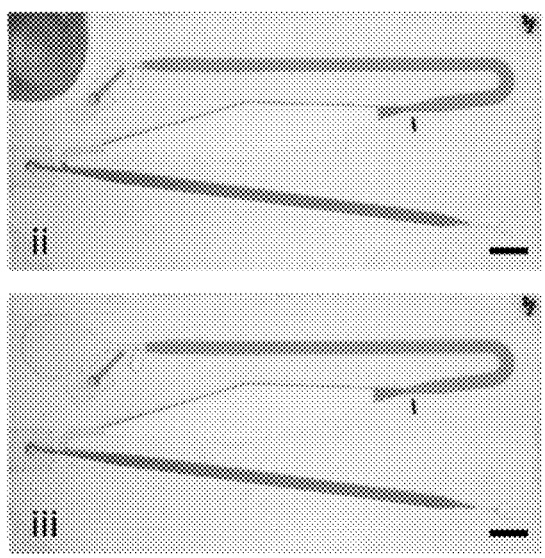
Figure 48(A)	Figure 48(B)

MICROFLUIDIC SYSTEMS

TECHNICAL FIELD

The present invention relates to a fluid conduit system, web or network to manipulate fluids with gas-permeable liquid-sealed unit(s) with and without vent, suitable for the propulsion of fluids as well as to the manufacturing and use of such pumps. The micro- or millifluidic system of the present invention are particularly useful within lab-on-a-chip, point-of-care diagnostics, digital ELISA and drug delivery applications or sampling.

BACKGROUND ART

The microfluidic field has witnessed over the past years a true outburst in developing portable and self-powered devices for point-of-care (POC) applications (Mohammed et al. Procedia Technol. 2015; Gervais et al. Adv. Mater. 2011) However, only few microfluidics platforms for POC applications, i.e. performed close to the patient without the need for a clinical lab, have been successfully commercialized to date (Alere, Quidel, Clearview, Clearblue) due to the number of challenges that arise when accommodating complex biological assays on relatively simple devices.

Miniaturization is one of the key aspects of lab-on-a-chip (LOC) devices as it enables limited sample and reagent consumption, reduced time-to-results, portability, and high parallelization and multiplexing. However, the majority of traditional LOC platforms still requires external large and relatively expensive pumping mechanisms to control the liquid flow, such as syringe pumps, electro-pneumatic or pressure-driven systems. This issue has been tackled already by various completely autonomous and self-powered pumping solutions. For instance, systems based on capillary forces of intricate microstructures are capable of drawing liquids into a microfluidic network and can perform complicated multi-step assays. These systems are fabricated using different substrates, such as silicon or polydimethylsiloxane (PDMS) but require hydrophilization of these materials to obtain the capillary effect. Other platforms are based on the so called "degas-driven flow" concept, which takes advantage of the inherent high porosity and air solubility of PDMS. The air is initially extracted from the PDMS in a vacuum chamber and only when brought back to the atmospheric conditions, it reabsorbs the air. When a liquid sample is loaded on the inlet port of a PDMS device, it is drawn into the microfluidic channel due to the lower pressure created inside the channel. However, this approach is limited to permeable materials while the control over flow rate and timing is challenging. Paper microfluidics is another approach in the LOC field, attracting large attention in recent years. Here, paper, or other porous materials such as textile, are exploited as pumping element relying on capillary action to move liquids. The paper strips are often patterned with different reagents at different locations with the final goal to perform multi-step tests. The most successful commercially available self-powered devices to date are the lateral flow strips which have been used to develop a wide variety of point-of-care (POC) tests, including HiV, influenza A/B, malaria, and hCG hormone testing. However, the transport of analytes and reagents in the paper matrix remains an important limitation since it decreases sensitivity and specificity of the tests, leading mainly to qualitative results. Recently, the focus has shifted to the development of quantitative or semi-quantitative tests which, however, require an external reader reducing their portability. In order to solve this issue, hybrid solutions have been presented, where paper as pumping element is combined with traditional continuous microfluidics (Kokalj, et al. Lab Chip. 2014; Wang, et al. Lab Chip. 2010). Here, analytes and reagents flow in microfluidic channels without getting in contact with the porous material of the self-powered low cost devices.

The presented self-powered LOC platforms are designed to pull the liquid inside the channel or matrix. Only a few solutions have been described in literature that show the ability to push the liquid through the channels or matrix. This concept drastically expands the number of microfluidic applications and the ability to manipulate liquids on-chip. For instance, such infusion pumping could allow also for drug delivery systems whereas the combination of infusion and suction systems would enable the LOC devices with complex and multistep protocols. Different mechanisms were proposed so far for infusion pumping: i) a pressurized gas generated by a chemical reaction that pushes the downstream liquid through the microfluidic channel (Qin, et al. Lab Chip. 2009); ii) sequential pressing on polyethylene pouches, injecting the reagents into the microfluidic network (Qiu, et al. Biomed Microdevices. 2009); iii) a PDMS micro sponge prefilled with liquid, squeezed on the device inlet releasing and injecting the liquid in the circuit (Yang et al. Jpn J Appl Phys. 2010); iv) a silicon tube, coupled to the inlet of a microfluidic device, where a check-valve prevents backward flow, is repeatedly compressed with the finger to infuse a preloaded sample in the system (Comina, et al. Angew Chem Int Ed Engl. 2015); v) a pumping lid, coupled to the inlet/outlet of a microfluidic chip, able to generate a controlled pressure, positive or negative, to infuse or withdraw fluids in a microfluidic device (Begolo, et al. Lab Chip. 2014). Additionally, vents or valves can be introduced in the LOC devices that allow gas venting or stop a flow (U.S. Pat. Nos. 5,522,769, 5,571,633).

One of the (many) field limitations is lack of reliable, easy to fabricate and inexpensive microfluidic components, such as micropumps and microfluidic valves. (Mohammed et al. Procedia Technol. 2015, Oh and Ahn. J. Micromech. Microeng 2006; Volpatti and Yetisen. Trends Biotechnol. 2014; Au, et al. Micromachines 2011). The eminent role of microfluidic valves, referred to herein also as microvalves, has been long acknowledged in the field (Oh and Ahn. J. Micromech. Microeng 2006; Au, et al. Micromachines 2011) These micro components enable delay or complete stopping of the fluid flow without the user intervention, which in turn enables all-important complex liquid manipulations on microfluidic devices. In general, microfluidic valves can be classified in two main categories: active and passive. field (Oh and Ahn. J. Micromech. Microeng 2006; Au, et al. Micromachines 2011; Castillo-Leon and Svendsen. Springer International Publishing, 2015; Zhang, et al. Biotechnol. Adv. 2007.) Active microvalves require external, often bulky equipment or power supply (i.e. pneumatic, magnetic, electric, piezoelectric or thermal actuation mechanisms). Although used in many different instances, (Oh and Ahn. J. Micromech. Microeng 2006; Au, et al. Micromachines 2011) these types of valves by large do not match the most rigorous requirements of microfluidic platforms intended for POC applications (Melin, et al. Annu. Rev. Biophys. Biomol. Struct. 2007) Here, the microfluidic valve should ideally present number of assets, both generic (compatibility with liquids and gases, pressure resistance, free of leakage) as well as those specific for the POC applications (ease of fabrication and use, portability and lack of need for any external power supply). Therefore, passive microvalves, which are independent from any external equipment for their activation and functioning, are fairly better candidates for POC. Passive microvalves can be subdivided into mechanical and non-mechanical subclass. The mechanical valves rely on moving parts such as flap, membrane, ball or other microfabricated elements for opening/closing of a specific microfluidic channel (Au, et al. Micromachines 2011; Comina, et al. Angew. Chem. Int. Ed. Engl. 2015; Lau, et al. Micromachines 2014; Ball, et al. Lab Chip 2016). As such, they are mostly used as check valve, allowing the flow only in one direction, similarly to a diode in an electrical circuit. Despite their wide usage, they do, however, present number of shortcomings: i) need for high precision and costly fabrication, ii) often poor robustness due to possible failure of moving parts and iii) incompatibility with different channel-based system (Au, et al. Micromachines 2011). The other subclass of passive valves does not rely on any mechanical parts, but rather on either the specific design or the surface modification of micro channels (Safavieh and Juncker. Lab Chip 2013; Novo, et al. Lab Chip 2013; Gervais and Delamarche. Lab Chip 2009) For instance, burst passive microvalves are based on the increased capillary resistance of a specific region of the microchannel obtained through an abrupt expansion of the channel dimensions (Cho, et al. J. Colloid Interface Sci. 2007; Feng, et al. Sensors Actuators A Phys. 2003; Novo, et al. Biosens. Bioelectron. 2014) In hydrophobic valves, based on surface modification, the flow is blocked due to a hydrophobic region patterned on the channel walls (trough plasma activation or coating with hydrophobic solution) (Riegger, et al. J. Micromechanics Microengineering 2010; Andersson, et al. Sensors Actuators B Chem. 2001). Medical diagnostics at the point-of-care (POC), can greatly improve access to medical diagnosis. Some POC requirements differ from those of traditional laboratory analysis: i) small and portable devices are preferred over bulky and expensive equipment, ii) fast TTR (i.e. 30 min) are required, iii) low volume of sample and reagents are preferred, and iii) the analysis does not require highly specialized technicians. Suction pump POC diagnostics have been around for many years, such as pregnancy tests and glucose monitors for diabetics, and have been a great improvement for patients. Thanks to the high success of these suction pump tests, there is a strong drive to develop advanced chips for other relevant applications. An example is the I-stat device that automates and miniaturizes advanced diagnostics currently performed in laboratories for several biomarkers such as blood gases, acid-base concentration, lactate concentration, and other blood variables. The requirements for a POC device set by the World Health Organization (WHO) are so called ASSURED, which stands for: affordable, specific, sensitive, user-friendly, robust and rapid, equipment free—self powered and disposable. These tests are of great importance in environments where timing is critical, laboratory facilities are limited or resources are low, such as in developing countries.

POC devices must ensure high sensitivity and specificity, regardless their intrinsic simplicity, portability and affordability. For certain applications, it is important that the target of interest (TOI) can be detected at very low concentrations and in complex matrices, such as blood or urine. The high sensitivity and specificity in a diagnostic test can be achieved through different methods, but the digital assay concept has proven to be one of the most sensitive and specific of all. In particular, this approach enables the detection of single molecules in ultra-small reaction wells by labelling them with enzyme reporters in a sandwich-type immunoassay. Nevertheless, LOC devices have still some drawbacks for certain applications where external pumping mechanisms, like syringe pumps, make the device actuation complex and expensive. These external and bulky pumping systems should be avoided, certainly for POC applications, and that is why recently attention on self-powered pump systems has increased. As earlier mentioned, paper based microfluidics could be a platform for self-powered microfluidic devices since it transports liquids using capillary forces without the assistance of external forces. This makes such systems cheap and disposable, however, it has some shortcomings when a complex bioassay needs to be implemented. First only one liquid can be flown over, this means that assays requiring multiple steps of liquid flow, e.g. sample-washing-secondary Ab, are diffult to achieve. Also, the flow rate of the liquid is fixed and depends on the type of paper that is used. Many microfluidic platforms, where the sample in transported through very narrow channels, suffer from complicated and expensive fabrication and limited sample manipulation steps. Several other passive pumping methods have been presented and investigated: i) a gravitational pump through gravitational forces, ii) the thermoviscous expansion of a fluid combined with a temperature-dependent viscosity creates net fluid flow at the microscale controlled by external heating, iii) the evaporation of a liquid can induce a concentration difference as the driving force for an evaporative pump, iv) the surface tension present in small droplets and the channel geometry can generate a certain flowrate, and recently v) via osmosis.

For bioassay, POC and LOC can also be implemented. As of today, three different main approaches have been used to achieve seeding of microbeads in microwell array to perform digital bioassay. EWOD (electrowetting on dielectric) platform can manipulate droplets in a precise a programmable way and it was used to seed microbeads in a HIH microwell array shuttling back and forth the droplet with beads over the array multiple times and achieving almost 100% with the help of a magnet positioned below the array. However, the EWOD platform requires large equipment, power supply and trained personnel increasing the cost, the complexity and reducing the portability and the user-friendliness. Alternatively, the shuttling of a droplet over the array can be achieved manually, moving the droplet with the help of for example a pipette tip. However, this approach is subjected to user to user variations, low reproducibility, needs expertise and training and is not automated. Both EWOD and manual protocols need a super hydrophobic surface to be able to move the droplet easily over the array. This surface is normally achieved with a layer of Teflon. However, the fabrication of Teflon coated array is complicated and expensive. A third approach is using channel-based microfluidics. Here a suction element (syringe pump) is used to pull a flow of beads over the array and let them sediment by gravity on top of the array to achieve seeding. The drawbacks are the need of an external pumping system such as syringe or pressure pumps and the low seeding efficiency achieved (around (40-50%)

So current digital assay platform rely on expensive, not user-friendly and power-dependent microfluidic platforms for liquid manipulation which are not compatible with POC application, low cost production, robustness and user-friendliness. Thus, there still is need for methods for seeding beads that are compatible with POC application, low cost production, robustness and user-friendliness.

Furthermore, there is a need in the art for self-powered delivery systems for delivering bioactive molecules to a human or animal patient. Such systems have a particular advantage that they can be activated by a simple push, for instance by the person carrying said delivery system.

The fluidic delivery systems of the art, such as those used for delivery or injection of drugs, vaccines or other medicinal products through the skin barrier are typically mechanically powered syringe systems. Such systems typically are not designed to deliver small volumes, below 100 μL, and to do so at controlled, predetermined flow rates. Further the precise control of flow rates during infusion or injection of fluids into biological tissue through a narrow opening such as a microneedle, or microneedle array is necessary.

Actuators in the art must be powered externally, e.g. electrically, magnetically, mechanically or by gas pressure systems. In the case of electrical, these require batteries and electric motors or response elements, adding to complexity, cost and requiring special disposing procedures (batteries, electrical components). Further, such electrical systems (including electrostatic, electrochemical, piezo-electric) are not desirable in implantable devices due to issues with biocompatibility and biodegradability. In the case of magnetic, there is a need for external fields and lack of precise control of the actuation force. In the case of mechanical and gas pressure, these have limited control over flow rates, volumes and pressures that can be generated for fluidic actuation. For example, Lo et al., describe a microfluidic drug delivery device actuated by externally applied, finger actuated mechanical force, and including a PDMS check-valve for control of fluidic flow rate. The flow rate varied from 0.61 μl/s for 250 mmHg (33.33 kPa) of applied pressure to 1.57 μl/s for 500 mmHg (66.66 kPa) (A passive MEMS drug delivery pump for treatment of ocular diseases. Biomed Microdev, 11 (2009), pp. 959-970). This clearly presents a limitation in applications that require continuous and more precisely controlled flow rates. Furthermore, most mechanical actuation systems rely on moving components, such as valves and pumping diaphragms. This complicates their fabrication, adding to system complexity and cost and increases a risk for breakdown. In addition, the presence of moving parts precludes or greatly complicates the fabrication of actively actuated infusion systems that can be applied as an adhesive patch. Adhesive patches are commonly used for transdermal drug delivery, however, these systems are based on passive diffusion of pharmaceutical substances across the skin barrier. As such, it is of interest to provide for active drug delivery systems that can be applied as self-powered adhesive patches.

U.S. Pat. No. 7,226,439 discloses a microneedle drug delivery device for transdermal delivery of drugs or other fluid. U.S. Pat. No. 4,320,758A discloses an osmotic microfluidic pump that is capable of actuation of fluids in infusion mode at a controlled rate. However, the invention disclosed in U.S. Pat. No. 4,320,758 relies on externally applied liquid to drive the osmotic pump. This limits the use of the system to certain environments and applications, such as implantable devices. Further, such osmotically driven pumps typically are not capable of attaining high pressures necessary for injection or infusion of viscous liquids through a narrow opening, such as may be required for drugs delivered transdermally via small needles. Also, osmotically driven pumps have a narrow range of achievable flow rates. U.S. Pat. No. 9,447,781 provides for an osmotically driven pump for high pressures and controlled flow rates. However, this system is reliant on a spring and piston mechanism to actuate the fluid to be pumped. This complicates the design of the system, increasing its cost and limiting the types of materials that can be used for its fabrication. Further, this system is not capable of delivering fluids in a rapid fashion, being limited to flow rates of 1 μl/hour.

SUMMARY OF THE INVENTION

It is an object of the present invention to provide a flexible propulsion pump system for use in micro- or millifluidic systems. This objective is accomplished by a device according to embodiments of the present invention.

The present invention provides a fluid conduit device comprising
  a capillary pump, comprising a solid sorbent enclosed in an enclosure and having an inlet and an outlet,
  a fluid conduit operationally connected to the inlet of the capillary pump,
  a gas-permeable liquid-sealed unit with a vent hole wherein said unit is gas-permeable to the outside through the vent hole, the unit being engaged with the fluid conduit at a predetermined location;
  a gas-permeable liquid-sealed unit with a vent hole wherein said unit is gas-permeable to the outside through the vent hole, the unit being engaged with the fluid conducted at a predetermined location, and
  an actuator unit upstream of the fluid conduit.

The fluid conduit comprises at least three interconnected zones, the at least three interconnected zones comprise:
i) a first conduit zone pre-filled with a first volume of trigger liquid, upstream of the unit with the vent hole and downstream of the actuator unit,
ii) a third conduit zone with a further volume, upstream of the capillary pump, but downstream of the unit with the vent hole, and
iii) a second conduit zone pre-filled with a working liquid before actuation of the actuator unit, the second conduit zone being positioned downstream of the unit with the vent hole, between the first conduit zone and the third conduit zone and functionally connected to both, and directly connected to the first conduit zone,
wherein the first volume is proportionally larger than or equal to the further volume of the third conduit zone. This way, by the volume of the further liquid in first conduit zone being proportionally larger than or equal to the further volume of the third zone, the pre-filled liquid in the second conduit zone can contact the solid sorbent of the capillary pump when the flux of the predetermined first volume of trigger liquid in the first conduit zone over the predetermined location of the unit with the vent hole corresponds to the movement of the same volume of working liquid through the third conduit zone (with a smaller volume than the first conduit zone) towards the capillary pump. Directly connected to the first conduit zone may mean that there is no further conduit zone between the second conduit zone and the first conduit zone. In some embodiments this may be referred to as there being no gap between the first conduit zone and the second conduit zone.

Where reference is made to trigger liquid and working liquid this does not refer to the fact that such liquids are different. Rather trigger liquid is used to refer to the liquid initially (after filling) present in the first conduit zone and working liquid is used to refer to the liquid initially (after filling) present in the second conduit. Thus the difference between trigger liquid and working liquid is rather determined by their spatial position and by their function thus performed.

The above device allows a reliable contact between the pre-filled liquid and the capillary pump, where only a first actuation with a small pressure is needed, the rest of the pumping being ensured by the capillary pump and the fluid, e.g. a gas such as air, provided into the conduit through the vent hole of the unit with the vent hole.

In some embodiments, the trigger liquid in the first conduit zone is of a same type as the working liquid. This advantageously allows filling the second conduit zone with working liquid and adding the trigger liquid in the first conduit zone, in a same step.

Alternatively, a predetermined volume of fluid, e.g. a gas such as air, is present at least between the working liquid (downstream of the unit with the vent hole) and the trigger liquid (upstream of the unit with the vent hole).

Potentially a predetermined volume of fluid, e.g. a gas such as air, may be present between the working liquid and the unit with the vent hole. This advantageously allows a reduction of the amount of pre-filled liquid needed. For example, the amount of pre-filled liquid added may not exceed the saturation of the capillary pump.

Further, a predetermined amount of fluid, e.g. a gas such as air, may be present between the trigger liquid and the unit with the vent hole. This allows a tunable delay between actuating the trigger liquid and the contact between the pre-filled liquid and the capillary pump.

In some embodiments, the pre-filling of the liquid in the second conduit zone may be done via an inlet port or the like.

In some embodiments, the first conduit zone may also be prefilled with a liquid. In some embodiments, the third conduit zone and/or the capillary pump is pre-filled with gas, or at least with a fluid with lower wettability than the liquid of the second conduit zone.

In some embodiments of the present invention, the device includes a barrier wherein the barrier comprises a gas-permeable liquid-sealed material to allow gas to pass and to stop liquid flow. The barrier is provided in the fluid conduit between two interconnected zones. The zones may both be filled with fluid, upstream and downstream of the barrier. The zones may both be filled with liquids, and the barrier may physically separate these liquids while at the same time keeping the two sections of the device connected, e.g. functionally connected, e.g. so that a change of pressure in an interconnected zone produces a change of pressure in the other interconnected zone.

In some embodiments of the present invention, the barrier comprises a hydrophobic material containing cavities for gas passage, which may be the same or similar material as the solid sorbent further treated to give it hydrophobic properties, for instance a hydrophobic paper, thus obtaining a gas-permeable liquid-sealed solid sorbent.

In some embodiments of the present invention, the solid sorbent of the pump has cavities with pore diameter of a value between 0.1 to 35 µm. In some embodiments the solid sorbent may be liquid absorbent.

In some embodiments of the present invention, the device further comprising downstream of said capillary pump and connected thereto a fluid conduit output comprising microneedles.

In some embodiments of the present invention, the solid sorbent of the pump is shaped in a 10° to 150° circular sector. This advantageously provides continuous action. The sector may be more preferably a 50° to 70° circular sector so that the pump is adapted to pump 0.1 µl to 1000 µl volume, for example 100 µl to 300 µl liquid. The size of the paper also determines the amount of volume of liquid that can be absorbed, e.g. the amount that can be pumped. The cavity size of the solid sorbent (e.g. 0.1-35 µm, for example being the pore size of a solid sorbent such as paper) allows pumping at pressures of 50 to 100 kPa, for example 60 to 70 kPa, e.g. through the resistance of a biological tissue barrier, for instance a skin. The flow rate may be about 0.07 µl/min to 30 µl/min, for example 4 to 10 µl/min. The pressure may partly or mainly be determined by the type of paper used. The volume of the liquid pumped may partly or mainly be determined by the size of the paper. The shape of the paper may partly or mainly determine the flow rate.

In some embodiments of the present invention, the fluid conduit device comprises a network configuration of channels and/or fluid reservoirs and wherein pumps, fluid reservoirs, the at least one gas-permeable liquid-sealed unit with vent and optionally at least one gas-permeable liquid-sealed barrier unit are engaged in the conduit device, to mix different fluids, to sequentially deliver different fluids or to push fluids forward and back in a same conduit zone, for instance an analysis zone, reaction zone or zone enclosing a hydrophilic-in-hydrophobic (HIH) microtube or microwell grids array.

In some embodiments of the present invention, the fluid conduit device is a microfluidic device and the (capillary) pump comprises a solid sorbent containing cavities and being enclosed in an enclosure, the microfluidic device further comprising a sample delivery section for applying a liquid containing magnetic beads operationally connected to a detection zone with one or more recessed parts, and a magnet. The magnet is positioned in the proximity of the detection zone. The solid sorbent can be shaped as explained earlier, and may be adapted to provide a flow rate of about 4 to 10 µl/min so that when operational the beads are immobilized in the recessed part of the detection zone in one continuous flow. In some embodiments of the present invention, the magnet of the microfluidic device has a strength of about 1.3 T and is positioned about 1.5 to 2.5 mm below the recessed part.

In some embodiments, the bead concentration in the liquid is about $2*10^7$ to $10*10^7$ beads/ml.

In some embodiments of the present invention, a solid sorbent of the pump has cavities with pore diameter of a value between 0.1 to 35 µm to pump second fluid at pressures of 50 to 100 kPa, preferably 60 to 70 kPa, to move liquids with a viscosity in the range of $0.5*10^{-3}$ Pa*s to $75*10^{-3}$ Pa*s, preferably in the range of $0.9*10^{-3}$ Pa*s up to $60*10^{-3}$ Pa*s.

In some embodiments of the present invention, a chamber is included for receiving, or including, powder reagents. For example, the chamber may be placed downstream of the capillary pump. The device is adapted to mix powder reagents with pumped liquid by that solid sorbent of the pump.

In some embodiments of the present invention, the device is adapted to mix powder reagents with pumped liquid by that solid sorbent of the pump with cavities with pore diameter of a value between 0.1 to 35 µm to pump fluid in the chamber at pressures of 50 to 100 kPa, more preferable of 60 to 70 kPa.

In some embodiments of the present invention, the capillary pump is a propulsion pump comprising a solid sorbent enclosed in an enclosure, said solid sorbent containing cavities comprising a first fluid,
wherein said enclosure of the solid sorbent comprises a first opening through which said solid sorbent can be contacted with a liquid and a second opening connecting the enclosure to an outlet channel and wherein said propulsion pump is adapted for being activated by contacting said solid sorbent with a liquid via said first opening resulting in the absorption of at least part of said liquid by the solid sorbent;

whereby this absorption is associated with the expulsion of at least part of said first fluid from the cavities of said solid sorbent into said outlet channel, whereby the flow of said first fluid into the outlet channel allows for propulsing and/or compressing a second fluid contained in said outlet channel and/or in a channel or reservoir connected to said outlet channel.

In some embodiments, the pump is adapted to pump second fluid at pressures of 50 to 100 kPa, e.g. 60 to 70 kPa. For example, the pump can move liquids with a viscosity in the range of $0.5*10^{-3}$ Pa*s to $75*10^{-3}$ Pa*s, preferably in the range of $0.9*10^{-3}$ Pa*s up to $60*10^{-3}$ Pa*s.

In particular embodiments, the device further comprises a barrier, wherein the barrier comprises a hydrophobic material or patch (e.g. a gas-permeable liquid-sealed solid sorbent) to move gas and stop liquid and wherein the barrier is engaged with the fluid conduit through at least two interconnected zones partially filled with fluid upstream and downstream of the barrier and wherein the gas-permeable solid sorbent comprises an hydrophobic material containing cavities for gas passage, for instance an hydrophobic paper.

In some embodiments, the capillary pump is a pulling pump, comprising a solid sorbent enclosed in an enclosure, said solid sorbent containing cavities comprising a first fluid, wherein the enclosure is connected downstream to a conduit open to the ambient, e.g. air.

In some embodiments, the enclosure of the solid sorbent includes vent-holes to expel the displaced first fluid (e.g. air) in the solid sorbent of the pulling pump.

Moreover, the first conduit zone is connected at its upstream side to, e.g. a fourth conduit zone further connected to an inlet for providing a sample, e.g. a liquid sample. When the pump is activated, the sample is pulled into the conduit by the pump.

The pulling pump pulls the sample until the liquid of the first conduit zone passes the unit with the vent hole, e.g. when the moving liquid being in contact with the unit with the vent hole stops being in contact thereto, in other words when the back end of the liquid passes the unit with the vent hole. Afterwards, the pump will pull air from the vent and the liquid sample will not be pulled. The pulling action and volume pulled can be predetermined by selecting the position of the vent along the channel.

Depending on whether the capillary pump is a propulsion pump or a pulling pump, the capillary pump can be connected to another conduit downstream or to a vent-hole (e.g. a vent-hole in the enclosure of the solid sorbent), respectively.

In some embodiments of the present invention, a fluid conduit output with microneedles is provided downstream of the capillary pump. The pump may be adapted to pump liquid at pressures of 50 to 100 kPa, e.g. 60 to 70 kPa, through the resistance of a biological tissue barrier, for instance a skin. For example, the pump may be adapted to pump a volume of liquid between 0.1 µl and 1000 µl. For example, the solid sorbent of the pump is shaped in a 10° to 150° circular sector, e.g. 50° to 70° circular sector as explained earlier.

In some embodiments of the present invention, the device can be actuated manually, e.g. by finger pressure, and operates with no additional energy consumption.

In some embodiments of the present invention, the device comprises at least a further capillary pump, the device being adapted to activate the capillary pump and the at least further capillary pump simultaneously, with exit in the same zone, for instance an analysis or reaction zone, of a conduit when operational to mix their fluid.

Alternatively, the device may be adapted to activate the capillary pump and the at least further capillary pump consequentially with exit in the same zone, for instance an analysis or reaction zone, of a conduit when operational to sequentially deliver their fluid to the same zone in said conduit.

In some embodiments including a further capillary pump, the further capillary pump may be activated by the first capillary pump.

In some embodiments, a plurality of capillary pumps are provided, which may be connected so that some are adapted to be activated simultaneously, while others may be activated sequentially, and yet at least one capillary pump of the plurality may be engaged to activate at least a different capillary pump.

In some embodiments of the present invention, the fluid conduit comprises a conduit shunt physically or functionally connected with a port for sampling fluid, for instance ambient fluid.

In some embodiments of the present invention, the fluid conduit comprises a conduit shunt physically or functionally connected with a reservoir for containing any one of the group consisting of a working fluid, an analyte, a ligand, a biological active molecule, a chemical reactive molecule and a physical reactive molecule.

In some embodiments of the present invention, the device comprises an enclosure of the solid sorbent comprising an opening connecting the enclosure to an outlet channel. Further, an analytical zone is in fluid connection to an outlet channel, the analytical zone being adapted for receiving an analyte, the analytical zone furthermore being provided with a detector unit for detecting properties of analyte in the analytical zone.

For example in some embodiments of the present invention, the device comprises a propulsion pump according to any of the previous claims, wherein an analytical zone is in fluid connection to the outlet channel, the analytical zone being adapted for receiving an analyte, the analytical zone furthermore being provided with a detector unit for detecting properties of analyte in the analytical zone.

In some embodiments, the propulsion pump system comprises one or more vents, e.g. units with vent holes, that are capable of introducing pressure variations within different zones of a microfluidic network in a controlled manner allow for decoupling different zones of a microfluidic network in order to design LOC devices with a more complex architecture (e.g. including a controlled actuation, including a delay in time between system activation and delivery of the fluid to an outlet in the system, allowing shuffling of fluids).

The present invention further provides a new microfluidic valving concept, based on a gas permeable-liquid impermeable porous material, that offers number of attractive features for POC applications, such as ease of fabrication, robustness, versatile functions and low fabrication cost. In some embodiments, the material may be a hydrophobic material, and to develop this hydrophobic material, we treated filter paper with a fluorinated compound and characterized it in terms of its hydrophobicity and burst pressure. Furthermore, to test its functionality as microfluidic valve, we have integrated it with our recently established SIMPLE platform (Self-powered Imbibing Microfluidic Pump by Liquid Encapsulation) and its infusion counterpart, namely iSIMPLE (Kokalj, et al. Lab Chip 2014; Dal Dosso, et al.

µTAS; Dublin, Ireland, 2016) We have opted for these two particular platforms because they can pull (SIMPLE) or push (iSIMPLE) liquids through microfluidic channels in completely autonomous fashion, while maintaining architectural simplicity, and as such pose number of challenges for the microfluidic valve integration. By combining these two technologies, we have developed additional functional features of these microfluidic platforms and enabled for the first time combination of the two pumping concepts in a single chip. The integration of the presented hydrophobic valve on the SIMPLE/iSIMPLE platform resulted in an ideal POC system which is self-powered, inexpensive, robust and can perform complex bioassay upon a single user activation. The present invention is not limited to hydrophobic materials, and the valving concept may utilize hydrophilic material and/or oleophobic or lipophobic material in a suitable system, e.g. and oil-based system as well.

Here, we present an innovative valve for channel-based microfluidics that fulfills the need for simple but robust and versatile microfluidic valves and as such can be combined with highly demanding point-of-care (POC) devices. The presented hydrophobic valve may include hydrophobic material simply made of porous material (e.g. filter paper) treated with a fluorinated compound (i.e. Aquapel) and shows both super-hydrophobic properties (contact angle up to 155°) as well as high resistance to liquid pressure (up to 9 kPa) while retaining gas permeability and utter fabrication simplicity. Whereas this valve can be integrated in any channel-based system and can be used both as a vent, forming a gas permeable liquid sealed unit with a vent, to delay for instance liquids displacement on chip, or as a barrier, to stop the liquid flow in a certain direction (e.g. the same type of hydrophobic material may be included in the unit with the vent and in the barrier), In this work we demonstrated some of its capacities by combining the barrier and valve concepts with our in house developed self-powered SIMPLE and iSIMPLE platforms. First, we integrated it with the infusion iSIMPLE pump, thus generating completely fail-proof activation regardless of how operator is actuating the system. Second, we used hydrophobic valves both as barrier and vent in the same microfluidic chip, which allowed the combination of two SIMPLE pumps for splitting one sample in two parallel channels. This attribute is fundamental for achieving multiplexing analysis on completely autonomous microfluidic platform. Finally, we achieved an unprecedented liquid manipulation for a self-powered microfluidic platform, namely shuttling of liquid, after a single user activation by combining for the first time SIMPLE and iSIMPLE with the developed hydrophobic vent (e.g. hydrophobic valve including vent) and barrier, all in a single chip. All these results convincingly demonstrated that developed hydrophobic valve combined with SIMPLE/iSIMPLE present essential building blocks for an ideal POC system, which is self-powered, inexpensive, robust and can perform complex bioassays upon a single user activation.

The present invention further solves the problems of the related art by providing a self-powered, low-cost system to deliver, inject, or infuse fluids through biological barriers such as skin, preferably in conjunction with needles or microneedles. In combination with hollow needles or microneedles, this microfluidic infusion pump is capable of self-powered delivery of liquids through skin or other biological tissue barriers with controlled flow rate and (high) pressures, for instance 50 to 100 kPa or 60 to 70 kPa. This system is capable of delivering small volumes of liquids, for instance volumes in the range 1-1000 µL and preferably in the range of 100 µl to 300 ^. In addition, in combination with a microneedle, this microfluidic infusion pump is capable of injecting liquids with different viscosities, for instance in the range of $0.5*10^{-3}$ Pa*s to $75*10^{-3}$ Pa*s and preferably in the range of $0.9*10^{-3}$ Pa*s up to $60*10^{-3}$ Pa*s.

A further advantageous aspect is also that such delivery system can in total or in part, and in particular the needles, be made of biocompatible material. As an example of biocompatible resin, polypropylene, polytetrafluoretheen (PTFE) (such as Teflon (registered trademark)) or polyurethane, as a single substance or a mixture of any of these substances, may be used. Stainless steels, gold, silver, platinum, titanium, nitinol, metal or any other conductive biocompatible materials can be used to fabricate the microneedles. Other parts of the delivery system may be biocompatible to the skin. The delivery may also in total or in part be made of a biodegradable material. For instance such biodegradable material as may be selected, for example, from among the following materials: polyglycolide (PGA), copolymers of glycolide, polylactides, copolymers of polylactide, unsymmetrically 3,6-substituted poly-1,4-dioxane-2,5 diones, poly-.-hydroxybutyrate (PHBA), PHBA/.-hydroxyvalerate copolymers (PHBA/HVA), poly-.-hydroxypropionate (PHPA), poly-p-dioxanone (PDS), poly-.-valerolactone, poly-.-caprolactone, methyl methacrylate-N-vinyl pyrrolidine copolymers, polyesteramides, polyesters of oxalic acid, polydihydropyrans, polyalkyl-2-cyanoacrylates, polyurethanes (PU), polyvinylalcohol (PVA), polypeptides, poly-.-malic acid (PMLA), poly-.-alkanoic acids, polyethyleneoxide (PEO) and chitine polymers. Copolymers of glycolide comprise, for example, glycolide/L-lactide copolymers (PGA/PLLA) and glycolide/trimethylene carbonate copolymers (PGA/TMC). Polylactides comprise, for example, poly-L-lactide (PLLA), poly-D-lactide (PDLA) and poly-DL-lactide (PDLLA). Copolymers of polylactide comprise, for example, L-lactide/DL-lactide copolymers, L-lactide/D-lactide copolymers, lactide/tetramethylglycolide copolymers, lactide/trimethylene carbonate copolymers, lactide/.-valerolactone copolymer, lactide/.-caprolactone copolymer, polydepsipeptides (glycine-DL-lactide copolymer), polylactide/polyethylene oxide copolymers, glycolide/L-lactide (PGA/PLLA)/polyethylene glycol (PEG) copolymers and polylactide/polyethylene glycol (PEG) copolymers.

In combination with a single microneedle or microneedle array, the delivery of medicinal products, drugs, vaccines or other fluids into or across the skin, can be accomplished in a pain-free, or almost pain-free manner to a human or animal subject.

In one aspect of the invention, the system is an infusion pump coupled an outlet connected to a single needle or microneedle, composed of metal, polymer of other appropriate material.

Another aspect of the invention is system is an infusion pump coupled an outlet connected to an array of microneedles, composed of metal, polymer or other appropriate material.

In still another aspect of the invention, the system is comprised of an integrated infusion pump and outlet, connected to needle(s), in the form of a flexible or depressible adhesive patch to be applied to skin of a human or animal subject.

In still another aspect of the invention, the system is an infusion pump connected to an outlet, wherein the infusion mechanism is started by a finger-press.

In still another aspect of the invention, the system is any number of infusion pumps connected to an outlet, and where the activation of the infusion mechanism is achieved by contact of a biological liquid, such as sweat or saliva, wherein the biological liquid serves as the working liquid for the infusion pump(s).

In still another aspect of the invention, the system is an infusion pump connected to an outlet in the form of a flexible or depressible adhesive patch, wherein the infusion mechanism is started by application of the patch to the subject's skin, such that the force of the application to the skin is sufficient to activate the infusion mechanism.

In still another aspect of the invention, the system is an infusion pump connected to an outlet connected to (micro) needle (array), and where the needle is initially retracted in the system, but through the action of the infusion pump, is forced into the subject's skin or another biological barrier such as a vein.

In still another aspect of the invention, the system is an infusion pump connected to an outlet, wherein the infusion pump is designed such that is allows to vary the flow rate of the fluid to be expelled from the outlet. An example of a flow rate achieved is 0.07-30 µL/min.

In still another aspect of the invention, the system is any number of infusion pumps connected to an outlet, such that the pumps may be activated simultaneously, and where the pumping rate or pressure of one pump may be different to the other. Further, such pumps may be connected by microfluidic channels that contain fluids or solid chemical compounds. Such an arrangement may be useful for mixing a number of fluids with other fluids or with solid chemical compounds pre-loaded in the connected microfluidic channels. Additionally, the different pumps may not be connected by a microfluidic network, but may be connected to outlets, thereby providing for a way to deliver more than one fluid, and at different flow rates or pressures but where the activation of the different pumps is simultaneous.

In still another aspect of the invention, the system is any number of infusion pumps connected to an outlet, such that the pumps may be activated sequentially, whereby one pump activates another pump, and where each pump is separated by a hydrophobic valve. Sequential pump activation may be useful to delay the time between system activation and delivery of the fluid to an outlet in the system.

In still another aspect of the invention, the system is any number of infusion pumps connected to an outlet, wherein the fluid to be delivered through the outlet is pre-loaded into the system, and is stored in the system until such time that the infusion pump(s) is activated to deliver the stored fluid through the outlet.

In still another aspect of the invention, the system is any number of infusion or propulsion pumps connected to an outlet, wherein the fluid to be delivered through the outlet is not part of the system, but is integrated into the system at such moment that the user of the system wishes to do so. An example of such is a container that contains the fluid to be delivered by the system, as a separate entity. The container (i.e. primary container) is then applied/inserted to the infusion system by the user, wherein the infusion system is designed such that the container may be integrated into the system, and at the moment of integration becomes connected to the microfluidic network in the system.

In still another aspect of the invention, the system is comprised of an infusion or propulsion pump (so called iSIMPLE) and a suction (so called SIMPLE) pump, whereby such system may be useful for simultaneous delivery of fluids through a biological barrier and into a biological tissue, and sampling of biological fluids within that same biological tissue. The suction pump(s) and consequently infusion pump may be connected by a microfluidic network to the same outlet, such that the delivery of fluids and sampling of fluids is achieved sequentially through the same or a different opening. Furthermore, the activation of the first infusion and second sampling through the same or another outlet may be activated by one actuation, whereby each one pump functions in succession of the other.

In still another aspect of the invention, the system is adapted for sequential or simultaneous delivery of fluids and sampling of fluids.

In still another aspect of the invention, the system is preloaded with fluid, or adapted to be loaded upon use.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

It is an object of the present invention to provide a flexible or depressible propulsion pump system for use in micro- or millifluidic systems, more particularly systems with millivolume or microvolume channels wherein the fluid is pro-pulsed by said the pump or is pulled by said pump. The propulsion pump system is connected to microneedles for delivery of fluid into a patient, more particular by intradermal delivery of volumes in the range 1-1000 µL and preferably in the range of 100 µl to 300 µl. We demonstrated that by such systems it is possible to reach injection pressures of for instance 50 to 100 kPa or 60 to 70 kPa.

This objective is accomplished by a device according to embodiments of the present invention.

In the microfluidic field, two crucial limitations prevent the affirmation of LOC and POC devices, both in academic and industrial world. Most of the microfluidic devices still need an external power source (i.e. syringe pump, electro mechanical systems, . . . ) that limits the portability and increases the complexity and price of the final device. On the other hand, the very large majority of the microfluidic platforms are able to handle the fluids only in withdraw mode, narrowing the panel of the possible microfluidic operations. The present invention is based on the finding that by guiding the fluids, typically gas, expulsed from a solid sorbent during the absorption of a liquid by said solid sorbent into a milli- or microfluidic channel, referred to as outlet channel, this fluid flow provides a propulsion force, which allows for pushing a fluid contained in said outlet channel and/or connected a milli- or microfluidic network over a predictable trajectory. Moreover, it was found that the expulsed fluid flow allowed for generating a pressure within said outlet channel and/or connected milli- or microfluidic network, which was higher or at least comparable to that of all the microfluidic pumps presented in literature. However, the propulsion pump system of the present invention has the important advantage over the pump systems of the prior art in that it can be made self-powered by incorporating the liquid needed for driving the absorption based propulsion pump system within the milli- or microfluidic system comprising the pump. It is clear that such propulsion pump systems may be particularly useful in many different milli- and microfluidic applications such as in Lab-on-Chip (LOC) or Point-of-Care (POC) diagnostic devices or in the, for instance intradermal, delivery of therapeutic compounds to a human or animal in need thereof.

Therefore, in a first aspect, the present invention provides a milli- or microfluidic propulsion pump, which comprises a solid sorbent enclosed in an enclosure, wherein said solid sorbent contains a first fluid prior to the activation of said pump. Typically, said enclosure of the solid sorbent comprises a first opening through which said solid sorbent can be contacted with a liquid and a second opening connecting the enclosure to an outlet channel. The propulsion pump according to the present invention is adapted for being activated by contacting said solid sorbent with a liquid via said first opening, resulting in the absorption of at least part of said liquid by the solid sorbent. This absorption is typically associated with the expulsion of at least part of said first fluid from the cavities in said solid sorbent into said outlet channel. The flow of said first fluid into the outlet channel allows for propulsing and/or compressing a second fluid contained in said outlet channel and/or in a microfluidic network connected to said outlet channel.

The propulsion pump according to embodiments of the present invention works in infusion mode, pushing with a predetermined flow rate. By tuning the shape and properties of parts of the propulsion pump, different flow rates can be achieved, based on the application requirements, and the flow rates can be defined as constant, decreasing or increasing flow rate. Parameters that can be tuned to achieve a predetermined flow rate are the geometrical shape of the enclosed sorbent material and/or its properties, such as pore size, pore distribution in the sorbent material, porosity and/or wetting properties; the inlet and/or outlet channel dimensions (diameter and/or length); the load upstream and/or downstream of the pump, e.g. the volume of working liquid and outlet liquid; the properties of the applied fluids (working liquid and/or active substance), such as, viscosity, compressibility and surface tension. The pump system of embodiments of the invention requires no external power and addresses the POC, LOC or drug delivery requirements. At the same time it is robust, easy to fabricate, inexpensive, easy to use, and suited for mass replication technologies. Moreover, the propulsion pump system of embodiments of the present invention allows to achieve predictable flows as well as high pressures. These properties allow to also use the propulsion pump of embodiments of the present invention for drug delivery applications, where a sufficient pressure is required to inject the drug through the skin into the body to overcome the skin barrier backpressure.

In particular embodiments of the present invention, the solid sorbent of the milli- or microfluidic propulsion pump may be any of a porous materials, wherein said cavities are interconnected pores; or a capillary material, wherein said cavities are capillaries, preferably open ended capillaries; or a mixed material or powder comprising both capillaries and pores.

In embodiments of the present invention, the first fluid may be a gas. Nevertheless, the skilled person understands that said first fluid may be a liquid in case the liquid being absorbed has a higher wetting affinity towards said solid sorbent than said first fluid.

In one embodiment said first opening of the enclosure of the solid sorbent of a milli- or microfluidic propulsion pump according to the present invention connects to an inlet channel suitable for bringing a liquid into contact with said solid sorbent through said first opening in order to activate said propulsion pump. In particular embodiments, said inlet channel contains a liquid and/or connects to a reservoir containing a liquid, the liquid being referred to as working liquid. Prior to the activation of the propulsion pump the working liquid is prevented from contacting said solid sorbent. Typically, the contact between said working liquid and the solid sorbent is prevented by the presence of a gas between the working liquid and the solid sorbent. The propulsion pump according to embodiments of the present invention may comprise an activation means or actuators for moving the working liquid in the inlet channel such that it contacts said solid sorbent via said first opening resulting in the absorption of at least part of the working liquid by said solid sorbent. In a particular embodiment this activation means or actuators comprises a flexible or depressible wall integrated in a wall of said inlet channel and/or reservoir, wherein said propulsion pump is adapted for being activated by applying a sufficient pressure on said flexible or depressible wall whereby the deformation of said pressed flexible or depressible wall acts on the working liquid in the inlet channel and/or reservoir such that the working liquid moves in the inlet channel and contacts said solid sorbent via said first opening resulting in the absorption of at least part of the working liquid by said solid sorbent.

In a particular embodiment of a propulsion pump according the first embodiment of the invention the inlet channel and/or reservoir containing said working liquid may be further connected to a micro- or millifluidic network. Upon activation of such propulsion pump the absorption of said working liquid from the inlet channel and/or reservoir by said solid sorbent exerts a suction force on the fluids contained in said connected micro- or millifluidic network. In certain embodiments said micro- or millifluidic network comprises a channel having an inlet opening wherein said suction force allows for pulling in a liquid positioned on said inlet opening into said channel. The availability of such channel having an inlet opening operably connected to a propulsion pump according to the present invention, which also generates a suction force is particularly useful in Lab-on-Chip (LOC) or Point-of-Care (POC) diagnostic devices or sampling devices as it allows to draw in an analyte sample into a micro- or millifluidic system.

Embodiments of the present invention provide a milli- or microfluidic propulsion pump wherein an analytical zone is in fluid connection to the outlet channel, the analytical zone being adapted for receiving an analyte. The analytical zone can be a channel, a chamber such as a reaction chamber, a compartment; any region that allows for some kind of fluid flow and then detection. The analytical zone is connected to a channel that allows the delivery of sample and reagents. The analytical zone is furthermore provided with a detector unit for detecting properties of analyte in the analytical zone. The detector unit may be any suitable type of detector unit, irrespective of the detection method e.g. any analytical sensor for detecting analytes in fluids, a colorimetric sensor, etc. The detector unit may be, but does not need to be, an optical detector. In particular embodiments, the detector unit may comprise a surface plasma resonance detector, for instance a gold surface plasma resonance detector or a fiber optic surface plasma resonance detector. The detector unit is a system for converting a biological signal into a quantifiable signal (electric, intensity, numbers). The detector unit may comprise a responsive element, responsive to an event; a processing element for generating a detection signal based on the response to the event; and a means for transmitting information between the responsive element and the processing element. The detector unit does not need to be present in the analytical zone, but in that zone an event, e.g. a reaction, must take place to generate a signal that is detectable. The detector unit can be present outside the analytical zone. The detector unit can be integrally connected to a propulsion pump according to embodiments of the present invention. If the detector unit is miniaturized and power (e.g. a battery) is provided, the detector unit can be attached/integrated to the chip comprising the propulsion pump. The connection between the detector unit and the propulsion pump can be via a channel, a pipe or a tube. Such channel, pipe, tube should be connected to the enclosure enclosing the solid sorbent without any fluid leakage.

Particular embodiments of the present invention provide a milli- or microfluidic propulsion pump wherein a unit, for instance a reaction chamber, is in fluid connection to the outlet channel, an analytical zone, for instance an analytical channel, being adapted for receiving reactive fluids. The unit is furthermore physically or functionally connected with a responsive element. The responsive element may comprise a fiber optic surface plasma resonance detector. The responsive element may be part of the body of the reaction chamber. The responsive element may be attached to the wall of the reaction chamber. Alternatively, the responsive element may be free of attachment to the reaction chamber. The responsive element may be sealed in the reaction chamber. The responsive element may be addressed by one or more electrodes located outside the reaction chamber. The responsive element may be addressed remotely. The transmitting means comprises one or both of electrical and optical elements. The said transmitting means may comprise one or both of mechanical and radiation elements. The radiation element provides radiation selected from the group consisting of acoustic waves, actinic radiation, nuclear radiation, and magnetism. The reaction chamber may further comprise one or more of reaction component(s), intermediate(s), and reaction product(s). The responsive element can be selected from the group consisting of thermocouples, interdigitated transducers (IDTs) and acoustic sensors (SAWs, QCMs). The responsive element can be an analytical sensor. The analytical sensor can monitor a physical property, a chemical property, a biological property. The analytical sensor can be disposable.

In another aspect, the present invention provides a milli- or microfluidic system comprising a propulsion pump according to embodiments of the first aspect of the present invention. In a particular embodiment said milli- or microfluidic system further comprises a suction pump. The suction pump may serve as an activation means or actuator for a propulsion pump according to embodiments of the first aspect of the present invention. In milli- or microfluidic systems according to this particular embodiment the inlet channel of the propulsion pump is typically operably connected to said suction pump such that following the activation of the suction pump a liquid can be moved into the inlet channel of said propulsion pump such that it contacts said solid sorbent via said first opening resulting in the absorption of at least part of the liquid by said solid sorbent and the expulsion of at least part of said first fluid from the solid sorbent into the outlet channel of the propulsion pump. The suction pump may comprise a further solid sorbent enclosed in a further enclosure. The further enclosure of said solid sorbent comprises one or more vent-holes and an opening connecting the further enclosure to a further inlet channel and/or to a further reservoir, which either or both contain a liquid, referred to as further working liquid. Said further inlet channel and/or further reservoir are operably connected to an inlet channel of a propulsion pump according to embodiments of the first aspect of the present invention. The suction pump is adapted for being activated by contacting said the further working liquid to the further solid sorbent of the suction pump, which results in the absorption of the further working liquid from said further reservoir and/or further inlet channel by this further solid sorbent. The pressure fall resulting from the absorption of the further working liquid from said further inlet channel and/or further reservoir generates a suction force on a liquid introduced or contained in the inlet channel of said propulsion pump such that said liquid is moved towards and brought into contact with said solid sorbent of the propulsion pump.

Milli- or microfluidic systems according to the second object of the invention may comprise two propulsion pumps according to embodiments of the first aspect of the present invention wherein a first propulsion pump can serve as an activation means or actuator for a second propulsion pump. Thereto, the outlet channel connected to the enclosure of the solid sorbent of said first propulsion pump connects with the reservoir and/or inlet channel containing a working liquid and being connected to the enclosure of the solid sorbent of said second propulsion pump. After activation of said first propulsion pump the fluid flow from the outlet channel of said first propulsion pump into said reservoir and/or inlet channel activates the second propulsion pump by pushing the working liquid contained therein towards and into contact with the enclosed solid sorbent of said second propulsion pump, resulting in the absorption of the working liquid by this sorbent and the expulsion of at least part of said first fluid from the solid sorbent into the outlet channel of the second propulsion pump.

More in detail, the system of the further aspect of the present invention may comprise a second propulsion pump including an inlet channel and a working liquid (or in contact to a reservoir with said working liquid) which is prevented from contacting the solid sorbent before activating the second propulsion pump. In such systems, the first and second propulsion pump are configured such that the first propulsion pump can serve as a means for activating said second propulsion pump.

For example, the outlet channel connected to the enclosure of the solid sorbent of the first propulsion pump may connect with the reservoir (and/or inlet channel) containing said working liquid. It also may be connected to the enclosure of the solid sorbent of the second propulsion pump.

Hence, upon activation of the first propulsion pump, the fluid, flowing from the outlet channel of the first propulsion pump into the reservoir and/or inlet channel, activates the second propulsion pump by pushing the working liquid contained therein towards, and into contact, with the enclosed solid sorbent of the second propulsion pump, resulting in the absorption of the working liquid by this sorbent.

In other embodiments, milli- or microfluidic systems according to the second object of the invention may comprise more than two propulsion pumps, acting on a different or the same outlet channel. The plurality of propulsion pumps may be connected in series and activate one another as explained above. Alternatively, two propulsion pumps may be connected in parallel, either with their inlet to the outlet of a third propulsion pump, for being activated by this third propulsion pump; or with their outlets both to the inlet of a third propulsion pump, for both together activating the third propulsion pump.

In another aspect, the present invention provides a milli- or microfluidic point of care diagnostic device comprising a propulsion pump according to embodiments of the present invention.

In yet another aspect, the present invention provides a lab-on-chip device or a drug delivery device comprising a propulsion pump according to the present invention.

The present invention provides the use of a milli- or microfluidic propulsion pump according to any of the embodiments of the first aspect in a milli- or microfluidic system wherein said milli- or microfluidic system is a lab-on-chip (LOC) or point of care diagnostic or drug delivery device.

In another object, the present invention provides a delivery system for delivering a target molecule or agent, for instance a bioactive compound, into a target location, for instance through an injection needle or one or more microneedles. The target location can be a cell, a tissue or a living organism such as a plant or animal. The present invention for instance provides a patch for the delivery of a medicinal or veterinary compound, wherein said patch comprises a propulsion pump according to embodiments of the first aspect of the present invention and at least one hollow needle, preferably a microneedle, the microneedle comprising a channel connecting a needle inlet opening with an open free end, adapted for being introduced in a human or animal tissue. Within said patch the outlet channel of said propulsion pump comprises a solution or suspension containing said compound to be delivered, or is connected to a reservoir for containing or comprising such solution or suspension. Said outlet channel or reservoir is further connected to the inlet of said hollow microneedle such that by activating the propulsion pump said solution or suspension can be pumped via said inlet towards the open free end of the microneedle and preferably into a tissue in which the microneedle is introduced.

In another aspect, the present invention also provides a fluid conduit system, particularly a valve system, which can be used in combination with the pumps and systems of the previous aspects such as actuators for activating pumping or suction action, and which may provide manipulation of fluid by providing propulsion by fluid sorption by enclosed sorbent, providing differences of pressure thanks to the gas-permeable liquid-sealed unit with vent hole and a conduit zone pre-filled with liquid. More specifically, embodiments of the present invention provide a device with fluid conduit system, web or network to manipulate fluids, comprising a fluid actuator unit, a gas-permeable liquid-sealed unit comprising a vent hole, and a solid sorbent enclosed in a chamber with entry access and outlet access engaged with the fluid conduit system.

The gas-permeable liquid-sealed unit with vent and the sorbent enclosure are each engaged by a fluid transit with a fluid conduit that comprises at least three interconnected zones:
i) a first conduit zone upstream of gas-permeable liquid-sealed vent hole unit,
ii) a third conduit zone, upstream of the solid sorbent enclosure, and
iii) a second conduit zone pre-filled with a liquid positioned between the first and third conduit zones, whereby the volume of the first conduit zone is proportionally larger than, or equal to, the volume of the third conduit zone. This advantageously allows proper fluid manipulation, because the majority of the volume of fluid in the third conduit zone can be manipulated by movement of a part of the volume of fluid in the first conduit zone.

It is noted that fluid manipulation includes mixing, separating, and/or moving gases or liquids, e.g. moving gases or liquids along conduits and/or into inlets, out of outlets, or into chambers.

In some embodiments of the present invention, the gas-permeable liquid-sealed unit with vent is engaged, by direct access orifice or through a shunt conduit, with the fluid conduit system, web or network, and it is also engaged by the vent for gas discharge or gas intake with the external environment of said device.

In some embodiments of the present invention, the gas-permeable liquid-sealed unit is fixed in the fluid conduit system, web or network, to transit gases and block liquids between intermittent fluid conduits. In particular embodiments, the unit is a patch made of a hydrophobic material containing cavities for gas passage, for instance a hydrophobic paper.

In some embodiments of the present invention, the device further comprises a gas-permeable liquid-sealed unit fixed in the fluid conduit system, web or network, to transit gases and block liquids between intermittent fluid conduits.

In some embodiments, the gas-permeable liquid-sealed unit comprises a hydrophobic material containing cavities for gas passage, for instance a hydrophobic paper. In additional or alternative embodiments, whereby the vent is sealed (e.g. water sealed, liquid sealed), for example by a hydrophobic material containing cavities for gas passage, for instance a hydrophobic paper.

In some embodiments of the present invention, the device includes a fluid port or opening, which acts as "fluid transit".

In some embodiments of the present invention, the first conduit zone comprises a liquid, e.g. it may be prefilled with a liquid.

In some embodiments of the present invention, the first conduit zone is prefilled with a liquid into the gas-permeable liquid-sealed unit with vent contacting the gas-permeable seal. In particular embodiments, moreover, the liquid is interconnected with liquid that is prefilling the second conduit zone.

In some embodiments of the present invention the third conduit zone is pre-filled with gas. The conduit may be a channel or tube.

In some embodiments of the present invention the device further comprises two propulsion pumps simultaneously activatable by an actuator with exit in the same zone, for instance an analysis or reaction zone, of a conduit, when operational, in order to mix their fluids (e.g. their liquids).

In some embodiments of the present invention, the device comprises a further propulsion pump (e.g. the device includes two propulsion pumps, or more) with exit in the same zone, consequentially activatable by an actuator. The propulsion pumps may exit to, for instance, an analysis or reaction zone, of a conduit, to sequentially deliver their fluid to the same zone in said conduit when operational.

In some embodiments of the present invention, the device may comprise a first propulsion pump engaged to activate a second propulsion pump.

The elements of the device may be arranged and functionally connected to each other, to perform a diversity of actions of fluids, e.g. on liquids. For example, the pumps, fluid reservoirs, at least one gas-permeable liquid-sealed unit with vent and at least one gas-permeable liquid-sealed unit may be engaged in the conduit system, web or network to mix different fluids, and/or to sequentially deliver different fluids and/or to push forward and back in a same conduit zone, for instance an analysis zone, reaction zone or zone enclosing a hydrophilic-in-hydrophobic (HIH) microtube or microwell grids array.

In some embodiments of the present invention, the solid sorbent may be shaped in order to improve sorption, for example, it may be tapered towards the inlet port. For example, the solid sorbent may be a solid 3D object shaped (for instance a cone), tapered towards the inlet port. For example, the solid sorbent may be swellable and its chamber or enclosure may comprise at least one expandable wall.

In some embodiments of the present invention, the unit with a vent hole may function as a valve.

In some embodiments of the present invention, the solid sorbent may be a liquid absorbent.

In some embodiments of the present invention, the fluid conduit comprises a shunt conduit physically or functionally connected with a port for sampling fluid, for instance fluid from the environment, or fluid surrounding or in contact with the port, more in general ambient fluid.

In some embodiments of the present invention, the port has a seal of any one of the group consisting of a valve seal, a seal that can be in a closed or open position and a seal that is removable, openable or closable to open or close the shunt conduit.

In some embodiments of the present invention, the fluid conduit comprises a shunt conduit physically or functionally connected with a reservoir that can contain or contains any one of the group consisting of a working fluid, an analyte, a ligand, a biological active molecule, a chemical reactive molecule and a physical reactive molecule. For example, the reservoir may be an enclosure that is openable or closeable for instance by a seal that is removable, or a seal that can be in a closed or open position.

In some embodiments of the present invention, the fluid actuator comprises a fluid within a depressible enclosure.

In some embodiments of the present invention, the conduits are adapted so the fluids therein are geometrically constrained to millimeter scale, or lower, for example to sub-millimeter scale.

In some embodiments of the present invention, the device is miniaturized to manipulate, move, mix or separate milliliter fluids, or even lower volumes, for example microliter fluids or nanoliter fluids.

In some embodiments of the present invention, the device is miniaturized on a single chip.

In some embodiments of the present invention, no external actuation means are additionally used for a directed transport of the media. The device may require only actuation by manual means, e.g. by pressure of the finger of a user, and it consumes no additional energy to operate. For example, the actuated fluid manipulation does not require any other external force, or centrifugal, thermal, electromechanical and/or electronic generation or actuation.

In some embodiments of the present invention, the solid sorbent enclosed in the chamber is a propulsion pump, comprising a solid sorbent enclosed in an enclosure, which may have a diamond shape, or a circular sector. Alternatively, the device comprises a propulsion pump comprising a solid sorbent enclosed in an enclosure. Thus, in some embodiments the device includes a propulsion pump, an actuator and a gas-permeable liquid-sealed unit comprising a vent hole. In any case, the solid sorbent contains cavities or capillars comprising a first fluid, and the enclosure of the solid sorbent comprises a first opening through which the solid sorbent can be contacted with a liquid and a second opening connecting the enclosure to an outlet channel. The propulsion pump is adapted for being activated by contacting said solid sorbent with a liquid, via said first opening, resulting in the absorption of at least part of said liquid by the solid sorbent. This absorption is associated with the expulsion of at least part of said first fluid from the cavities of said solid sorbent into said outlet channel. The flow of said first fluid into the outlet channel allows for propulsing and/or compressing a second fluid contained in said outlet channel and/or in a channel or reservoir physically or functionally connected to said outlet channel.

In some embodiments of the present invention, said first opening connects to an inlet channel suitable for bringing a liquid into contact with said solid sorbent via said first opening in order to activate said propulsion pump. Moreover, in some embodiments, said inlet channel contains a liquid and/or connects to a reservoir containing a liquid, referred to as working liquid, wherein prior to the activation of the propulsion pump the working liquid is prevented from contacting said solid sorbent. A portion of the inlet channel including working fluid forms the second conduit zone, and it is prevented from contacting the solid sorbent by the first conduit zone. The propulsion pump comprises activation means or actuators for moving the working liquid in the inlet channel through the first conduit zone, such that it contacts said solid sorbent via said first opening resulting in the absorption of at least part of the working liquid by said solid sorbent.

Further, in some embodiments of the present invention, the activation means or actuators comprise a flexible or depressible wall integrated in a wall of said inlet channel and/or reservoir, and the propulsion pump is adapted for being activated by applying a sufficient pressure on said flexible or depressible wall. The deformation of said pressed flexible or depressible wall acts on the working liquid in the inlet channel and/or reservoir, in particular on the liquid (working liquid, or a trigger liquid) in a third conduit zone, with a volume larger than the volume of the first conduit zone, such that the working liquid moves in the inlet channel and contacts said solid sorbent via said first opening resulting in the absorption of at least part of the working liquid by said solid sorbent.

Further, in particular embodiments, the inlet channel and/or reservoir containing the working liquid are connected to a micro- or millifluidic network. The arrangement results in the effect that, upon activation of the propulsion pump, the absorption of said working liquid from the inlet channel and/or reservoir by the solid sorbent exerts a suction force on the fluids contained in said connected micro- or millifluidic network. The network may comprise at least a channel having an inlet opening, and the suction force allows for pulling in a liquid positioned on said inlet opening into said channel.

However, the present invention is not limited to "working liquid". In particular, in some embodiments of the present invention, the first fluid is a gas.

In some embodiments the device includes a propulsion pump, an actuator and a gas-permeable liquid-sealed unit comprising a vent hole device, wherein some features comprise particular embodiments from previous aspects of the present invention; for example the solid sorbent of the propulsion pump is a porous material, wherein said cavities are interconnected pores, or a capillary material, wherein said cavities are open ended capillaries, or a mixed material comprising both such capillaries and pores.

Additional features may be included. For example, the device may include an analytical zone in fluid connection to the outlet channel. The analytical zone is adapted for receiving an analyte, and it may be provided with a detector unit for detecting properties of analyte in the analytical zone. Any suitable detector can be used. For example, as explained earlier, the detector unit may comprise a plasma resonance detector, e.g. a fiber optic surface plasma resonance detector.

In a further aspect of the present invention, a device can be provided for delivery of a liquid into a tissue. The device may provide a fast delivery, e.g. faster than 1 microliter per hour, at a suitable pressure for transdermal delivery, and with a wide range of delivery volume. Such device may advantageously be self-powered, e.g. it may not need an external power source. The principles of actuation are based in, and share common features, with previous aspects of the present invention. In particular, a self-powered microliter liquid system is provided, for injecting a liquid into a tissue, where its delivery system comprises at least one microneedle coupled to a device comprising at least one milli- or microfluidic capillary propulsion pump. The capillary propulsion pump comprises a solid sorbent enclosed in an enclosure, said solid sorbent containing cavities comprising a first fluid, and the enclosure of the solid sorbent comprises a first opening, through which the solid sorbent can be contacted with a liquid. The enclosure further comprises a second opening connecting the enclosure to an outlet channel. The propulsion pump is adapted for being activated by contacting said solid sorbent with a liquid via said first opening, resulting in the absorption of at least part of said liquid by the solid sorbent. As noted earlier, this absorption is associated with the expulsion of at least part of said first fluid from the cavities of said solid sorbent into said outlet channel, whereby the flow of said first fluid into the outlet channel allows for propulsing and/or compressing a second fluid contained in said outlet channel and/or in a channel or reservoir connected to said outlet channel.

In some embodiments of the present invention, the solid sorbent comprises a porous material or materials, including cavities which may be interconnected pores, open ended capillaries, a mixed material comprising both, etc.

In some embodiments of the present invention, the first fluid which is included in the cavities of the solid sorbent may be a gas.

In some embodiments of the present invention, the first opening connects to an inlet channel suitable for bringing, via the opening, a liquid into contact with said solid sorbent, in order to activate said propulsion pump.

In some embodiments of the present invention, the inlet channel contains a liquid ("working liquid") and/or connects to a reservoir containing that liquid, which is prevented from contacting the solid sorbent prior to the activation of the propulsion pump. The propulsion pump comprises activation means, or actuators, for moving the working liquid in the inlet channel, such that it contacts the solid sorbent via said first opening when the actuator is used, resulting in the absorption of at least part of the working liquid by said solid sorbent.

In some embodiments of the present invention, the activation means (actuator or actuators) may comprise a flexible or depressible wall integrated in a wall of said inlet channel and/or reservoir. The propulsion pump is adapted for being activated by applying a sufficient pressure on said flexible or depressible wall. The deformation of said pressed flexible or depressible wall acts on the working liquid in the inlet channel and/or reservoir, such that the working liquid moves in the inlet channel (e.g. moves through the first conduit zone) and contacts said solid sorbent via said first opening, resulting in the absorption of at least part of the working liquid by the solid sorbent.

In some embodiments of the present invention, the inlet channel and/or reservoir containing the working liquid are further connected to a micro- or millifluidic network, so upon activation of the propulsion pump, the absorption of said working liquid from the inlet channel and/or reservoir by said solid sorbent exerts a suction force on the fluids contained in the connected micro- or millifluidic network. For example, in some embodiments, the micro- or millifluidic network comprises a channel having an inlet opening. The suction force allows for pulling in a liquid positioned on said inlet opening into said channel.

In some embodiments of the present invention, the system may include an analytical zone in fluid connection to the outlet channel. The analytical zone can be adapted for receiving an analyte, and be provided with a detector unit for detecting properties of analyte in the analytical zone, e.g. a fiber optic surface plasma resonance detector.

In a further embodiment, a milli- or microfluidic system comprising a self-powered liquid system is provided.

In some embodiments of the present invention, the milli- or microfluidic system further comprises a suction pump. In some embodiments, said suction pump serves as an activation means or actuators of the propulsion pump introduced earlier, wherein the inlet channel of the propulsion pump is operably connected to the suction pump. Following the activation of the suction pump, a liquid can be moved into the inlet channel of said propulsion pump, such that it contacts said solid sorbent via said first opening, resulting in the absorption of at least part of said liquid by the solid sorbent.

In particular embodiments, the suction pump comprises a further solid sorbent enclosed in a further enclosure comprising one or more vent-holes, and an opening connecting the further enclosure to a further inlet channel and/or to a further reservoir. The channel and/or reservoir, or both, contain a liquid, referred to as a "further working liquid". The further inlet channel and/or further reservoir are further operably connected to an inlet channel of the propulsion pump introduced earlier.

The suction pump is adapted for being activated by contacting said "further working liquid" to the further solid sorbent of the suction pump, resulting in the absorption of the further working liquid from said further reservoir and/or further inlet channel by this further solid sorbent, so a suction force is exerted on a liquid introduced or contained in the inlet channel of said propulsion pump. The liquid is moved towards and brought into contact with said solid sorbent of the propulsion pump.

In some embodiments of the present invention, a second propulsion pump is included. The first and second propulsion pumps are configured such that the first propulsion pump can serve as a means for activating said second propulsion pump. For example, the outlet channel connected to the enclosure of the solid sorbent of the first propulsion pump connects with said reservoir and/or inlet channel containing the working liquid and being connected to the enclosure of the solid sorbent of the second propulsion pump. Upon activation of said first propulsion pump, the fluid flow from the outlet channel of the first propulsion pump into the reservoir and/or inlet channel activates the second propulsion pump, by pushing the working liquid contained therein towards and into contact with the enclosed solid sorbent of the second propulsion pump resulting in the absorption of the working liquid by this sorbent.

In some embodiments of the present invention, the device is adapted for providing self-powered delivery of liquids in to a tissue, or through skin or other biological tissue barriers, with controlled flow rate at high pressures of 50 to 100 kPa, for example 60 to 70 kPa.

In some embodiments of the present invention, the device is adapted for delivery of small volumes of liquids, for instance volumes in the range 1-1000 μL or even lower, e.g.

0.1 µL to 1000 µL, and preferably in the range of 100 µl to 300 µl in to a tissue or through skin or other biological tissue barriers.

In some embodiments of the present invention, the device is adapted for delivery of liquids with different viscosities, for instance in the range of $0.5*10^{-3}$ Pa*s to $75*10^{-3}$ Pa*s and preferably in the range of $0.9*10^{-3}$ Pa*s up to $60*10^{-3}$ Pa*s in to a tissue or through skin or other biological tissue barriers with controlled flow rate at high pressures of 50 to 100 kPa or 60 to 70 kPa.

In another aspect, the present invention provides the use of a self-powered microliter liquid system according embodiments of the previous aspect, in a milli- or microfluidic system integrated in a patch for the delivery of a medicinal or veterinary compound.

In another aspect, the present invention provides a patch for the delivery of a medicinal or veterinary compound. The patch comprises a propulsion pump according to embodiments of the previous aspects and at least one hollow microneedle, comprising a channel connecting a needle inlet with an open free end, adapted for being introduced in a tissue. The outlet channel of the propulsion pump comprises a solution or suspension containing said compound, or is connected to a reservoir comprising such solution or suspension, wherein said outlet channel or reservoir is connected to the inlet of the hollow microneedle such that, by activating the propulsion pump, said solution or suspension is pumped via the inlet towards the free end of the microneedle, and into the tissue in which the microneedle is introduced.

In some embodiments of the present invention, the patch is flexible or depressible.

For seeding of microbeads in a digital assay platform, current methods rely on expensive, not user-friendly and power-dependent microfluidic platforms for liquid manipulation which are not compatible with POC application, low cost production, robustness and user-friendliness.

Here, we solve these technical problems by integrating the digital assay concept on a milli- or microfluidic platform such as the suction/propulsion platform which would result in a self-powered, programmable microfluidic manipulation on a disposable, low-cost and easy to use chip.

Thus, in a further aspect of the present invention, a microfluidic device is provided, including a sample delivery section for applying a liquid containing magnetic beads operationally connected to a detection zone with one or more recessed parts and a magnet positioned in the proximity of the detection zone so that when operational the beads are immobilized in the recessed part of the detection zone in one continuous flow.

In some embodiments of the present invention, the magnetic beads are positioned to the walls of the sample delivery section.

In some embodiments of the present invention, a capillary delivery pump is further included.

In some embodiments of the present invention, the capillary delivery pump is a suction pump for providing the continuous flow to immobilize said beads in the recessed part.

In some embodiments of the present invention, the suction pump comprises a solid sorbent enclosed in an enclosure, said solid sorbent containing cavities comprising a first fluid. The enclosure of the solid sorbent comprises a first opening through which said solid sorbent can be contacted with a liquid and a second opening connecting the enclosure to an outlet channel and wherein said suction pump is adapted for being activated by contacting said solid sorbent with a liquid via said first opening resulting in the absorption of at least part of said liquid by the solid sorbent resulting in a suction force exerted on a liquid introduced or contained in the inlet channel of said suction pump such that said liquid is moved towards and brought into contact with said solid sorbent.

In some embodiments of the present invention, the solid sorbent is shaped in a 10° up to 150° circular sector, for example 50° to 70° circular sector to provide a flow rate of about 4 to 10 µl/min.

In some embodiments of the present invention, the recessed parts are a set of indentations with a shape complementary to the beads.

In some embodiments of the present invention, the magnet is positioned perpendicular or almost perpendicular at an angle in the range of 85-95° underneath the detection zone. Moreover, in some embodiments the magnet may be at least as large as the surface of the detection zone.

In particular embodiments, the magnet has a strength of about 1.3 T and is positioned about 1.5 to 2.5 mm below the recessed part.

In some embodiments of the present invention, the bead concentration in the liquid is about $2*10^7$ to $10*10^7$ beads/ml.

In some embodiments of the present invention including the detection zone and a magnet for immobilizing magnetic beads, a propulsion pump is present comprising a solid sorbent enclosed in an enclosure, said solid sorbent containing cavities comprising a first fluid, wherein said enclosure of the solid sorbent comprises a first opening through which said solid sorbent can be contacted with a liquid and a second opening connecting the enclosure to an outlet channel and wherein said propulsion pump is adapted for being activated by contacting said solid sorbent with a liquid via said first opening resulting in the absorption of at least part of said liquid by the solid sorbent; whereby this absorption is associated with the expulsion of at least part of said first fluid from the cavities of said solid sorbent into said outlet channel, whereby the flow of said first fluid into the outlet channel allows for propulsing and/or compressing a second fluid contained in said outlet channel and/or in a channel or reservoir connected to said outlet channel.

In some embodiments of the present invention, at least a transparent section for visual inspection of the beads is present.

In further aspect of the present invention, a kit of parts if provided, the kit comprising the microfluidic device according to the previous aspect of the present invention and functionalized magnetic beads.

In some embodiments of the present invention, a method for immobilizing magnetic beads on a detection zone is provided. The method can be applied in a microfluidic device according to embodiments of the previous aspects of the present invention. The method comprising the steps of 1) adding a liquid with to the sample delivery section or adding a liquid to the delivery section whereon magnetic beads are positioned, 2) applying a continuous liquid flow thereby transporting the beads into the direction of the detection zone and 3) applying force with a magnetic strength sufficient to retain the magnetic beads in the recessed zone of the detection zone.

In some embodiments of the method, the method further comprises the steps of applying substrate and subsequently oil over the magnetic beads.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF DRAWINGS

The invention will now be described further, by way of example, with reference to the accompanying drawings, in which:

FIGS. 4(A) to 4(H) show a stepwise representation of the prefilling of a microfluidic propulsion pump according to the embodiment of FIGS. 3(A) to 3(C) of the present invention, in side view and in top view.

FIGS. 5(A) to 5(D) show a schematic representation of the operation of an embodiment of a propulsion pump system according to the present invention.

FIG. 20(B), operation of the propulsion pump (so called iSIMPLE) chip with microneedle array while injecting in 1% agarose matrix. FIGS. 20(C) and 20(D), top and side view of the agarose matrix after injection were the red colored outlet liquid is clearly injected in the matrix.

FIGS. 22(A) to 22(D) are a schematic illustration of a device with fluid conduit system to manipulate fluids including the elements of a fluid actuator unit, a shunt conduit with downstream a gas-permeable liquid-sealed vent hole, (e.g. a unit with vent hole forming a hydrophobic valve), and a capillary pump. It also provides a drawing of the phases of the activation of propulsion pump in a design with hydrophobic valve.

FIG. 24(A), displays gates and valves adapted to form a passageway for gas and a barrier for liquid. The FIGS. 24(B) to 24(H) demonstrate such device at actuation and in various phases of its operation.

FIGS. 26(A) to 26(F) are a graphic that demonstrates an embodiment with a suction pump and propulsion pump series with engagement of a hydrophobic valve (HV) in a design that delays an intermittent activation of a next pumping system.

FIG. 35(A) immobilization of the beads above the array due to too high magnetic attraction (distance of 1.75 mm), FIG. 35(B) good seeding (distance of 2.4 mm), and FIG. 35(C) low seeding due to low magnetic attraction (distance of 3.5 mm).

FIG. 38(A) brightfield pictures taken of one array with 15x objective, and FIG. 38(B) pictures taken of second array with some defaults with 40x objective both showing seeding over 92%.

FIGS. 48(A) and 48(B) illustrate the influence of the hydrophobic valve in the activation of a microfluidic system (iSIMPLE design), in particular an example of failed activation in a system without hydrophobic valve and the comparison with the successful activation of a system including the hydrophobic valve

Figures 1A, 1B, 1C, 1D, 1E, 1F, 2A, 2B, 2C, 2D, 3A, 3B, 3C:
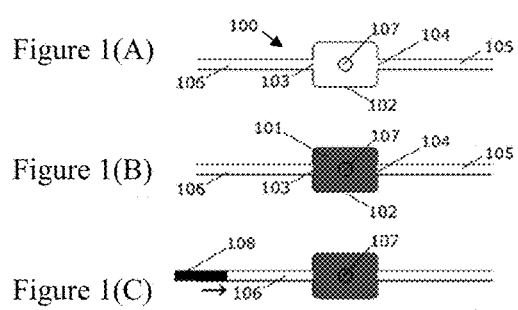
FIGS. 1(A) to 1(F) show the schematics of pump design and prefilling steps.
FIGS. 2(A) to 2(D) show the schematic representation of the activation and operation of an embodiment of the propulsion pump of the present invention.
FIGS. 3(A) to 3(C) show the fabrication of an embodiment of a microfluidic propulsion pump of the present invention.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope.

In the different drawings, the same reference signs refer to the same or analogous elements.

Detailed Description of Illustrative Embodiments

The present invention will be described with respect to particular embodiments and with reference to certain drawings but the invention is not limited thereto but only by the claims.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, directional terminology such as top, bottom, front, back, leading, trailing, under, over and the like in the description and the claims is used for descriptive purposes with reference to the orientation of the drawings being described, and not necessarily for describing relative positions. Because components of embodiments of the present invention can be positioned in a number of different orientations, the directional terminology is used for purposes of illustration only, and is in no way intended to be limiting, unless otherwise indicated. It is, hence, to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention provides a milli- or microfluidic propulsion pump 100 comprising a solid sorbent 101 enclosed in an enclosure 102. The solid sorbent 101 contains cavities comprising a first fluid. The first fluid may be a liquid, or a gas such as for instance air. The enclosure 102 of the solid sorbent 101 comprises a first opening 103 through which the solid sorbent 101 can be contacted with a liquid. The enclosure 102 furthermore comprises a second opening 104, through which the first fluid can be evacuated from the enclosure 102. The second opening 104 connects the enclosure 102 to an outlet channel 105. The propulsion pump 100 is adapted for being activated by contacting said solid sorbent 101 with a liquid via said first opening 103, for instance a liquid flowing in an inlet channel 106, resulting in the absorption of at least part of said liquid by the solid sorbent 101. This absorption of liquid by the solid sorbent 101 is associated with the expulsion of at least part of the first fluid from the cavities of the solid sorbent 101 through the second opening 104 into the outlet channel 105. The flow of the first fluid into the outlet channel 105 allows for propulsion and/or compression of a second fluid contained in the outlet channel 105 and/or in a channel or reservoir connected to said outlet channel 105.

In some embodiments of the present invention, the solid sorbent is a porous material, which may absorb liquids. For example, it may be hydrophilic (or oleophilic or lipophilic, if the working liquid is oily). It may be a filter paper.

The gate adapted to form a passageway for gas and a barrier for liquid, for instance an hydrophobic patch can for instance comprising a gas-permeable liquid-impermeable membrane. Preferably it is a porous material, so that the air can flow through, that do not show affinity with the liquid in contact. In present invention for instance hydrophobic properties are used for watery liquids or hydrophilic if liquid used is oil-based. In present example an as a specific embodiment of the invention such hydrophobic patch is made of a filter paper which is made hydrophobic by applying silicon or fluorinated compounds (i.e. Aquapel solution). In the first case, Whatman 1PS Phase Separator Papers was used (silicon based), while in the second, a fluorinated compounds (i.e. Aquapel solution) was deposited on a filter paper (i.e. Whatman grade 43) at around 0.18 µL/mm2 and eventually let it dry completely. These two treatments make the fiber of the porous material hydrophobic maintaining at the same time the porous structure of the filter paper. This hydrophobic patch can be shaped as needed using the same table top cutter as the one used for the suction pump/propulsion pump fabrication.

The gate adapted to form a passageway for gas and a barrier for liquid, can be integrated in a microfluidic device for instance acting as i) a barrier or ii) a valve for instance acting as i) a hydrophobic barrier or ii) a hydrophobic valve for conduits with aqueous liquids or for instance acting as i) a hydrophilic barrier or ii) a oleophobic valve for conduits with oily liquids.

Where reference is made to a "hydrophobic valve", reference is made to a unit with a vent hole, e.g. a gas-permeable liquid-sealed unit with a vent hole; however it may also be a lipophobic or oleophobic valve, if the working fluid or trigger fluid is oily. In some cases, the hydrophobic valve or its materials can be used as a barrier or part thereof.

In case the liquid-barrier gas-passageway gate is a barrier (for instance an hydrophobic barrier for aqueous liquids or an hydrophilic barrier for oily liquids) such liquid-barrier gas-passageway gate is for instance a patch that is embedded in a microfluidic channel connected to the inlet and outlet of the devices through channel partially filled with liquids (A upstream, B downstream). The technical effect thereof is that it physically separates these liquids (upstream and downstream the barrier) while at the same time keeping the two sections of the device connected. In fact if the liquid A is pushed/pulled through the inlet, the effect is transferred to liquid B and vice versa, because the over/under pressure generated will be transmitted by the air between the two liquids that on its turn can freely go through the barrier. The two parts of the device are not connected anymore once the liquid A (or liquid B) reaches the barrier. In this case, the liquid B (or liquid A) cannot push/pull the liquid A (or liquid B) anymore because it is blocked by the barrier.

In case the liquid-barrier gas-passageway gate is a valve it can be in the form of a patch. Although the rest of the description refers mainly to hydrophobic material and hydrophobic valves, the present invention is not limited thereto, and a hydrophobic patch can be used for aqueous liquids and hydrophillic (and/or oleophobic) patch for oily liquids. The patch may be embedded in a microfluidic channel connected to the inlet and outlet of the devices through channel partially filled with liquids (A upstream, B downstream), forming a barrier for liquids, but also directly connected to the outside via a vent hole, for example forming a unit with a vent hole where the patch allows the passage of air but stops passage of liquid. A third liquid C, also called trigger liquid, can be upstream or at the interface with the valve (e.g. with the unit with a vent hole acting as a valve). Part of the valve is then connected to the microfluidic channel side and part to the atmosphere via the vent hole. When an under pressure is applied to the outlet, liquid B is pulled along the channel while liquid A is pulled only if the valve is covered by the liquid C. In fact if the valve is not blocked by the liquid C, the under pressure applied to the outlet is not applied to the liquid A since there is a vent hole between, represented by the hydrophobic valve. If the valve is covered by the liquid C, the under pressure applied to the outlet is applied to the liquid A as long as the liquid C keeps blocking the valve. From the moment the liquid C overcomes the valve interface, the liquid A is not pulled anymore. Similarly, if an over pressure is applied to the inlet, the liquid A is pushed downstream along with the liquid C. The liquid B is pushed only when the liquid C and later on the liquid A, block the valve, otherwise the air pushed by the liquid C and A can escape from the hydrophobic valve without affecting the liquid B. Using the valve, delay between different liquids manipulation can be programmed and tuned. Moreover, suction pumps and propulsion pumps can be activated sequentially with a desired time in between. The patch, compared to other valves/barrier, are robust, easy to fabricate, inexpensive and provide a physical barrier or a phase selective (air/liquid) valve system.

In another embodiment of the invention microbeads are seeded in a microwell array under continuous flow with the Suction Pump.

Magnetophoresis is used in the present invention to enhance the seeding efficiency of superparamagnetic microbeads in the HIH wells array.

Magnetophoresis can be described as the motion of magnetic particles through a medium induced by an external magnetic field. Magnetophoresis finds its applications in separation processes where magnetic particles are used as solid phase carriers in biological assays and can be subsequently manipulated due to their superparamagnetic properties. The advantages of using superparamagetic beads in biological assays are: i) sample handling is easier, ii) magnets can be positioned externally (allowing manipulation of the beads externally), iii) in contrast to electric separation, magnetic forces are not influenced by temperature, pH and ionic strength, and iv) the magnetic labeled beads can be retained on the microwell array for a digital analysis.

Superparamagnetic beads are typically magnetic nanoparticles embedded in a polymer matrix and can be made of a polystyrene shell and an iron oxide core and therefore they have the typical ferromagnetism magnetic susceptibilities (permanent magnetic materials) while in the presence of a magnetic field. This produces some interesting properties: i) they are used as solid phase carriers and can be subsequently manipulated due to their magnetic properties, and ii) the iron oxide core, which causes the beads to be magnetic, cannot interfere with biological reagents. However, when the external field is removed, the global magnetic permeability μ of the bead returns to zero due the redistribution of the magnetic moments. Thus, these beads can be strongly magnetic but at the same time conserve the property of reversibility typical of the paramagnetism. For these reasons these beads are called 'superparamagnetic'.

Many biological assays require multiple sequential reaction and washing steps. This can be very time-consuming when using a batch method. To overcome the limitations of batch processes, different approaches for continuous flow separation of magnetic material have been presented: i) the separation of magnetically labeled cells in a quadrupolar magnetic field of a separation chamber similar to a free-flow electrophoresis device, ii) magnetic separation in a continuous flow for fractionation, here, an external magnetic field pulls magnetic beads from their flow stream into a another buffer stream to perform a washing or reaction steps in a continuous flow system. iii) an electrowetting-on-dielectric-based (EWOD) digital microfluidic chip where a droplet containing suspended superparamagnetic beads is moved over a HIH wells array and by using a magnet underneath the array, the beads are seeded in the wells, iv) a microfluidic and magnetic setup to separate superparamagnetic microparticles from sample droplets in water-in-oil droplet segmented flow for purification, immobilization and optimizing the separation efficiency.

In a particular embodiment, a self-powered POC device with a porous material shaped in 60° circular sector used to provide a flow rate of 6.59±0.78 μL/min, a magnet distance of 1.95 mm and a bead concentration of $5 \times 10^7$ beads/mL is presented here. These values are only indicative, and other concentrations may be used, independently of the magnet distance, flow rate or shape or type of capillary pump. This system proves to be reliable and when used to seed microbeads guarantees the proper flow rate to achieve a seeding efficiency of 91.6%. High seeding efficiency (i.e. more than 90%) may be achieved in less than 30 sec without the need of an external instrument or power supply. In more particular embodiments the Suction Pump platform may be used to first seed and then seal microbeads combining a propulsion pump, with the aim to design a self-powered POC device with unprecedented sensitivity.

FIGS. 1(A) to 1(F) illustrates different steps in the process of prefilling of a milli- or microfluidic propulsion pump 100 according to embodiments of the present invention, i.e. before the propulsion pump 100 is actually used as a pump.

FIG. 1(A), before its prefilling the pump 100 comprises an enclosure 102, said enclosure 102 comprising a first opening 103 connected with an inlet channel 106, a second opening 104 connected with an outlet channel 105 and a vent-hole 107. FIG. 1(B), solid sorbent 101, in the example illustrated for instance in the form of porous material comprising cavities filled with air, is hosted in the enclosure 102 and the vent-hole 107 is open. FIGS. 1(C) and 1(D), with the vent-hole 107 still open, the inlet channel 106 is filled with working liquid 108 until it is close to the solid sorbent 101 (e.g. porous material), but does not contact the porous material (solid sorbent 101) yet. FIG. 1(E), with the vent-hole 107 still open, outlet liquid 109 is then injected in the outlet channel 105. By having the vent-hole 107 open, overpressure in the propulsion pump 100 can be avoided. FIG. 1(F), when the device 100 is properly prefilled, the vent-hole 107 is closed and the device 100 is ready to use or to be stored for later use.

FIGS. 2(A) to 2(D) illustrate steps in the actual use of a device 100 as a propulsion pump.

FIG. 2(A), following the prefilling of said propulsion pump 100 (see FIGS. 1(A) to 1(F)), the pump 100 comprises a solid sorbent 101 (porous material) enclosed in an enclosure 102 connected via a first opening 103 to an inlet channel 106 containing a working liquid 108, and via a second opening 104 to an outlet channel 105 containing the outlet liquid 109. The vent-hole 107 is closed. The starting step illustrated in FIG. 2(A) corresponds to the finishing step of the pre-filling process as illustrated in FIG. 1(F). Neither the working liquid 108 nor the outlet liquid 109 contact the solid sorbent 101. The device 100 may have been pre-filled immediately before the actual use as a pump, or it may have been pre-filled a longer time before, and have been stored. FIG. 2(B), the pump 100 is activated by generating a pressure 200 on the working liquid 108 in the inlet channel 106, thus moving the working liquid 108 such that it contacts the solid sorbent 101, for instance at the first opening 103, and gets absorbed. FIG. 2(C), the absorbed working liquid 108 expulses the air 201 out of the porous material (solid sorbent 101) into the outlet channel 105, and this expulsed air, in turn, pushes the outlet liquid 109 further in the outlet channel 105, away from the enclosure 102. FIG. 2(D), the pump operation terminates (i) when all the working liquid 108 is drawn in the porous material (solid sorbent 101) or (ii) when the porous material (solid sorbent 101) gets saturated with working liquid 108. During this whole process, the vent-hole 107 remains closed.

FIGS. 3(A) to 3(C) illustrate how a microfluidic propulsion pump 100 according to embodiments of the present invention may be manufactured. In embodiments of the present invention, the microfluidic propulsion pump 100 may be assembled from a plurality of layers and/or elements with different characteristics and functions. In the embodiment illustrated, the propulsion pump 100 is assembled from three layers, and a chamber is filled with solid sorbent material.

FIG. 3(A), representation of the four different elements to be assembled in one embodiment of a fabrication method of the pump 100:

(i) A bottom layer 301 in solid material, for supporting the propulsion pump 100. In particular embodiments, the solid material of the bottom layer 301 may be a light weight material, as this is a useful property in for instance LOC and POC applications. The solid material of the bottom layer 301 may be cheap material, which is desirable in case the propulsion pump 100 is embedded in a disposable device. The solid material of the bottom layer 301 should be resistant against, e.g. not corroded by, and not absorbing, the fluids present in or flowing through the enclosure 102, the inlet channel 106 and the outlet channel 105. In particular embodiments, the solid material of the bottom layer 301 is hydrophobic material, to prevent the liquid to move autonomously by capillarity. In embodiments of the present invention, the solid material of the bottom layer 301 may be transparent, for instance to allow visual inspection. The solid material of the bottom layer 301 may be shatter resistant. The thickness of the bottom layer may be limited; it may for instance not more than a few µm, such that the bottom layer in fact may be nothing more than a sheet of material. The solid material may for instance be plastic material (e.g. PVC or PMMA).

(ii) A double sided pressure sensitive adhesive (PSA) layer 302 in which a milli- or microfluidic channel 303 is cut, for instance with an electronic craft cutting machine. The milli- or microfluidic channel 303 comprises at least a section which, upon assembling the elements, will form the enclosure 102 for enclosing the solid sorbent 101. The milli- or microfluidic channel 303 may furthermore comprise at least part of the inlet channel 106 and/or the outlet channel 105.

(iii) A solid sorbent 101 material. The solid sorbent 101 material may be a porous material (e.g. filter paper) suitably shaped, for instance with an electronic cutting machine, to fit in the part of the milli- or microfluidic channel 303 which will form the enclosure 102.

(iv) A top layer 304 for covering the pressure sensitive adhesive layer 302 and closing the milli- or microfluidic channel. In the top layer 304, an inlet hole 305, for introducing working liquid 108 into the inlet channel 106; an outlet hole 306, for introducing outlet liquid 109 into and evacuating outlet liquid from the outlet channel 105; and a vent-hole 107 may be provided, for instance with an electronic cutting machine. The top layer 304 may be made from any suitable material, for instance a plastic material like PVC or PMMA. Characteristics of the top layer 304 may be similar to the characteristics of the bottom layer 301. The top layer and the bottom layer may be, but do not need to be, made from the same material.

FIG. 3(B), the fabrication sequence is shown: the pressure sensitive adhesive 302 is attached, by applying pressure, on the bottom layer 301; the solid sorbent 101, e.g. the filter paper, is inserted in the section in the milli- or microfluidic channel 303 cut in the pressure sensitive adhesive 302, which will form the enclosure 102; the chip is closed with the top layer 304 positioned and attached on the pressure sensitive adhesive layer 302. FIG. 3(C), representation of the assembled device.

FIGS. 4(A) to 4(H) are a stepwise representation of the pre-filling of a microfluidic propulsion pump according to the embodiment illustrated in FIGS. 3(A) to 3(C). The different steps are illustrated in side view in the left hand column, and in top view at the right hand column.

FIGS. 4(A) and 4(B) before its prefilling the pump 100 comprises i) a bottom layer 301, ii) a layer 302 comprising channels and chambers cut in a pressure sensitive adhesive material, iii) a solid sorbent 101 (porous material), iv) a top layer 304 with an inlet hole 305, an outlet hole 306 and a vent-holes 107. The solid sorbent material 101, e.g. porous material, is hosted in the enclosure 102 forming a porous material chamber, and the vent-hole 107 is open during the prefilling phase, as also explained with reference to FIGS. 1(A) to 1(F). FIG. 4(A) is a cross-sectional side view of the device which is illustrated in top view both in FIG. 3(C) and in FIG. 4(B). FIGS. 4(C) and 4(D), the inlet channel 106 is filled, via the inlet hole 305, with working liquid 108. The working liquid 108 is made to approach but not contact the solid sorbent material 101, e.g. porous material. The working liquid 108 may be forced to travel through the inlet channel 106 by applying an external force, for example by injection. FIGS. 4(E) and 4(F), next, outlet liquid 109 is introduced, e.g. injected, in the outlet channel 105, via the outlet hole 306, also without contacting the solid sorbent material 101, e.g. porous material. FIGS. 4(G) and 4(H), when the device 100 is properly pre-filled the vent-hole 107 is closed and the device 100 is ready to use or to be stored. Closure of the vent-hole 107 can be performed for instance by means of small patches of tape, for instance double sided tape, which can be removed on activation. In particular embodiments, the tape may be gas impermeable.

FIGS. 5(A) to 5(D) are a schematic representation of the operation of an embodiment of a propulsion pump system according to the present invention.

FIG. 5(A), prior to its activation the propulsion pump 100 comprises a solid sorbent 101 (porous material) enclosed in an enclosure 102, preferably in the shape of a circle sector. Using the shape of a circle sector for the enclosure 102 is not a strict requirement for the working of the principle itself but it has been shown in literature that a circular sector shape provides a constant flow rate of the liquids manipulated by the pump, which is a preferred condition in microfluidics.

The enclosure 102 is connected to an inlet channel 106 and to an outlet channel 105. The inlet channel 106 is further connected to an inlet reservoir 501 having a flexible or depressible wall, wherein the inlet reservoir 501 and the inlet channel 106 contain a working liquid 108. The outlet channel 105 comprises an outlet liquid 109 and is connected to an outlet reservoir 502 positioned downstream of the solid sorbent 101. FIG. 5(B), activation: the propulsion pump 100 is activated by applying a pressure 503 to, e.g. by compressing, the flexible or depressible wall of the inlet reservoir 501 connected to the inlet channel 106, thus moving the working liquid 108 in the inlet channel 106 so that it contacts the solid sorbent 101 leading to the absorption of the working liquid 108 by the solid sorbent 101. FIG. 5(C), operation: while the working liquid 108 is absorbed into the solid sorbent 101, it expulses the fluid, for example air, present in the cavities in the solid sorbent 101 into the outlet channel 105. This fluid influx in the outlet channel 105 pushes the outlet liquid 109 towards and into the outlet reservoir 502 downstream of the outlet channel 105. FIG. 5(D), termination: the action of the pump 100 is terminated either when all the working liquid 108 is absorbed into the solid sorbent 101 or when the solid sorbent 101 is saturated by the working liquid 108. The outlet liquid 109 may all be pushed into the outlet reservoir 502, or may still partially be present in the outlet channel 105.

FIGS. 6(A) to 6(D) show an alternative embodiment of a propulsion pump 100 according to the present invention. It is used for investigating the use of this pump 100 for generating a pressure in a microfluidic system.

Figure 6A:
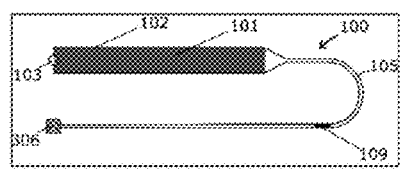
FIGS. 6(A) to 6(D) show an embodiment of a propulsion pump according to the present invention for investigating the use of said pump for generating a pressure in a microfluidic system.
Figure 6B:
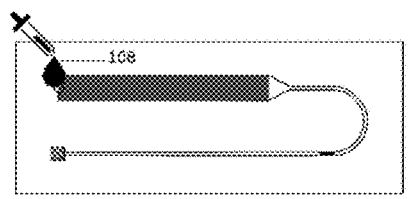
Figure 6C:
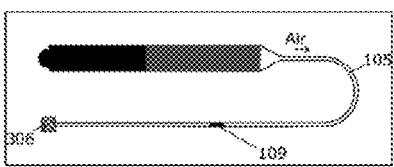
Figure 6D:
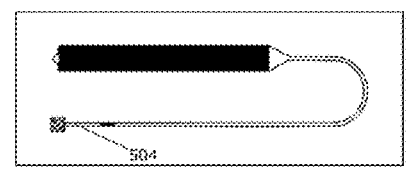

FIG. 6(A), the microfluidic pump 100 comprises a solid sorbent 101 (porous material) enclosed in an enclosure 102. The enclosure 102 comprises a first opening 103 for contacting a liquid to said solid sorbent 101 and a second opening 104 connecting the enclosure 102 to an outlet channel 105. Prior to the activation of the microfluidic pump 100, a liquid plug of outlet liquid 109 was preloaded in said outlet channel 105 via an outlet hole 306, which was sealed after provision of the liquid plug (e.g. acting as outlet liquid 109). FIG. 6(B), activation: a droplet of a working liquid 108 is deposited on the inlet of the propulsion pump 100, e.g. on the first opening 103. FIG. 6(C), operation: while the working liquid 108 is absorbed into the solid sorbent 101, it pushes out the fluid, typically air, present in the cavities in the solid sorbent 101. This fluid, e.g. air, pushes the liquid plug of outlet liquid 109 towards the closed end of the outlet channel 105, i.e. towards the end where the outlet hole 306 has been closed in the pre-filling phase after provision of the outlet liquid 109 plug. FIG. 6(D), yermination: the pumping operation is terminated either when all working liquid 108 is absorbed into the solid sorbent 101 or when the solid sorbent is saturated by the working liquid 108. Pressurized air 504 is generated, or any other suitable type of fluid is put under pressure, between the liquid plug (outlet liquid 109) and the closed end (at the closed outlet hole 306) of the outlet channel 105. The amount of displacement of the liquid plug (outlet liquid 109) after termination is indicative of the pressure that would be generated, as a result of the action of the propulsion pump 100 of the present invention, in a microfluidic system connected to the propulsion pump 100.

Figure 7:
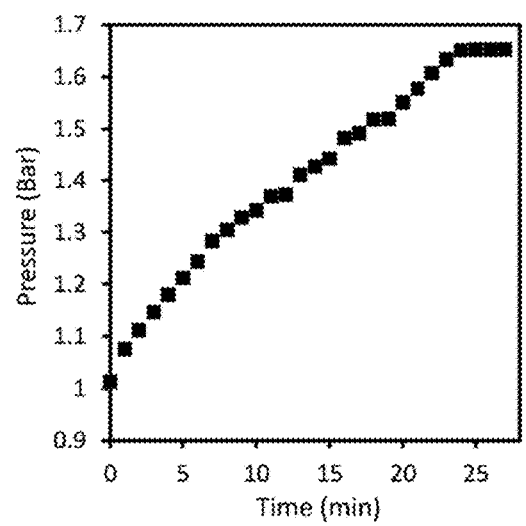
FIG. 7 shows the trend of the pressure building in the device of FIGS. 6(A) to 6(D).

FIG. 7 shows the trend of the pressure building in the device of FIGS. 6(A) to 6(D) as a function of time after the activation of the propulsion pump 100. It can be seen that pressure gradually builds up, up to a particular moment in time, in the embodiment illustrated about 24 minutes, when the pressure levels out. This moment in time corresponds to the time required for all working liquid 108 to be absorbed into the solid sorbent 101 or for the solid sorbent to be saturated by the working liquid 108. Hence the moment in time when the pressure stops building up determines the termination of the pumping action. The time required before the pumping action terminates is a function of the shape and dimensions of the enclosure 102, and/or of the type and amount of solid sorbent material 101 filling the enclosure 102, and/or of the amount of working liquid 108 provided to be brought into contact with the solid sorbent 101.

FIGS. 8(A) to 8(E) illustrate a milli- or microfluidic system 800 comprising a propulsion pump 801 according to embodiments of the present invention, operably connected to a suction pump 802, also called pulling pump, wherein said suction pump 802 serves as an activation means or actuators for said propulsion pump 801.

Figure 8A:
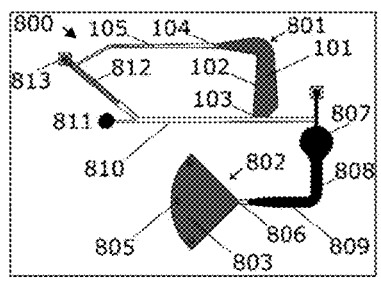
FIGS. 8(A) to 8(E) show an exemplary microfluidic system comprising a suction pump and a propulsion pump according to embodiments of the present invention.

FIG. 8(A), before activation of the propulsion pump 801, the milli- or microfluidic system 800 comprises a suction pump 802 comprising a solid sorbent 803, e.g. porous material, enclosed in a suction pump solid sorbent enclosure 804 in the shape of a circle sector. The solid sorbent 803 of the suction pump 802 contains cavities comprising a fluid. The enclosure 804 of said solid sorbent material 803, e.g. porous material, comprises one or more vent-holes 805 and an opening 806 connecting the enclosure 804 to a reservoir 807, having a flexible or depressible wall, via a channel 808. Said channel 808 and reservoir 807 comprise a working liquid 809. The milli- or microfluidic system 800 furthermore comprises a propulsion pump 801 according to embodiments of the present invention, comprising a solid sorbent 101 enclosed in an enclosure 102. In the embodiment illustrated in FIGS. 8(A) to 8(E), the enclosure 102 is wing-shaped, but the present invention is not limited thereto. That particular wing-shape maximizes the size of the porous material without increasing to much the size of the overall chip. It is, however, not a strict requirement to use such wing-shape, and also for instance the shape of a circular sector, similar as for the suction pump, can be used, the invention not being limited thereto. The channel 808 and reservoir 807 of the suction pump 802 are operably connected to the propulsion pump 801 according to embodiments of the present invention, via a channel 810 (analytical zone) comprising an analyte inlet 811. A droplet of a first liquid analyte is placed on the inlet 811 of the analytical channel 810. The wing-shaped enclosure 102 of the solid sorbent 101 (e.g. porous material) of the propulsion pump 801 comprises a first opening 103 connecting the enclosure 102 to said analytical channel 810, and a second opening 104 connecting to an outlet channel 105. The outlet channel 105 is connected to an analyte storage channel 812, which connects to the analytical channel 810. The analyte storage channel 812 is preloaded with a second liquid analyte via an inlet opening 813 in said channel 812. Immediately after loading the second liquid analyte in said analyte storage channel 812 said inlet opening 813 is sealed.

Figure 8B:
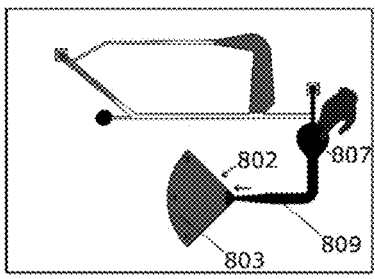

FIG. 8(B), activation of the suction pump 802: the suction pump 802 is activated by applying pressure to the flexible or depressible wall of the reservoir 807, e.g. by compressing the reservoir 807 comprising the working liquid 809, so as to contact the working liquid 809 to the solid sorbent 803 of the suction pump 802, thus initiating the absorption of the working liquid 809 by the solid sorbent of the suction pump 802. Any other actuating means for bringing the working liquid into contact with the solid sorbent, thereby activating the suction pump, can be applied, such as for example opening of a channel or introduction of extra liquid under pressure or the like. While the solid sorbent 803 absorbs working liquid 809, liquid is expelled out of the cavities of the solid sorbent 803 of the suction pump, and is evacuated from the enclosure 804 through the vent-holes 805.

Figure 8C:
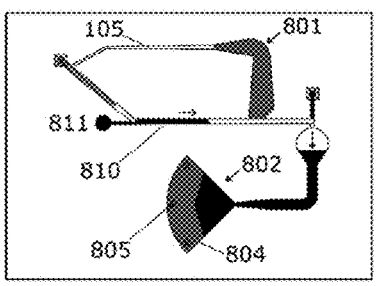

FIG. 8(C), operation of the suction pump 802: as a result of the absorption of the working liquid 809 of the suction pump 802 by the solid sorbent 803 of the suction pump 802, the pressure in the analytical channel 810 is reduced and the first liquid analyte is drawn into in the channel 810.

Figure 8D:
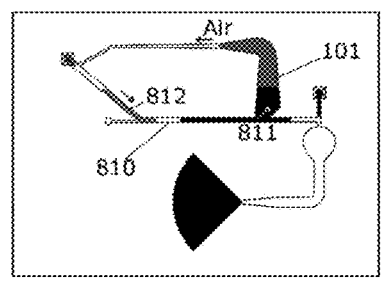

FIG. 8(D), activation of the propulsion pump 801: when the first liquid analyte moving through the channel 810 due to the under-pressure created, contacts the solid sorbent 101, e.g. porous material of the propulsion pump 801, it is absorbed in the solid sorbent 101 and expulses the liquid, e.g. air, from the pores in the solid sorbent 101 into the outlet channel 105. This inflow of the liquid contained in the solid sorbent 101, e.g. air, in the outlet channel 105 pushes the second liquid analyte from said analyte storage channel 812 into the analytical channel 810. The action of the suction pump 802 terminates when all working liquid 809 is absorbed into the solid sorbent of the suction pump 802, or when the solid sorbent of the suction pump 802 is saturated by the working liquid 809. The technical effect of this design with cooperating suction and propulsion pump is that two different fluids sequentially can find a passageway over the same analytical zone.

Figure 8E:
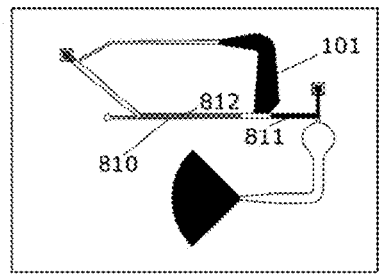

FIG. 8(E), termination of the propulsion pump 801: the pumping operation is terminated either when all first liquid analyte is absorbed into the solid sorbent 101 of the propulsion pump 801 or when the solid sorbent 101 of the propulsion pump 801 is saturated with the first liquid analyte.

FIGS. 9(A) to 9(E) illustrates a further embodiment of a milli- or microfluidic system 900 according to the present invention. The milli- or microfluidic system comprises two propulsion pumps 901, 902 according to embodiments of the present invention, which are operably connected to a suction pump 802, wherein said suction pump 802 serves as an activation means or actuator for said propulsion pumps 901, 902. In this embodiment the suction pump 802 simultaneously activates both propulsion pumps 901, 902. The technical effect of operably connecting two downstream propulsion pumps, preferably equal and opposing propulsion pumps, having their inlet at the same location of the analytical conduit, e.g. analytical channel, according to embodiments of the present invention to an upstream suction pump is that the suction pump when activated by working fluid being sorbed into it and pressure in the analytical conduit, e.g. channel, being reduced that a first fluid, e.g. analyte can be conducted into an analytical zone, where after by activation of the two propulsion pumps two additional fluids are conducted to the same analytical zone and mixed.

Figure 9A:
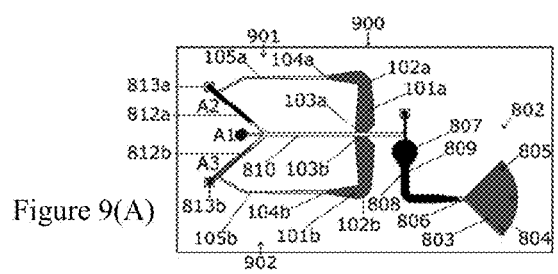
FIGS. 9(A) to 9(E) and FIGS. 10(A) to 10(F) show different exemplary embodiments of a microfluidic system with two propulsion pumps according to embodiments of the present invention, activated with suction pump.

FIG. 9(A), before activation of the propulsion pumps 901, 902, the microfluidic system 900 comprises a suction pump 802 comprising a solid sorbent 803, e.g. porous material, enclosed in an enclosure 804, preferably in the shape of a circle sector. The enclosure 804 of said solid sorbent 803, e.g. porous material, comprises several vent-holes 805 and an opening 806 connecting the enclosure 804 of the suction pump 802 to a reservoir 807 via a channel 808, wherein said reservoir 807 has a flexible or depressible wall. Said channel 808 and reservoir 807 comprise a working liquid 809. The milli- or microfluidic system 900 furthermore comprises a first propulsion pump 901 according to embodiments of the present invention, and a second propulsion pump 902 according to embodiments of the present invention. The first and second propulsion pumps 901, 902 comprise a solid sorbent 101a, 101b, enclosed in an enclosure 102a, 102b, respectively. In the embodiment illustrated in FIGS. 9(A) to 9(E), the enclosures 102a, 102b are wing-shaped, but the present invention is not limited thereto. The channel 808 and reservoir 807 are operably connected to the first propulsion pump 901 and to the second propulsion pump 902, via a channel 810 (analytical zone) comprising an analyte inlet 811. A droplet of a first liquid analyte is placed on the inlet 811 of the analytical channel 810. The enclosures 102a, 102b of the preferably wing-shaped solid sorbents 101a, 101b (e.g. porous material) of the propulsion pumps 901, 902 each comprise a first opening 103a, 103b connecting the enclosures 102a, 102b, respectively, to said analytical channel 810, wherein said openings 103a, 103b are positioned at a same position along said analytical channel 810 but at opposite sides thereof. Each of said enclosures 102a, 102n of the preferably wing-shaped solid sorbent material 101a, 101b further comprises a second opening 104a, 104b connecting each of said enclosures 102a, 102b to a separate outlet channel 105a, 105b. Each of said outlet channels 105a, 105b is connected to a separate analyte storage channel 812a, 812b, which each connect to the analytical channel 810 at a same position along the analytical channel 810 but at opposite sides thereof. These analyte storage channels 812a, 812b are preloaded with a second and third liquid analyte A2, A3, respectively, via the inlet openings 813a, 813b in each of these channels 812a, 812b. Immediately after loading second and third liquid analyte into the storage channels 812a, 812b, said inlet openings 813a, 813b are sealed.

Figure 9D:
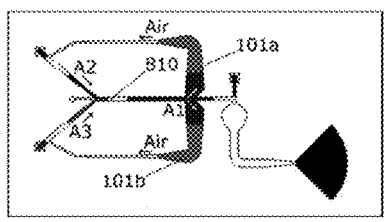
Figure 9B:
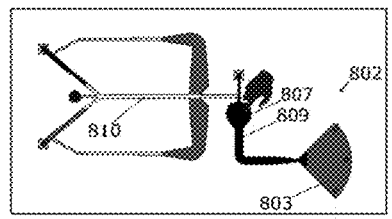

FIG. 9(B), activation of the suction pump 802: the suction pump 802 is activated by applying a force on, e.g. by compressing, the flexible or depressible wall of the reservoir 807 comprising the working liquid 809, thus bringing the working liquid 809 into contact with the solid sorbent 803 of the suction pump 802 and initiating the absorption of the working liquid 809 by the solid sorbent 803 of the suction pump 802.

Figure 9E:
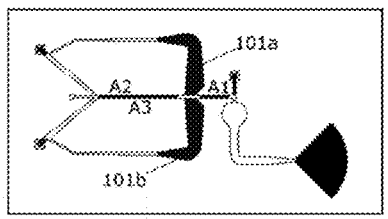
Figure 9C:
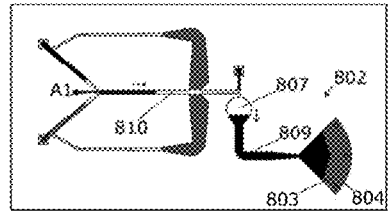

FIG. 9(C), operation of the suction pump 802: as a result of the absorption of the working liquid 809 by the solid sorbent 803 of the suction pump 802, the pressure in the analytical channel 810 is reduced and first liquid analyte is drawn into this channel 810.

FIG. 9(D), activation of the propulsion pumps 901, 902: when the first liquid analyte A1 contacts the solid sorbent materials 101a, 101b, e.g. porous materials, of the respective propulsion pumps 901, 902, it is simultaneously absorbed by the solid sorbent materials 101a, 101b, and expulses the liquid, e.g. air, from the pores in both the solid sorbent materials 101a, 101b, into the respective outlet channels 105a, 105b. These air inflows in the respective outlet channels 105a, 105b simultaneously push the second liquid analyte A2 and the third liquid analyte A3 from their analyte storage channels 812a, 812b into the analytical channel, where they can mix. The action of the suction pump 802 terminates when all working liquid 809 is absorbed into the solid sorbent 803 of the suction pump 802, or when the solid sorbent 803 o the suction pump 802 is saturated with the working liquid 809. Preferably, the design of the microfluidic system 900 is such that the action of the suction pump 802 terminates upon activation or shortly after activation of the propulsion pumps 901, 902.

FIG. 9(E), termination of the propulsion pumps 901, 902: the operation of each of the propulsion pumps 901, 902 terminates as soon as either the first liquid analyte A1 is absorbed by the solid sorbents 101a, 101b, or when the solid sorbents 101a, 101b are saturated with the first liquid analyte A1.

FIGS. 10(A) to 10(F) illustrate another milli- or microfluidic system 1000 according to embodiments of the present invention. The milli- or microfluidic system 1000 comprises two propulsion pumps 1001, 1002 according to embodiments of the present invention operably connected to a suction pump 802, wherein said suction pump 802 serves as an activation means or actuators for said propulsion pumps 1001, 1002. In this embodiment the suction pump 802 sequentially activates the propulsion pumps 1001, 1002. This is obtained by, opposite to the embodiment illustrated in FIGS. 9(A) to 9(E), not having the inlet of the propulsion pumps 1001, 1002 at the same location of the analytical channel 810.

Figure 10A:
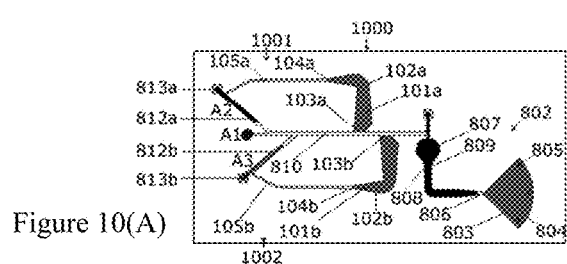

FIG. 10(A), before activation of the propulsion pumps 1001, 1002, the microfluidic system 1000 comprises a suction pump 802 comprising a solid sorbent 803 enclosed in an enclosure 804, preferably in the shape of a circle sector. The enclosure 804 of the solid sorbent 803 of the suction pump 802 comprises one or more vent-holes 805 and an opening 806 connecting the enclosure 804 to a reservoir 807 via a channel 808, wherein said reservoir 807 has a flexible or depressible wall. Said channel 808 and reservoir 807 comprise a working liquid 809 and are operably connected to a plurality of, in the example illustrated two, propulsion pumps 1001, 1002 according to embodiments of the present invention, via a channel 810 (analytical zone) comprising an analyte inlet. A droplet of a first liquid analyte A1 is placed on the inlet 811 of the analytical channel 810. The enclosures 102a, 102b of the preferably wing-shaped solid sorbents 101a, 101b of the propulsion pumps 1001, 1002 each comprise a first opening 103a, 103b connecting the respective enclosures 102a, 102b to said analytical channel 810, wherein said openings 103a, 103b are positioned at different positions along said analytical channel 810 and at opposite sides thereof. Each of said enclosures 102a, 102b of the preferably wing-shaped solid sorbents 101a, 101b, e.g. porous material, further comprises a second opening 104a, 104b connecting each of said enclosures 102a, 102b to a separate outlet channel 105a, 105b. Each of said outlet channels 105a, 105b is connected to a separate analyte storage channel 812a, 812b, which each connect to the analytical channel 810 at different positions along the analytical channel 810 and at opposite sides thereof. These analyte storage channels 812a, 8112b are preloaded with a second and third liquid analyte A2, A3 via the inlet openings 813a, 813b in each of these channels 812a, 812b. Immediately after loading the second liquid analyte A2 and the third liquid analyte A3 into the storage channels 812a, 8112b said inlet openings 813a, 813b are sealed.

Figure 10D:
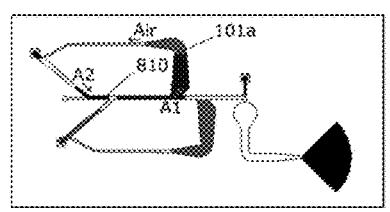
Figure 10B:
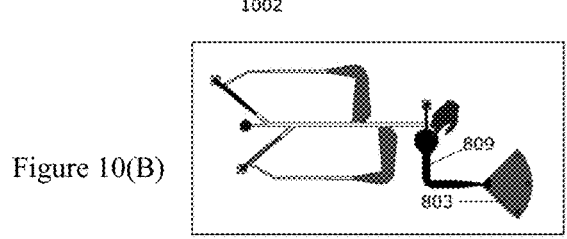

FIG. 10(B), activation of the suction pump 802: the suction pump 802 is activated by applying pressure to, e.g. by compressing, the flexible or depressible wall of the reservoir 807 comprising the working liquid 809, thus bringing the working liquid 809 into contact with the solid sorbent 803 of the suction pump, thus initiating the absorption of the working liquid 809 by the solid sorbent 803.

Figure 10E:
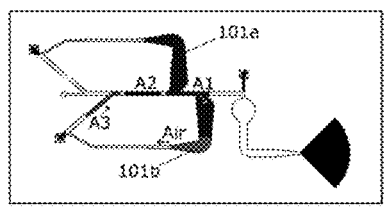
Figure 10C:
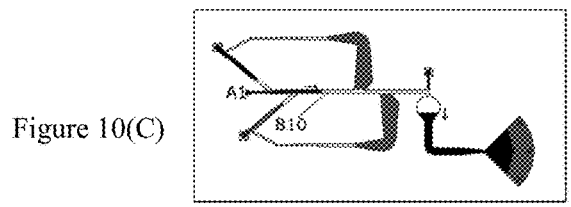

FIG. 10(C), operation of the suction pump 802: as a result of the absorption of the working liquid 809 by the solid sorbent 803 of the suction pump 802 the pressure in the analytical channel 810 is reduced and first liquid analyte A1 is drawn into this channel 810.

FIG. 10(D), activation of the first propulsion pump 1001: when first liquid analyte A1 contacts the solid sorbent 101a, e.g. porous material, positioned most upstream relative to the flow of the first liquid analyte A1, it is absorbed and expulses the liquid, e.g. air, from the pores in the solid sorbent 101a of the first propulsion pump 1001 into the outlet channel 105a connected to the enclosure 102a of the solid sorbent 101a. This fluid flow, e.g. air inflow, in said outlet channel 105a subsequently pushes second liquid analyte A2 from its analyte storage channel 812a into the analytical channel 810. The action of the suction pump 802 terminates when all working liquid 809 is absorbed into the solid sorbent 803 of the suction pump 802, or when the solid sorbent 803 is saturated with the working liquid 809.

FIG. 10(E), activation of the second propulsion pump 1002: the activation of the first propulsion pump 1001 results in the flow of part of the first liquid analyte A1 further downstream into the analytical channel 810 until A1 contacts the solid sorbent material 101b, e.g. porous material, by which it is absorbed leading to the expulsion of fluid, e.g. the air, from the pores in the solid sorbent material 101b of the second propulsion pump 1002 into the outlet channel 105b connected to the enclosure 102b of the solid sorbent material 101b. This fluid flow, e.g. air inflow, in said outlet channel 105b subsequently pushes third liquid analyte A3 from its analyte storage channel 812b into the analytical channel 810. The operation of the first propulsion pump 1001 terminates as soon as the solid sorbent material 101a of the first propulsion pump 1001 is saturated with the first liquid analyte A1.

Figure 10F:
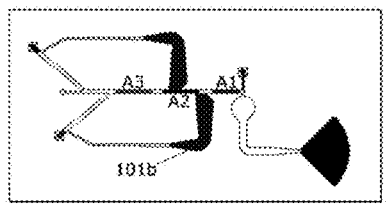

FIG. 10(F), termination of the second propulsion pump 1002: the operation of the second propulsion pump 1002 is similar to the operation of the first propulsion pump 1001, and terminates as soon as either the first liquid analyte A1 is absorbed by the solid sorbent of the second propulsion pump 1002, or when the solid sorbent of the second propulsion pump 1002 is saturated with the first liquid analyte A1.

The technical effect of operably connecting two downstream propulsion pumps, preferably equal and opposing propulsion pumps, having their inlet at a different location of the analytical conduit, e.g. analytical channel, according to embodiments of the present invention to an upstream suction pump is that the suction pump when activated by working fluid being sorbed into it and pressure in the analytical conduit, e g channel, being reduced that a first fluid, e.g. analyte can be conducted into an analytical zone, where after when a first propulsion pumps is activated that conduits a second preloaded fluid to and into the same analytical zone and consequently when the second propulsion pumps is activated that conduits a third preloaded fluid to and into the same analytical zone.

FIGS. 11(A) to 11(E) illustrate a microfluidic system 1100 comprising a suction pump 1102 being activated by a propulsion pump 1101 according to embodiments of the present invention, wherein said propulsion pump 1101 simultaneously acts as a suction pump.

Figure 11A:
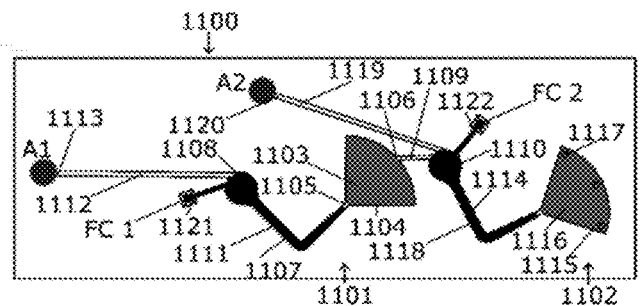
FIGS. 11(A) to 11(E) show an embodiment of a microfluidic system comprising a suction pump being activated by a propulsion pump.

FIG. 11(A), before activation, the microfluidic system 1100 comprises a first, preferably circular sector shaped, solid sorbent 1103 enclosed in a first enclosure 1104. The first enclosure 1104 of solid sorbent 1103 comprises a first opening 1105 and a second opening 1106, wherein said first opening 1105 connects via a first channel 1107 to a first reservoir 1108 having a flexible or depressible wall and said second opening 1106 connects via a second channel 1109 to a second reservoir 1110. Said first channel 1107 and first reservoir 1108 comprise a first working liquid 1111, and said first reservoir 1108 connects to a first analytical channel 1112 comprising an inlet opening on which a drop of a first liquid analyte A1 may be deposited. Said second reservoir 1110 is further connected to a third channel 1114 leading to a second enclosure 1115 comprising a second solid sorbent 1116, wherein said second enclosure 1115 comprises one or more vent-holes 1117. Said third channel 1114 and second reservoir 1110 comprise a second working liquid 1118. In addition, said second, preferably circular sector shaped, reservoir 1110 is connected to a second analytical channel

1119, at the inlet opening 1120 of which a drop of a second liquid analyte A2 may be deposited. The first working liquid 1111 and the second working liquid 1118 are fed into said first reservoir 1108 and second reservoir 1110, respectively, via the first filling channel 1121 and second filling channel 1122. The inlet openings 1123, 1124 of the first and second filling channels 1121, 1122 are sealed immediately after filling the channels.

Figure 11B:
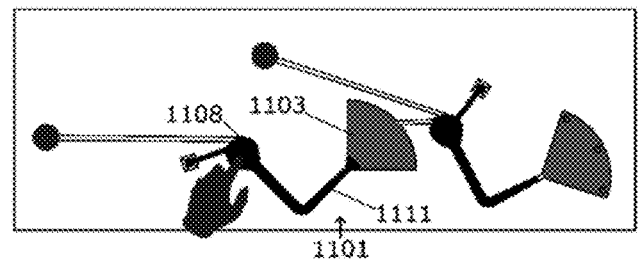

FIG. 11(B), activation of the propulsion/suction pump 1101: the propulsion/suction pump 1101 is activated by compressing the flexible or depressible wall of the first reservoir 1108, thus bringing the first working liquid into contact with the first solid sorbent 1103 and initiating the absorption of the first working liquid 1111 by the first solid sorbent 1103.

Figure 11C:
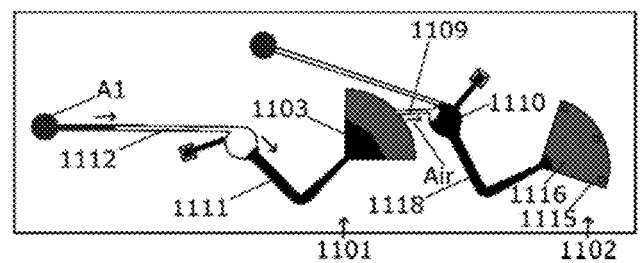

FIG. 11(C), operation of the propulsion/suction pump 1101 and activation of the suction pump 1102: as a result of the absorption of the first working liquid 1111 by the first sorbent 1103 (e.g. a solid sorbent), the pressure in the first analytical channel 1112 is reduced, and first liquid analyte A1 is drawn into this channel 1112. At the same time the first working liquid 1111 expulses the fluid, e.g. the air, contained in the cavities, e.g. pores, of the first solid sorbent 1103 into said second reservoir 1101 via the second channel 1109. The fluid, e.g. air, inflow into said second reservoir 1110 pushes the second working liquid 1118 into the second enclosure 1115 enclosing the second solid sorbent 1116, resulting in the second working liquid 1118 contacting the second solid sorbent 1116 and thus activating the suction pump 1102.

Figure 11D:
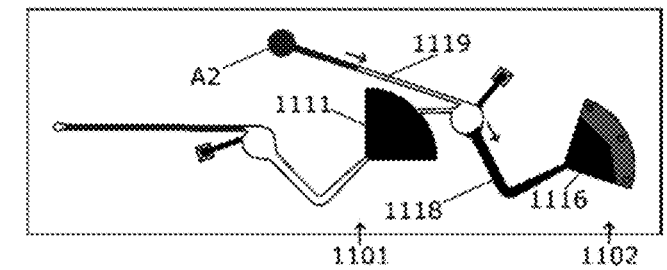

FIG. 11(D), operation of the suction pump 1102 and termination of the propulsion/suction pump 1101: Upon contact of the second working liquid 1118 with the second solid sorbent 1116, the absorption of the second working liquid 1118 results in a reduction of pressure in the second analytical channel 1119, and second analytical liquid A2 is drawn into the second analytical channel 1119. The action of the propulsion/suction pump 1101 terminates as soon as the first working liquid 1111 is absorbed by the first solid sorbent 1103 or when the first solid sorbent 1103 is saturated with the first working liquid 1111.

Figure 11E:
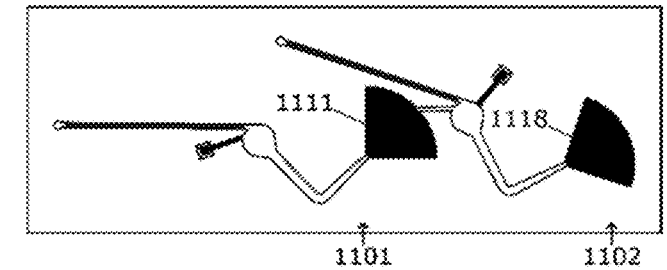

FIG. 11(E), termination of the suction pump 1102: The action of the suction pump 1102 terminates when all second working liquid 1118 is absorbed by the second solid sorbent 1116 or when the second solid sorbent 1116 is saturated with the second working liquid 1118.

Figure 12A:
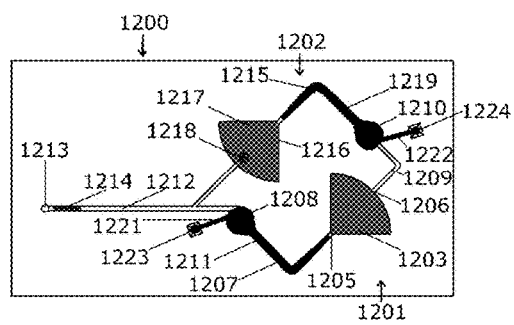
FIGS. 12(A) to 12(F) show a microfluidic system comprising two propulsion pumps according to the present invention.

FIGS. 12(A) to 12(F) illustrate a milli- or microfluidic system 1200 comprising two propulsion pumps 1201, 1202 according to embodiments of the present invention wherein one propulsion pump 1201 acts as an activating pump for activating the other propulsion pump 1202, and wherein said activating pump 1201 also acts as a suction pump. FIG. 12(A), before activation, the microfluidic system 1200 comprises a first, preferably circular sector shaped, solid sorbent 1203 enclosed in a first enclosure 1204. The first enclosure 1204 of first solid sorbent 1203 comprises a first opening 1205 and a second opening 1206, wherein said first opening 1205 connects via a first channel 1207 to a first reservoir 1208 having a flexible or depressible wall, and said second opening 1206 connects via a second channel 1209 to a second reservoir 1210. Said first channel 1207 and first reservoir 1208 comprise a first working liquid 1211 and said first reservoir 1208 connects to an analytical channel 1212 comprising an inlet opening 1213 through which a liquid plug 1214 is introduced, to be present in the vicinity of said inlet opening 1213. Said second reservoir 1210 is further connected to a third channel 1215 leading to a second enclosure 1216 comprising a second, preferably sector shaped, solid sorbent 1217, wherein said second enclosure 1216 comprises one or more vent-holes 1218. Said third channel 1215 and second reservoir 1210 comprise a second working liquid 1219. The second enclosure 1216 enclosing the second solid sorbent 1217 further connects via a fourth channel 1220 with the analytical channel 1212. Said fourth channel 1220 connects with the analytical channel 1212 at a position closer to the inlet 1213 of the analytical channel 1212 than the position of the connection between the analytical channel 1212 and the first reservoir 1208. The first working liquid 1211 and the second working liquid 1219 are fed into said first and second reservoirs 1208, 1210, respectively, via the first and second filling channels 1221 and 1222. The inlet openings 1223, 1224 of the first and second filling channels 1221 and 1222, respectively, and the vent-hole 1218 in the second enclosure 1216 enclosing the second solid sorbent 1217 are sealed, preferably immediately after filling the channels 1207, 1215 and the introduction of the liquid plug 1214.

Figure 12D:
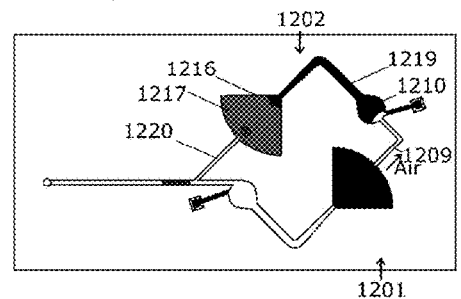
Figure 12B:
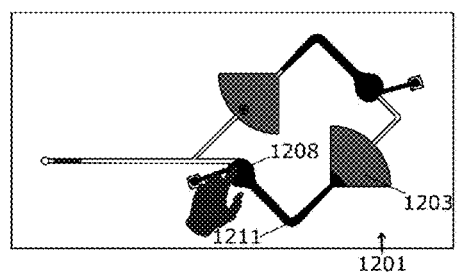

FIG. 12(B), activation of the first propulsion/suction pump 1201: the first propulsion/suction pump 1201 is activated by applying pressure to, e.g. by compressing, the flexible or depressible wall of the first reservoir 1208, thus bringing the first working liquid 1211 into contact with the first solid sorbent 1203 and initiating the absorption of the first working liquid 1211 by the first solid sorbent 1203.

Figure 12E:
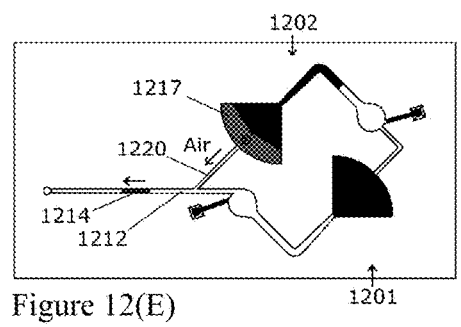
Figure 12C:
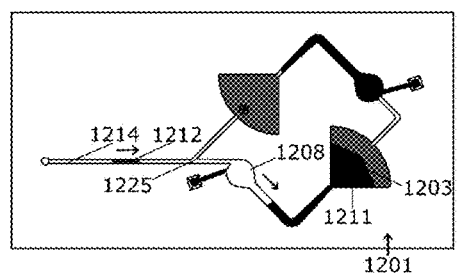

FIGS. 12(C) and 12(D), operation of the propulsion/suction pump 1201 and activation of the second propulsion pump 1202: as a result of the absorption of the first working liquid 1211 by the first solid sorbent 1203, the pressure in the analytical channel 1212 is reduced and the liquid plug 1214 is drawn further into this channel 1212. Typically, the microfluidic system 1200 is designed such that the liquid plug 1214 is not drawn into the analytical channel 1212 beyond the connection 1225 between the analytical channel 1212 and said fourth channel 1220. At the same time, the first working liquid 1211 expulses the fluid, e.g. air, contained in the cavities, e.g. pores, of the first solid sorbent 1203 into said second channel 1209 connected to said second reservoir 1210. The fluid, e.g. air, inflow into said second reservoir 1210 pushes the second working liquid 1219 into the second enclosure 1216 enclosing the second solid sorbent 1217, resulting in the second working liquid 1219 contacting the second solid sorbent 1217 and thus activating the second propulsion pump 1202.

FIG. 12(E), operation of the second propulsion pump 1202 and termination of the first propulsion/suction pump 1201: Upon contact of the second working liquid 1219 with the second solid sorbent 1217, the absorption of the second working liquid 1219 results in an expulsion of fluid, e.g. air, from the cavities, e.g. pores, in the second solid sorbent 1217 via said fourth channel 1220 into the analytical channel 1212. This fluid, e.g. air, flow into the analytical channel 1212 pushes the liquid plug 1214 back towards the inlet opening 1213 of the analytical channel 1212. The action of the propulsion/suction pump 1201 terminates as soon as the first working liquid 1211 is absorbed by the first solid sorbent 1203 or when the first solid sorbent 1203 is saturated with the first working liquid 1211. Preferably, the design of the microfluidic system 1200 is such that the action of first propulsion/suction pump 1201 terminates upon activation or shortly after activation of the second propulsion pump 1202.

Figure 12F:
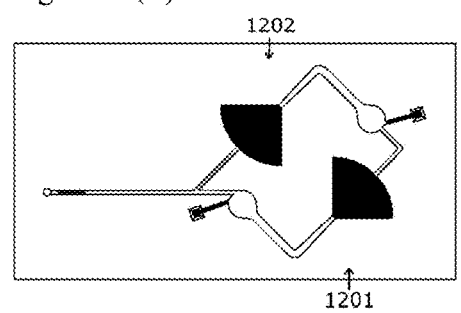

FIG. 12(F), termination of the second propulsion pump 1202: The action of the second propulsion pump 1202 terminates when all second working liquid is absorbed by the second solid sorbent 1217 or when the second solid sorbent 1217 is saturated with the second working liquid 1219.

FIGS. 13(A) to 13(F) illustrate an assay system 1300, comprising a suction and propulsion pump combination in accordance with embodiments of the present invention, for example for use in a 3 steps protocol with two reagents mixing and washing steps. The design and parts of the suction and propulsion pumps, and the activation and operation steps of the suction and propulsion pumps, are similar as described above, and are not repeated here in as many details as above. Reference for further details is made to the description hereinabove.

Figures 13A, 13B, 13C, 13D, 13E, 13F:
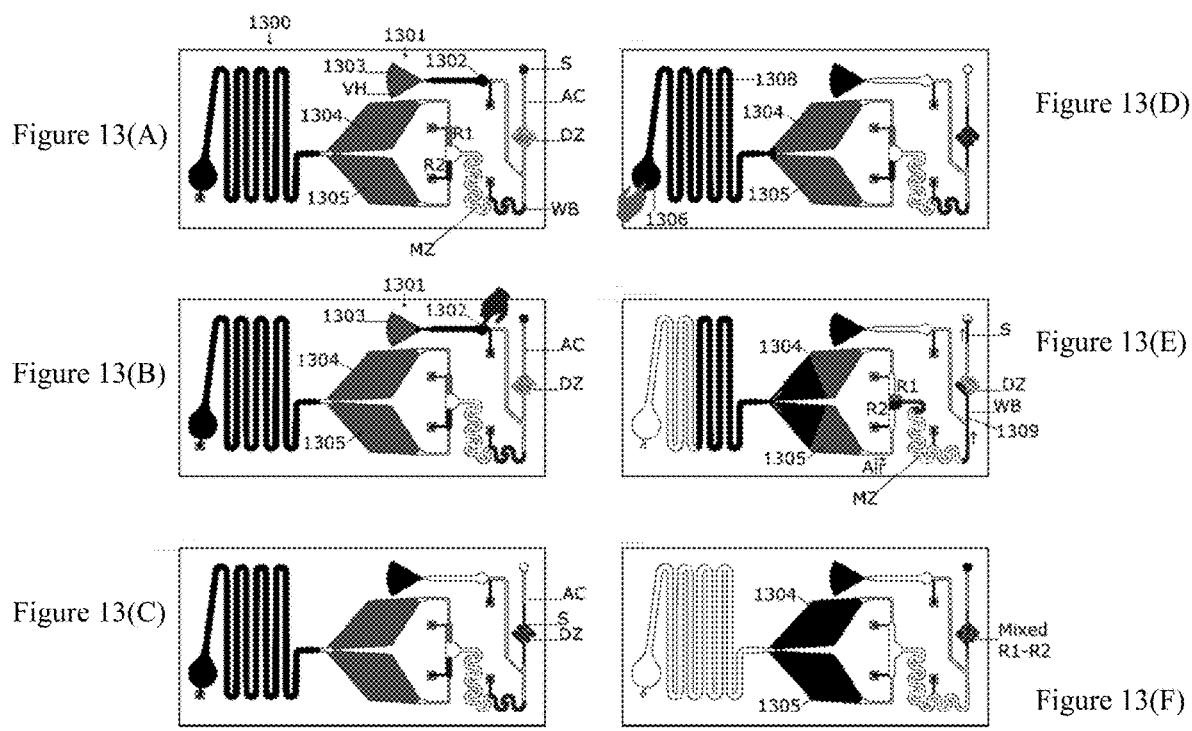
FIGS. 13(A) to 13(F) show an assay system comprising a suction and propulsion pump combination.

FIG. 13(A), initiation: a first working liquid WL1, a second working liquid WL2), a first reagent R1, a second reagent R2 and washing buffer WB are preloaded in the respective chambers while a droplet of sample S is placed on the inlet of analytical channel AC. In the analytical channel AC, a detection zone DZ (pre-functionalized with receptors) is present to capture the analyte present in the sample S. FIG. 13(B), activation of suction pump 1301: suction pump 1301 is activated by applying a pressure to a first reservoir 1302 connected via a first channel 1307 to a first enclosure 1303 comprising first solid sorbent PM1. A first working liquid WL1 was contained in the first reservoir and the first channel 1307, and applying the pressure to the first reservoir 1302 causes the first working liquid WL1 to be absorbed by the first solid sorbent PM1, e.g. porous material, provided in the first enclosure 1303. FIG. 13(C), operation of suction pump 1301: the absorption of the first working liquid WL1 by the first solid sorbent PM1, generates a reduced pressure in the analytical channel AC, which draws the sample S in the analytical channel AC over the detection zone DZ. After that, the operation of the suction pump 1301 is terminated. FIG. 13(D), activation of the propulsion pumps 1304, 1305: Two propulsion pumps 1304, 1305 are connected in parallel, both being connected with their input opening to a same inlet channel 1308, which at its other end is connected to a second reservoir 1306. The second reservoir 1306 and the inlet channel 1308 are filled with a second working liquid WL2, which before activation of the propulsion pumps 1304, 1305 does not reach the second and third solid sorbents PM2, PM3 in the respective propulsion pumps 1304, 1305. The propulsion pumps 1304, 1305 are activated by applying a pressure to a flexible or depressible wall of the second reservoir 1306, and the second working liquid WL2 starts getting absorbed by the second and third solid sorbents PM2, PM3, e.g. porous material, of the propulsion pump circuits, respectively. FIG. 13(E), the second working liquid WL2 gets absorbed more and more, and pushes out the fluid, e.g. air, present in the cavities of the second and third solid sorbents PM2 and PM3. This fluid, e.g. air, pushes the first and second reagents R1 and R2, present in output channels of the first and second propulsion pumps 1304, 1305, simultaneously into a mixing zone MZ where they mix. At the same time, the washing buffer WB, present in a further channel 1309 between the mixing zone MZ and the detection zone DZ, is pushed over the detection zone DZ, thus replacing the sample S. The propulsion pumps 1304, 1305 continue their action, and while more and more fluid, e.g. air, is pushed out of the cavities in the second and third solid sorbents PM2, PM3, the mixed reagents R1+R2 are moved from the mixing zone MZ, through the further channel 1309 to the detection zone DZ. FIG. 13(F), termination propulsion pumps 1304, 1305: When the mixed first reagent R1 and second reagent R2 are moved over the detection DZ, the system stops due to complete absorption of the second working liquid WL2 into the second solid sorbent PM2 and into the third solid sorbent PM3 or due to complete saturation of the second solid sorbent PM2 and the third solid sorbent PM3. The exact moment of stopping of the action of the system can be tuned by tuning design parameters of the systems, e.g. dimensions of the solid sorbents and/or the cavities containing these, lengths of channels, etc.

Figure 14:
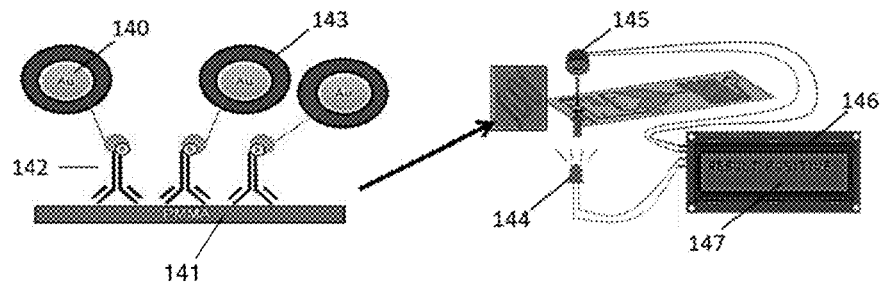
FIG. 14 shows a detection system for use in a microfluidic bioassay.

FIG. 14 illustrates a detection system for use in a microfluidic bioassay. The illustrated embodiment is based on the capturing of gold nanoparticles 140 functionalized with streptavidin on a surface 141 pre-functionalized with biotinylated antibodies 142, but of course this is an example only, and the invention is not limited thereto but is much broader applicable in other applications as well. In order to generate a signal that can be detected with bare eyes (for qualitative detection, i.e. yes/no) or with a photodiode (for semi-quantitative detection), a silver enhancement 143 was performed. Silver solution (made of mixed reagent 1 and reagent 2) was brought over the detection zone, and catalyzed by the gold nanoparticles 140, it forms an opaque dark layer. For semi-quantitative detection, an electrical circuit comprising a light source such as a LED 144, a photodiode 145 and a microcontroller 146 was used to measure the intensity loss of light due to reflection on the silver layer. Only the light that passes through was picked up by the photodiode 145 and this information was processed by the microcontroller 146, which then displayed the result of the test on an LCD screen 147. So the less light the photodiode 145 received, the darker and thicker the silver layer is, due to higher concentration of gold nanoparticles 140. The detection system of this FIG. 14 can for instance be used in the assay system according to example 11 below, wherein the detection zone is coated with biotinylated antibodies 142.

FIGS. 15(A) to 15(D) illustrate an assay system 1500 for use in a microfluidic bioassay involving, as an example, a coupled enzyme reaction, which results in a colorimetric product. This assay system 1500 comprises two propulsion pumps 1501, 1502 and means for diluting and mixing a sample within the assay solution. The design and parts of the propulsion pumps, and the activation and operation steps of the propulsion pumps, are similar as described above, and are not repeated here in as many details as above. Reference for further details is made to the description hereinabove.

Figure 15A:
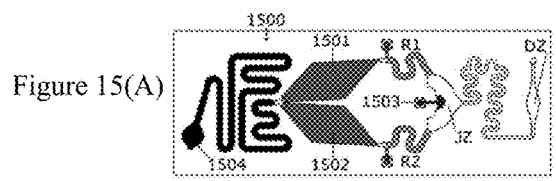
FIGS. 15(A) to 15(D) show an assay system for use in a microfluidic bioassay involving a coupled enzyme reaction.
Figure 15C:
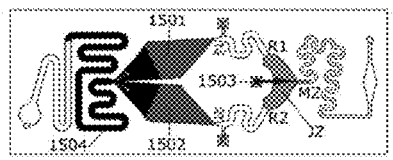
Figure 15B:
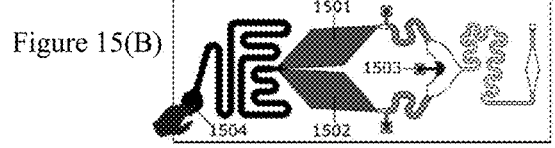
Figure 15D:
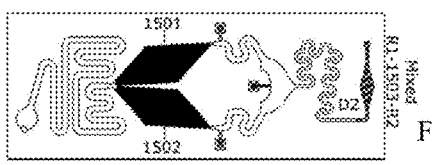

FIG. 15(A), initiation: A reservoir 1504 is connected via an inlet channel 1505 to the input side of two parallel propulsion pumps 1501, 1502. Working liquid WL, first reagent R1, and second reagent R2 are preloaded in the respective chambers while a sample S is pipetted in a junction zone JZ through an inlet hole 1503 which is subsequently sealed. The reservoir 1504 and the inlet channel 1505 are filled with working liquid WL, such that the working liquid WL does not reach the solid sorbent of the propulsion pumps 1501, 1502. FIG. 15(B), activation: the propulsion pumps 1501, 1502 are activated by applying a pressure to a flexible or depressible wall of the reservoir 1504, which brings the working liquid WL into contact with the solid sorbent materials PM1, PM2, e.g. porous materials, in the first and second propulsion pumps 1501, 1502. Once brought into contact, this is followed by the absorption of the working liquid WL by the solid sorbents, e.g. porous materials. FIG. 15(C), this absorption of the working liquid WL results into the expulsion of the fluid, e.g. air, present in solid sorbents PM1 and PM2 into the microfluidic chambers comprising the first and second reagents R1 and R2, respectively. The expulsed fluid, e.g. air, drives the first and second reagent R1 and R2 simultaneously into the junction zone JZ where they dilute the sample S previously provided. The diluted sample is further mixed with the first and second reagents R1 and R2 while passing the mixing zone (MZ). FIG. 15(D), termination: When the fluid comprising the combined first reagent R1, sample S and second reagent R2 fills the detection zone DZ, the pump system stops due to complete absorption of working liquid WL into the solid sorbents PM1 and PM2 of the propulsion pumps 1501, 1502, or due to complete saturation of the solid sorbents PM1 and PM2 with the working liquid WL. Depending of the concentration of the analyte of interest, the enzyme coupled reaction shall generate more or less of a colorimetric product. The presence of the colorimetric product can be measured in the detection zone DZ in any suitable way, for instance using a spectrophotometer. It is preferred that the detection zone DZ has an higher height than the other parts of the network to ensure a sufficient path length for spectrophotometric detection.

Figure 16A:
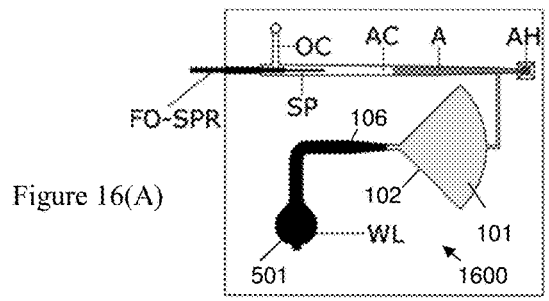
FIGS. 16(A) to 16(D) illustrate a further embodiment of the present invention, in which a surface plasmon resonance optical fiber is integrated with a propulsion pump according to embodiments of the present invention, in a system or chip, for data readout.

FIGS. 16(A) to 16(D) illustrate a fiber optic surface plasmon resonance sensor integrated with a milli- or microfluidic propulsion pump, according to further embodiments of the present invention. FIG. 16(A), prior to its activation the propulsion pump 1600 comprises a solid sorbent 101 (porous material) enclosed in an enclosure 102, preferably in the shape of a circle sector. The enclosure 102 is connected to an inlet channel 106 and to an analytical channel AC. The inlet channel 106 is further connected to an inlet reservoir 501 having a flexible or depressible wall, wherein the inlet reservoir 501 and the inlet channel 106 contain a working liquid WL. Analyte A is filled through an analyte hole AH in the analytical channel AC before a measurement starts. Once this is done, the analyte hole AH is sealed. A fiber-optic surface plasma resonance (FO-SPR) probe SP is inserted in the analytical channel AC of the propulsion pump, until the sensing part overcomes the outlet channel OC intersection. The FO-SPR sensor setup consists of a white light source, a spectrophotometer, a bifurcated optical fiber and sensor probes. The bifurcated fiber guides white light to the sensor tip where it is reflected back to the spectrometer. The sensor tip is covered with a gold layer. As the light interacts with the surface of the optical fiber, an SPR is generated in this gold layer. A binding event on the outside of the gold layer disturbs prosthesis surface plasmons, changing the resonance conditions and shifts hence the resonance wavelength. This detection principle allows many biochemical interactions to be monitored in real time.

Figure 16B:
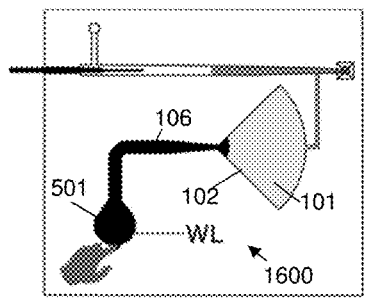
Figure 16C:
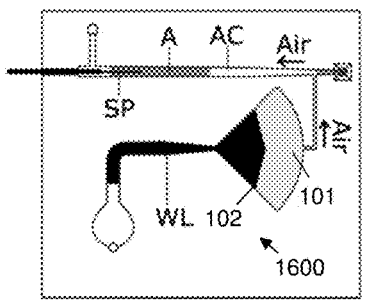
Figure 16D:
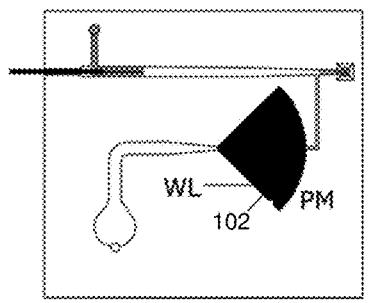

FIG. 16(B), activation: the propulsion pump 1600 is activated by applying a pressure to, e.g. by compressing, the flexible or depressible wall of the inlet reservoir 501 connected to the inlet channel 106, thus moving the working liquid WL in the inlet channel 106 so that it contacts the solid sorbent 101 leading to the absorption of the working liquid WL by the solid sorbent 101. FIG. 16(C) operation: while the working liquid WL is absorbed into the solid sorbent 101, it expulses the fluid, for example air, present in the cavities in the solid sorbent 101 into the analytical channel AC. This fluid influx in the analytical channel AC pushes the analyte A further into the channel AC around the probe of the fiber optic surface plasma resonance detector FO-SPR downstream of the analytical channel AC, for being measured. FIG. 16(D), termination: the action of the pump 1600 is terminated either when all the working liquid WL is absorbed into the solid sorbent 101 or when the solid sorbent 101 is saturated by the working liquid WL.

In order to satisfy the need for microfluidic systems connected to needles or microneedles for drug delivery, microfluidic systems according to embodiments of the present invention can be used. These have the capability to deliver smaller volumes than mechanical fluidic syringe systems and furthermore that microfluidics systems of present invention have the ability to more precisely control flow rates if actuated for pumping of fluids to outlet by a solid sorbent based milli- or microfluidic propulsion pump. Such milli- or microfluidic propulsion pump comprising a solid sorbent enclosed in an enclosure, said solid sorbent is contained in a cavity comprising a first opening through which said solid sorbent can be contacted with a liquid and a second opening connecting the enclosure to an outlet channel.

Different arrangements of the channels and capillary pumps may provide different functionalities. For example, in case of propulsion pumps, the capillary pump may be connected to a conduit downstream for pushing fluid, or in case of a pulling pump, to a vent-hole directly provided on the enclosure of the solid sorbent of the capillary pump or to a unit with a vent hole downstream of the capillary pump or the like. A capillary pump may also serve as actuator of further pumps.

The milli- or microfluidic propulsion pump have particular advantages towards actuators of the art, which are typically based on electrical, magnetic, mechanical (spring), or gas pressure systems and need usually external sources of energy or rely on mechanical movable parts, which are prone to malfunction.

Figure 17C:
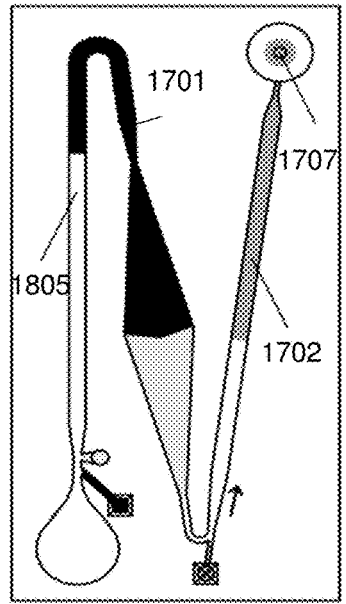
FIGS. 17(A) to 17(D) are a graphic that displays the propulsion pump (so called iSIMPLE) of present invention for drug delivery with hydrophobic valve.
Figure 17D:
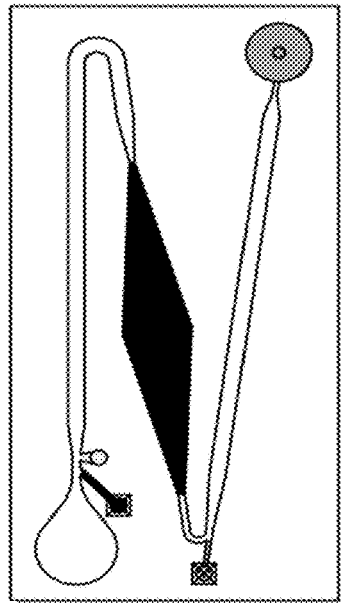
Figure 17A:
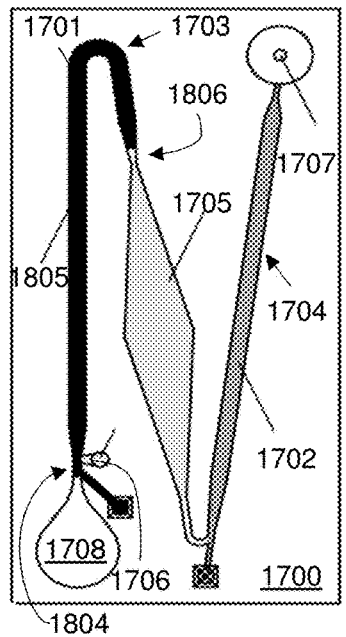
Figure 17B:
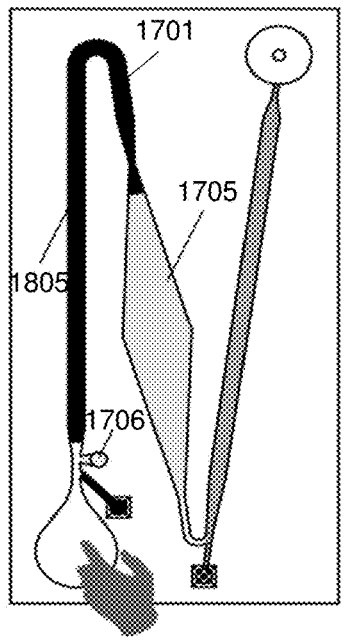

FIGS. 17(A) to 17(D) are a graphic that displays the propulsion pump 1700 (so called iSIMPLE) of present invention for drug delivery with hydrophobic valve. FIG. 17(A), initiation: working liquid (WL) 1701 and outlet liquid (OL) 1702 are preloaded in the respective chambers, zones or channels 1703, 1704 while a porous material (PM) 1705 was housed in its chamber during the fabrication. In particular, the WL chamber 1703 acts as a second conduit zone. A hydrophobic valve (HV) 1706 comprising a filter paper treated to become hydrophobic, was positioned on a side of the WL chamber 1703 after the WL prefilling point. The other side of the HV 1706 is open to the air. A needle or microneedle 1707 is coupled to the outlet of the outlet channel 1704. FIG. 17(B), activation: pushing on the activation zone 1708, the WL 1701 gets in contact with the PM 1705 and overcome the HV 1706 interface with the WL chamber 1703. In other words, the volume of fluid in the first conduit zone 1804 is pushed forward, forcing the WL of the second conduit zone (WL chamber 1703) into the third conduit zone 1806, surpassing it and making the WL contact the capillary pump. The volume of the first conduit zone 1804 is determined by the volume between the inlet of the WL and the position of the hydrophobic valve 1706, and it must be such that it ensures that the WL can surpass the third conduit zone 1806. FIG. 17(C), operation: while the WL 1701 is absorbed into the PM 1705 (which acts as a solid sorbent), it pushes out the air present in the PM 1705. This air pushes the OL 1702 out of the needle/microneedle 1707. The HV 1706 lets the air enter in the WL reservoir or channel 1703 to replace the WL 1701 absorbed by the PM 1705. FIG. 17(D), termination: the propulsion pump (so called iSIMPLE) is terminated either when all WL 1701 is absorbed into the PM 1705 or when the PM 1705 is saturated by the WL 1701.

Figure 18:
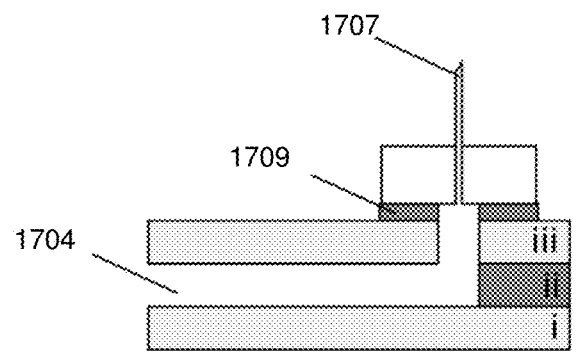
FIG. 18 is a graphic of a needle/microneedle connection to the propulsion pump (so called iSIMPLE) chip. The device is shown on side view: i) bottom layer, ii) outlet channel (OC) cut in PSA, iii) top layer with outlet hole. A connection ring (CR) made of PSA is used to connect the outlet of the propulsion pump (so called iSIMPLE) chip with the inlet of the needle/microneedle.

FIG. 18 is a graphic of a needle/microneedle 1707 connection to the propulsion pump (so called iSIMPLE) chip. The device is shown on side view: i) bottom layer, ii) outlet channel (OC) 1704 cut in PSA, iii) top layer with outlet hole. A connection ring (CR) 1709 made of PSA is used to connect the outlet of the propulsion pump (so called iSIMPLE) chip with the inlet of the needle/microneedle.

Figure 19:
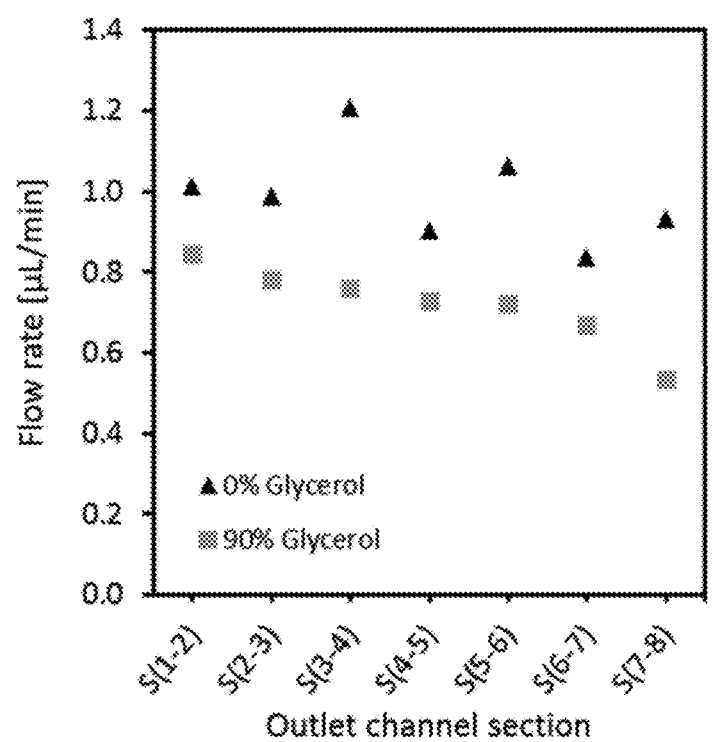
FIG. 19 is a graph that depicts the flow rate of the outlet liquid in the different sections (i.e. S(1-2), each of 1.91 µL) for outlet liquid of different viscosity. Each point represents the flow rate values obtained for water solutions with 0% and 90% glycerol.

FIG. 19 is a graph that depicts the flow rate of the outlet liquid in the different sections (i.e. S(1-2), each of each 1.91 µL) for outlet liquid of different viscosity. Each point represents the flow rate values obtained for water solutions with 0% and 90% glycerol.

Figure 20B:
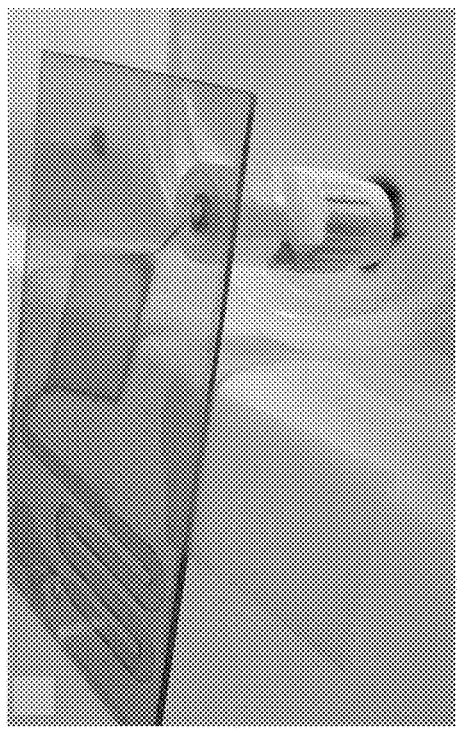
FIGS. 20(A) to 20(D) shows FIG. 20(A) the propulsion pump (so called iSIMPLE) chip for drug delivery assembled and prefilled with an array of five 32G (0.2 mm) needles.
Figure 20D:
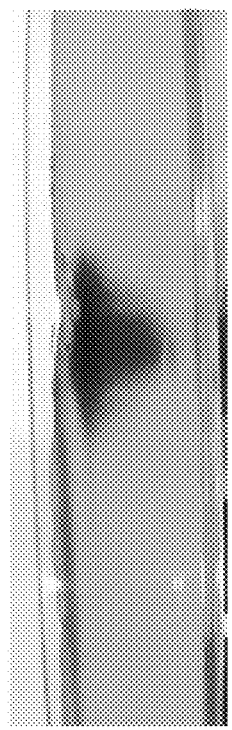
Figure 20A:
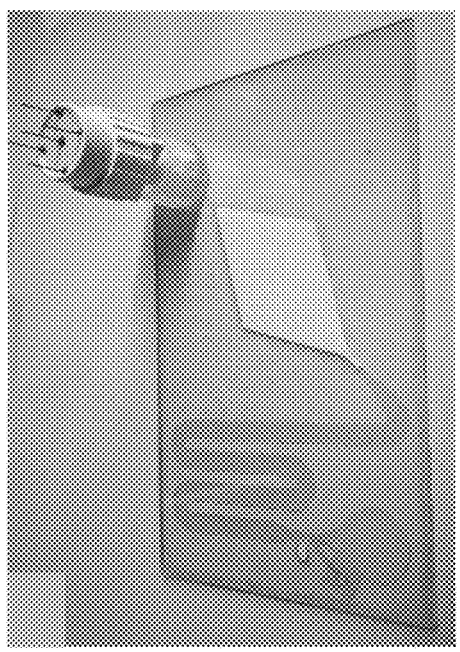
Figure 20C:
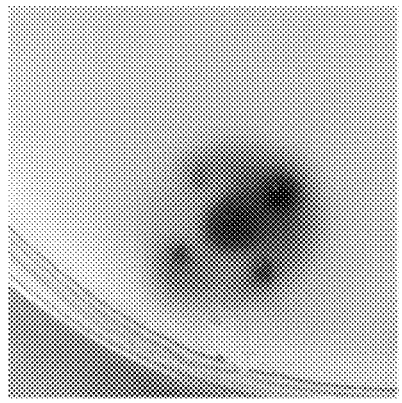

FIGS. 20(A) to 20(D) shows FIG. 20(A) the propulsion pump (so called iSIMPLE) chip for drug delivery assembled and prefilled with an array of five 32G (0.2 mm) needles. FIG. 20(B), operation of the propulsion pump (so called iSIMPLE) chip with microneedle array while injecting in 1% agarose matrix. FIGS. 20(C) and 20(D), top and side view of the agarose matrix after injection were the red colored outlet liquid is clearly injected in the matrix.

Figures 21, 22:
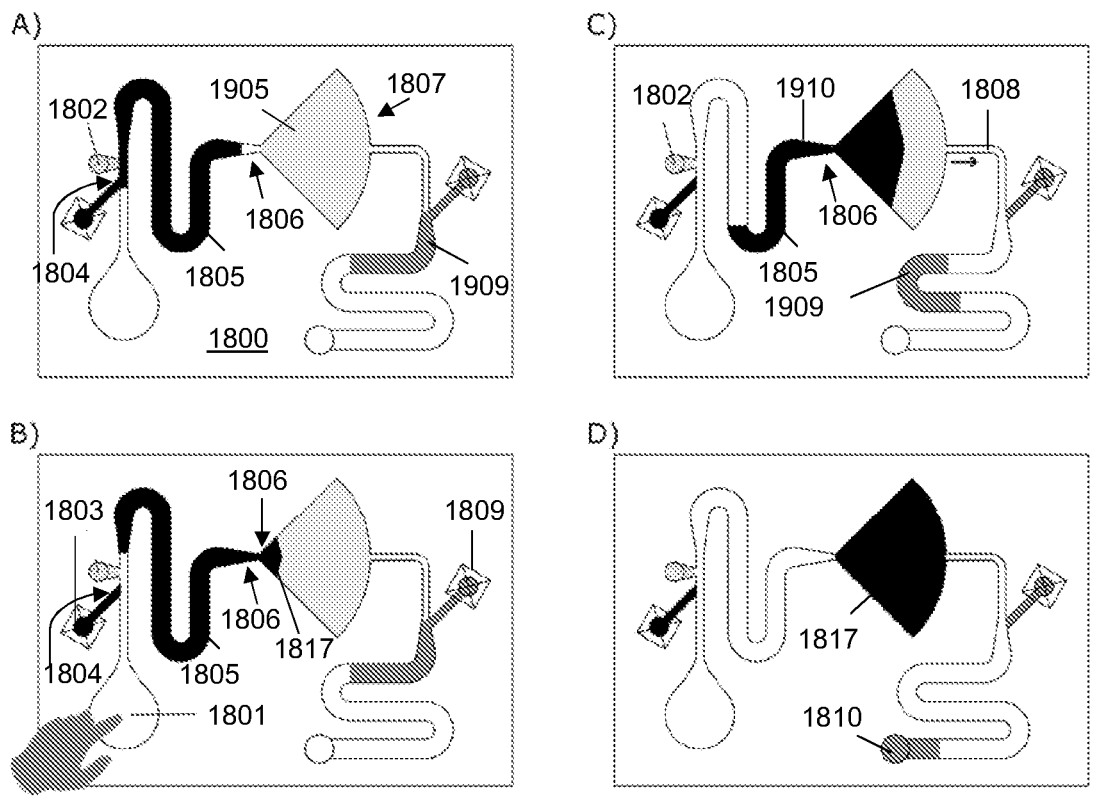
FIG. 21 shows Table A: Calculated pressure (using Hagen-Poiseuille law) needed to eject a liquid with different viscosity (0-100% glycerol concentrations) through a needle of different diameter (i.e. 26G (0.404 mm) and 34G (0.16 mm)) at 20° C. using a flow rate of 0.8 µL/min.

FIG. 21 shows Table A: Calculated pressure (using Hagen-Poiseuille law) needed to eject a liquid with different viscosity (0-100% glycerol concentrations) through a needle of different diameter (i.e. 26G (0.404 mm) and 34G (0.16 mm)) at 20° C. using a flow rate of 0.8 µL/min FIGS. 22(A) to 22(D) are a scheme of a device 1800 with fluid conduit system to manipulate fluids. It comprises the elements of a fluid actuator unit 1801, a shunt conduit with downstream a gas-permeable liquid-sealed unit with a vent hole 1802 and a solid sorbent enclosed in chamber with entry and outlet access engaged with the fluid conduit system. The solid sorbent 1905 enclosed in an enclosure or chamber, forming the pump 1807, has preferably the shape of a circle sector in a design with unit with a vent hole 1802. Using the shape of a circle sector for the enclosure or chamber is not a strict requirement for the working of the principle itself but it has been shown in literature that a circular sector shape provides a constant flow rate of the liquids manipulated by the pump, which is a preferred condition in microfluidics. It may be a 10° to 150° sector, for example a 50° to 70° sector. The shunt conduit of the unit with the vent hole 1802 and the sorbent enclosure with solid sorbent, which forms the pump 1807, are each engaged by a fluid transit with a fluid conduit that comprises at least three zones i) a first conduit zone 1804 pre-filled with a liquid 1817 upstream of the unit with the vent hole shunt conduit, ii) a third conduit zone 1806 upstream of the solid sorbent enclosure of the pump 1807 and iii) a second conduit zone 1805 pre-filled with a liquid 1817 positioned between the first and third conduit zone and directly connected to the first conduit zone. It is noted that in this particular example, the volume of the first conduit zone is determined by the volume of the portion of conduit delimited by the shunt conduit of unit with the vent hole 1802 and the shunt conduit of the inlet 1803. Proper functioning of the actuated fluid manipulation is a technical effect of the volume of the first conduit zone 1804 upstream of the unit with the vent hole shunt conduit, e.g. upstream of the hydrophobic valve, being proportionally larger than or equal to the volume of the third conduit zone 1806. In this demonstrated device the solid sorbent enclosed in chamber functions as a propulsion pump 1807 that via escape of gas from its exit port into the liquid conduit 1808 propels a downstream fluid further towards the vent or outlet 1810 for releasing fluid into the external or ambient environment of said the device. This liquid can be uploaded into the device via an outlet port 1809 connected to the outlet channel and its liquid conduit 1808. Outlet port 1809 may comprise a liquid reservoir that with liquid passage port is engaged with the fluid conduit web and eventually (as here is the case) with an intermittent conduit shunt between the fluid conduit web and the reservoir. The reservoir can receive or contain a fluid with reagent, analyte, a ligand, a biological active molecule, a chemical reactive molecule or a physical reactive molecule. Outlet port 1809 can be also an intake port adapted to receive a liquid for instance comprising a ligand to be analyzed. This intake port can be engaged with a reservoir. This intake port can be sealed from gas intake by way of sufficient liquid on it, whereby this liquid can be under ambient pressure. The scheme furthermore shows the inlet 1803 with sealed reservoir so that it forms an enclosure. Such reservoir can be provided with a seal that is openable or closeable, for instance with a seal that can be in a closed or open position. Or it can be foreseen with a seal that is removable, openable or closable to open or close reservoir. Such reservoir of inlet 1803 can thus contain a working fluid to engage in the fluid manipulation. The reservoir can receive or contain a working fluid to engage in fluid manipulation, as is the case in the inlet 1803 of the figure. If Vp is the volume of gas (for instance air) between the working liquid and the porous material in order to properly function after actuation it must be smaller than Vup, the volume of working liquid upstream the hydrophobic vent (e.g. hydrophobic valve). Moreover, the volume of air in the air pouch should be larger than Vp and at least equal and preferably larger than Vup as well.

This makes the activation much more robust. One can push 1, 2, 5, times, hard or soft but from the moment the pump is activated, the air pouch and everything upstream the vent is disconnected with the rest of the circuit and so it won't influence the pumping operation.

More in detail, the phases of actuation may comprise the following steps:

The enclosure of the capillary pump 1807 is connected to an inlet channel 1910 and to an outlet channel or liquid conduit 1808. The inlet channel 1910 is further connected to a hydrophobic valve or a shunt channel with hydrophobic valve (unit with a vent hole 1802), and further upstream to a working liquid reservoir or inlet 1803 and further upstream to an reservoir acting as actuator unit 1801 having a flexible or depressible wall, wherein a reservoir for the inlet 1803 and the inlet channel 1910 contain the working liquid 1817. FIG. 22(A), initiation: working liquid 1817 and outlet liquid 1909 are preloaded in the respective chambers while a porous material 1905 was housed in its chamber during the fabrication, forming the capillary pump 1807. A hydrophobic valve comprising a hydrophobic material (e.g. a filter paper treated to become hydrophobic) in a unit with a vent hole 1802 was positioned on a side of the working liquid chamber 1910 after the working liquid prefilling point, so the working liquid is not in contact with the hydrophobic material. The other side of the hydrophobic valve is open to the external environment, e.g. to ambient air, via the vent hole of the unit with a vent hole 1802.

FIG. 22(B), activation: pushing on the actuator unit 1801 (or activation zone) moves the working liquid 1817 in the inlet channel 1910 so that it contacts the solid sorbent 1905 leading to the absorption of the working liquid 1817 by the solid sorbent (porous material) 1905. This process is similar as explained with reference to FIGS. 17(A) to 17(D).

FIG. 22(C), operation: while the working liquid 1817 is absorbed into the solid sorbent (porous material) 1905, it pushes out the air present in the solid sorbent 1905. This air pushes the outlet liquid 1909 towards the outlet 1810. The hydrophobic valve (unit with vent hole 1802) lets the air enter in the working liquid reservoir and/or the inlet channel 1910, to replace the working liquid 1817 absorbed by the porous material 1905. FIG. 22(D), termination: the propulsion pump is terminated either when all working liquid 1817 is absorbed into the solid sorbent (porous material) 1905, or when the solid sorbent (porous material) 1905 is saturated by the working liquid 1817. A technical effect of the hydrophobic valves is easier and more robust actuation of the fluid manipulation system. The right sequence "closing inlet hole"–"pressing the activation area"–"opening the inlet hole"–"releasing the pressure on the activation area" is not required anymore to actuate. By allowing the air to enter in the working liquid reservoir to replace the working liquid 1817 absorbed by the porous material 1905, thanks to the hydrophobic valve, the actuation of the process by pressure on the flexible enclosure of the actuator or actuator unit 1801 is robust. In a specific embodiment the hydrophobic valve (unit with vent hole 1802) comprises a porous material (i.e. filter paper) which may be the same as the porous material in the enclosure of the capillary pump 1807, but treated with hydrophobic coating (i.e. Aquapel). The hydrophobic solution is applied on the porous material and let it dry completely. This may form a barrier. The hydrophobic valve can be made permeable to gas but not to hydrophilic liquid. This is only one example of method for obtaining a gas-permeable liquid-sealed unit with vent hole 1802.

Figure 23A:
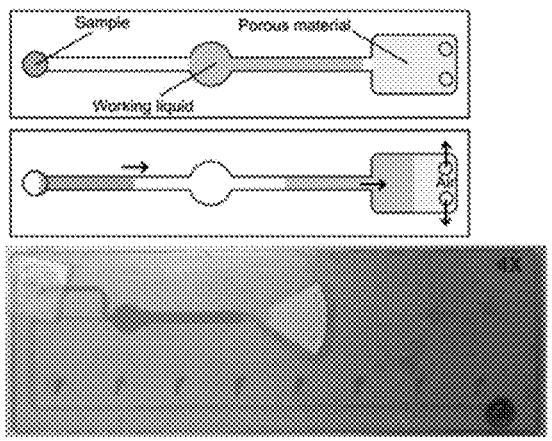
FIGS. 23(A) and 23(B) are a graphic and photographic that displays FIG. 23(A) a suction pump and FIG. 23(B) a propulsion pump.
Figure 23A:
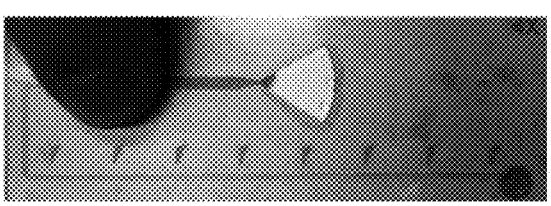
Figure 23A:
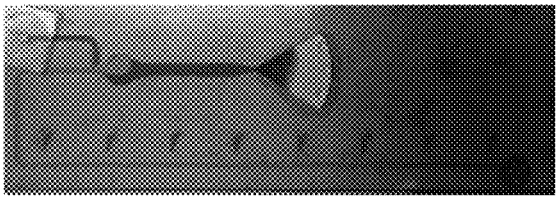
Figure 23A:
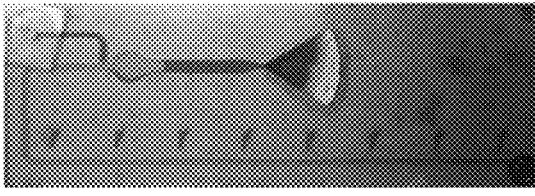
Figure 23A:
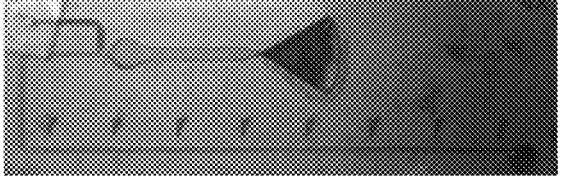
Figure 23B:
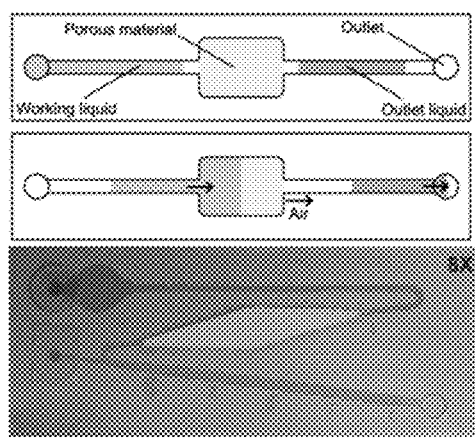
Figure 23B:
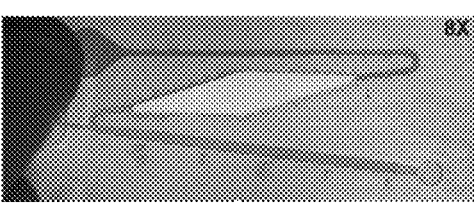
Figure 23B:
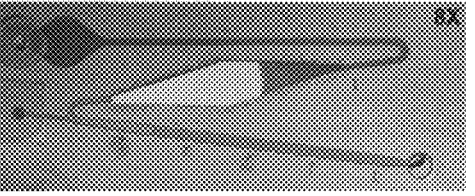
Figure 23B:
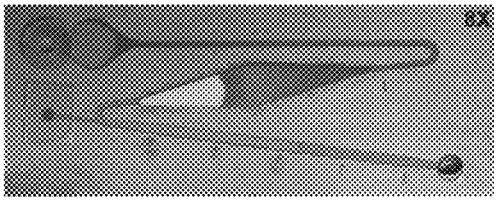
Figure 23B:

FIGS. 23(A) and 23(B) are a graphic and photographic illustration that displays FIG. 23(A) a suction pump and FIG. 23(B) a propulsion pump. The a suction pump, FIG. 23(A), is based on a sorbent materials, for instance a solid sorbent enclosed in chamber with port engaged with the fluid conduit system and at least one port engaged with the extern environment the working liquid when brought in contact with the sorbent material, for instance by a finger push on the flexible or depressible wall of an enclosure with working fluid engaged on the fluid conduit, than the absorption of said working liquid from the inlet channel and/or reservoir by said solid sorbent exerts a suction force on such working fluids contained in said connected fluidic network or fluid conduit web. Such suction pump can be activated by applying pressure to the flexible or depressible wall of the reservoir that functions as the actuator, e.g. by compressing the reservoir comprising the working liquid, so as to contact the working liquid to the solid sorbent of the suction pump, thus initiating the absorption of the working liquid 809 by the solid sorbent of the suction pump. While the solid sorbent absorbs working liquid, liquid is expelled out of the cavities of the solid sorbent of the suction pump, and is evacuated from the enclosure through the vent-holes. Such vent-holes can vent the fluid to the external environment.

FIG. 23(B) displays the propulsion pump whereby the pump comprises a sorbent materials, for instance a solid sorbent enclosed in chamber which chamber is intermittent with a fluid conduit by an inlet and an outlet. Typically in such propulsion pump a gas is expulsed from a solid sorbent during the absorption of a liquid by said solid sorbent into a fluid conduit (for instance fluid channel) referred to as outlet channel, this fluid flow provides a propulsion force, which allows for pushing a fluid contained in said outlet channel and/or connected a web of fluid conduits or network of channels over a predictable trajectory. When a working fluid is brought in contact with said the fluid sorbent material solid sorbent exerts a suction force on this working fluid and another fluid comprised in cavities of the sorbent material is pushed through an outlet port into the downstream conduit hereby propelling the fluid that is comprised in said this downstream conduit towards a vent further downstream into the conduit system.

Figure 24A:
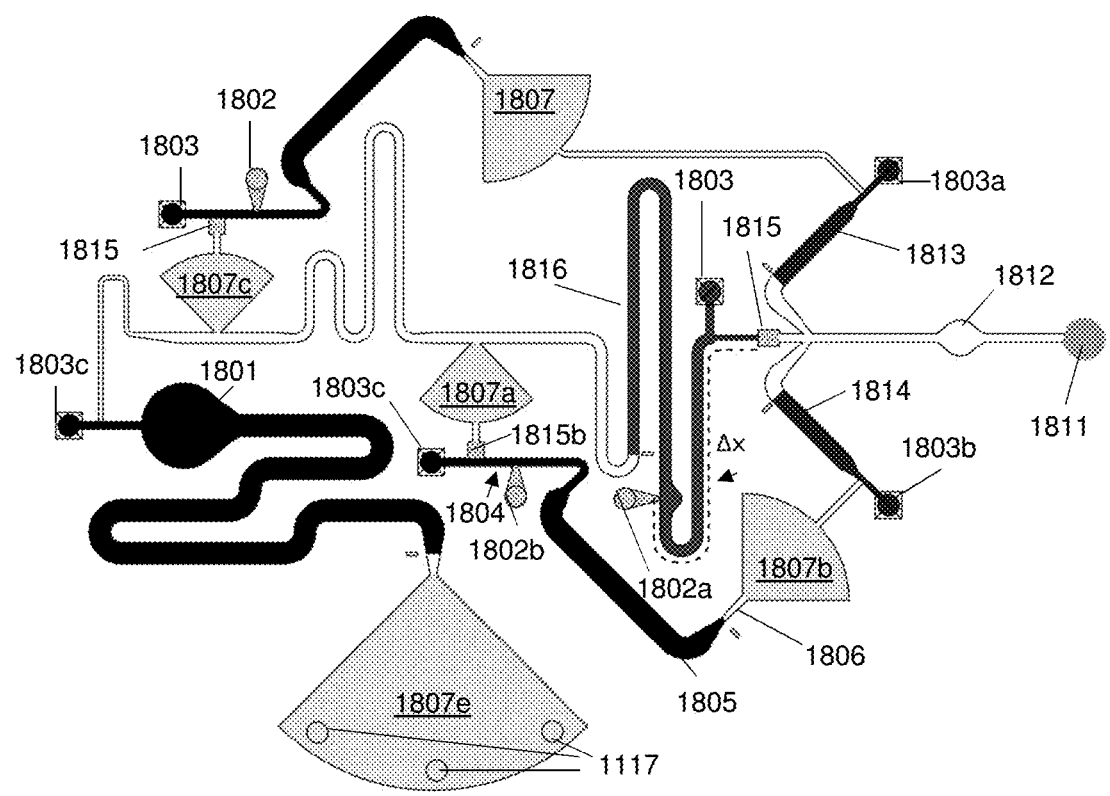
FIGS. 24(A) to 24(H) are a schematic illustration of the device with fluid conduit system to manipulate fluids of present invention with a fluid conduit web that is featured to operate as an ELISA with or without microbeads seeding over an array of holes, for instance in the analytical zone.
Figure 24B:
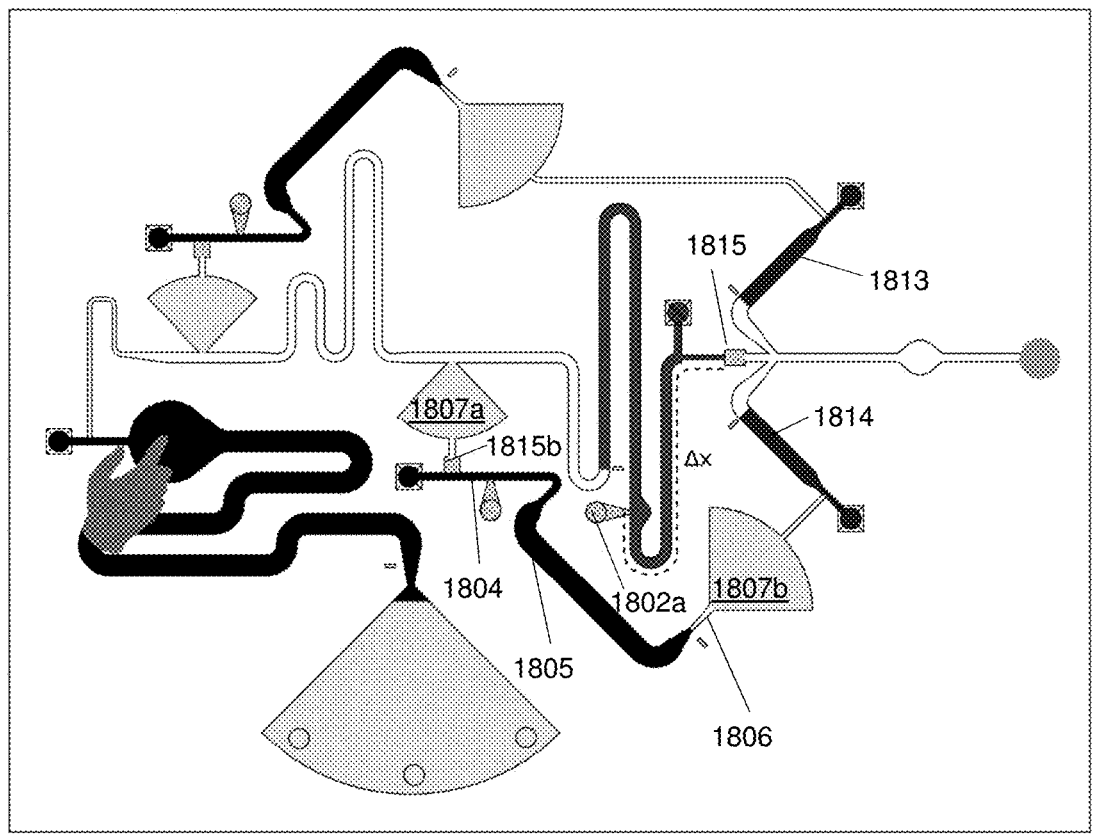
Figure 24C:
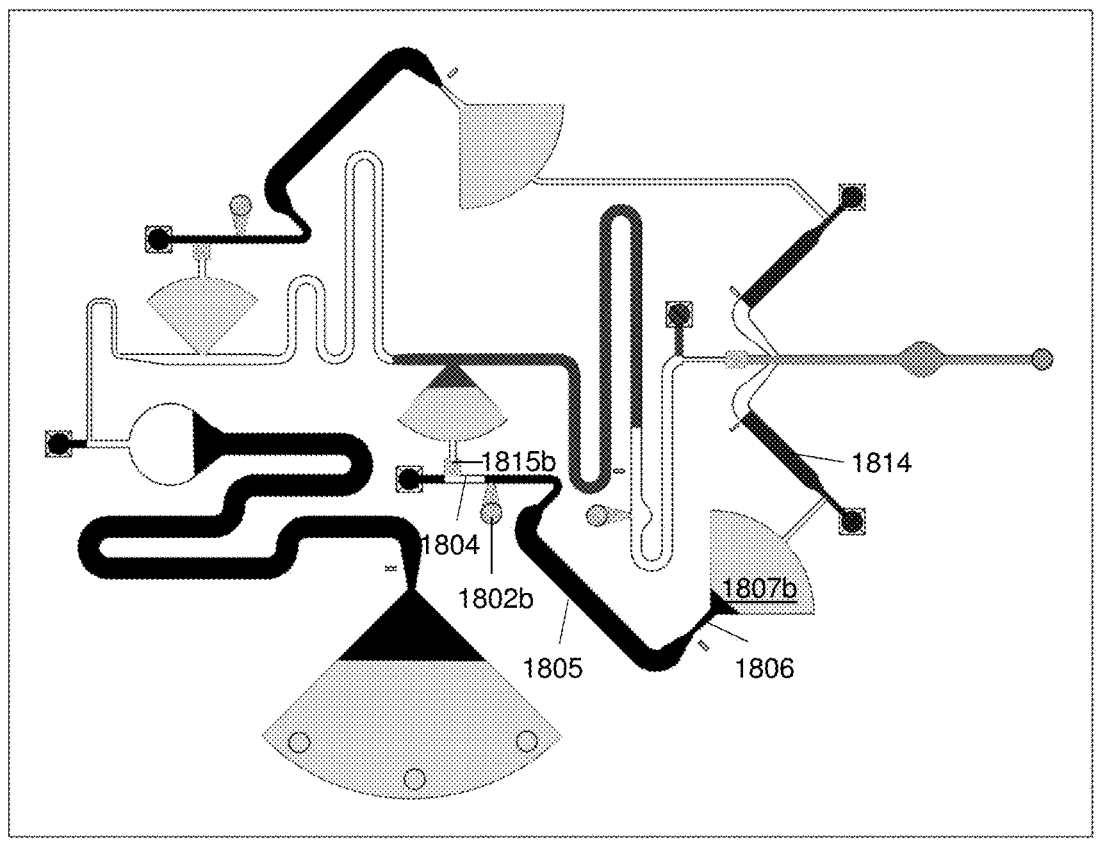
Figure 24D:
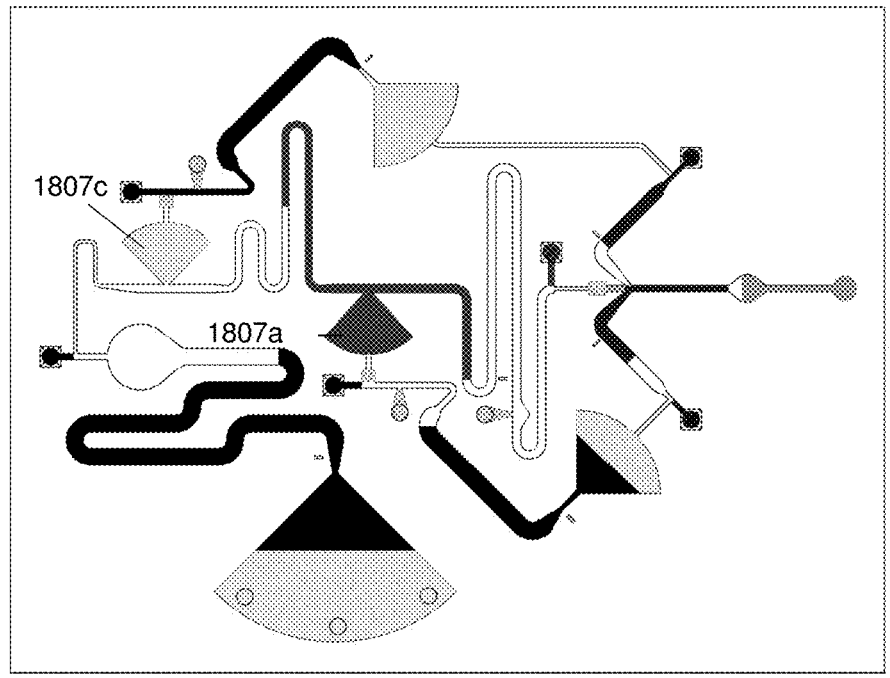
Figure 24E:
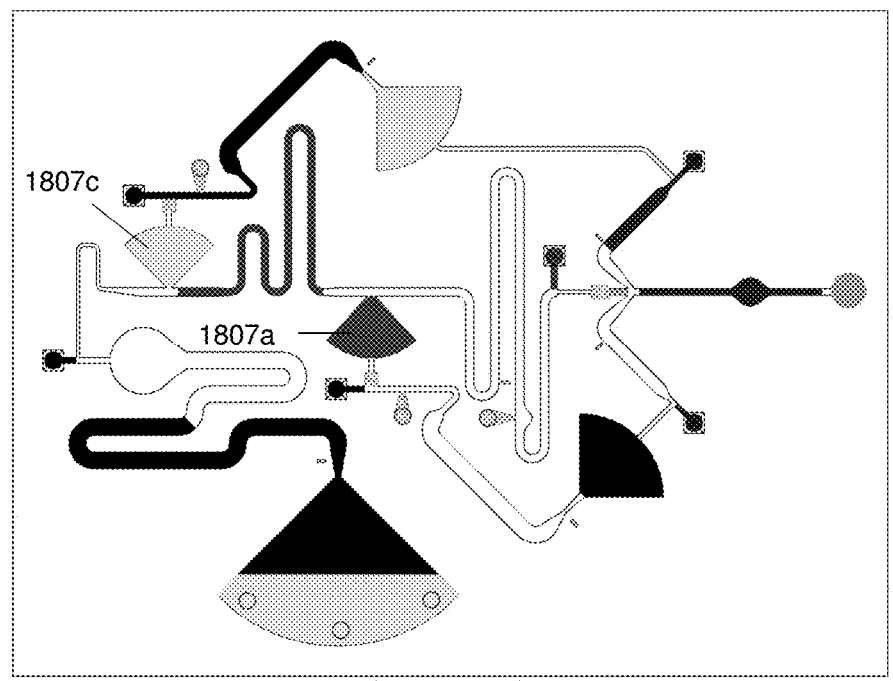
Figure 24F:
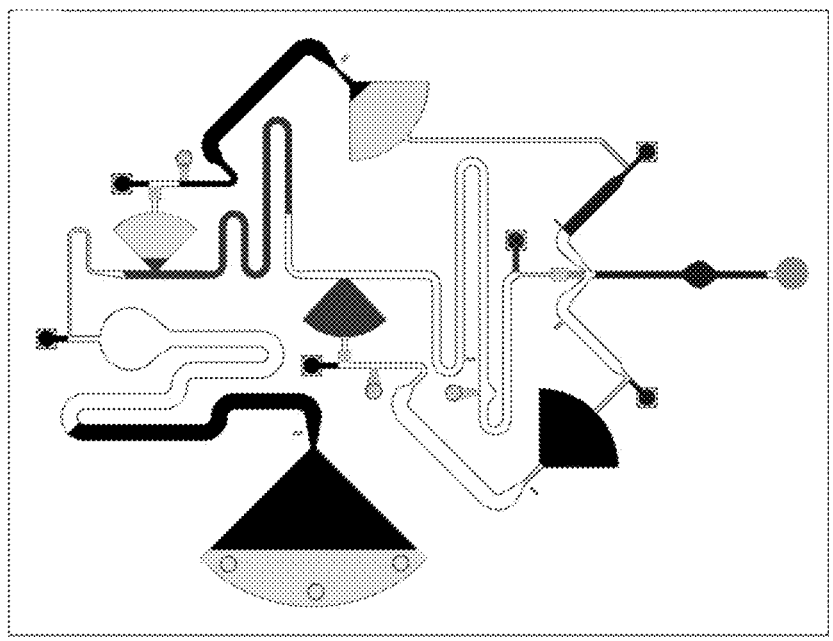
Figure 24G:
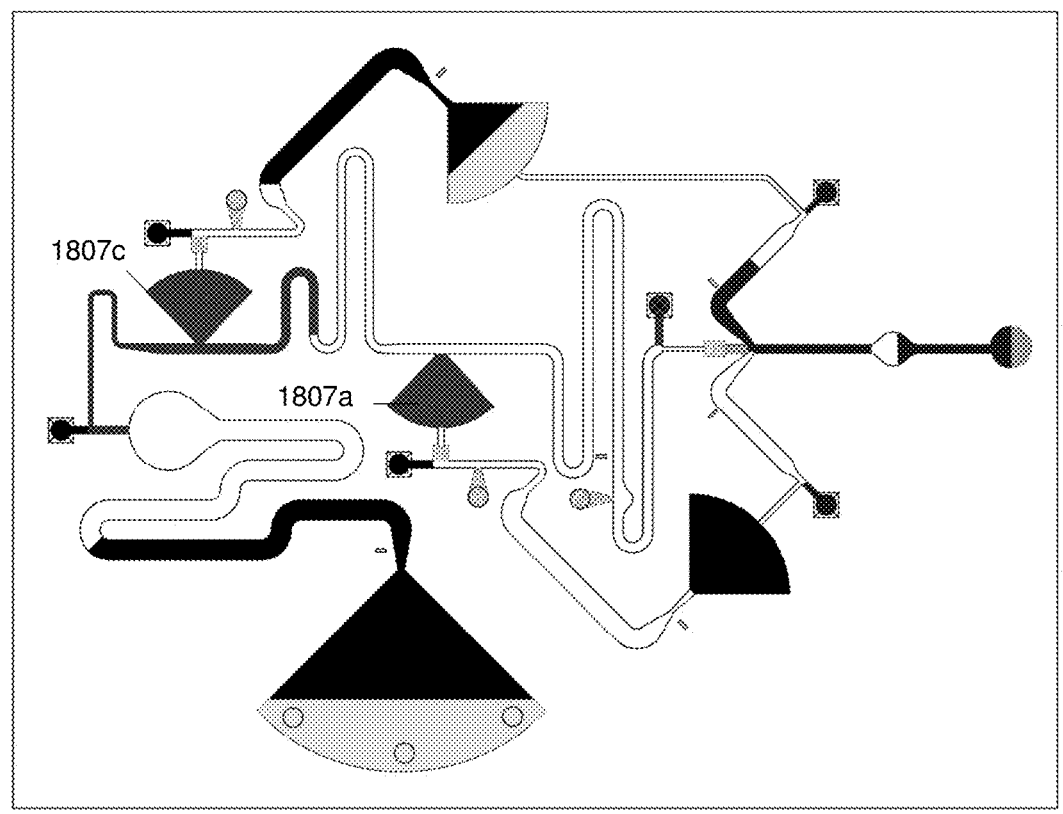
Figure 24H:
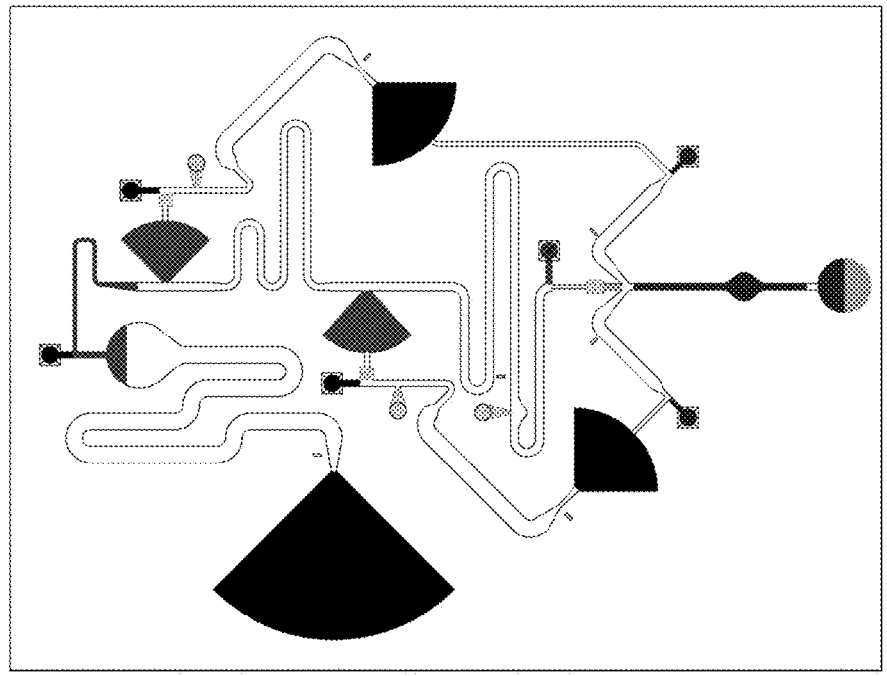

FIGS. 24(A) to 24(H) are a schematic display of the device with fluid conduit system to manipulate fluids of present invention with a fluid conduit web that is featured to operate as an ELISA with or without microbeads seeding over an array of holes, for instance in the analytical zone. The array of holes can be used in presence of beads, but the present invention is not limited to an the array of holes, for example in case of traditional ELISA, the analytical zone could be functionalized with receptors (Antibody, DNA, . . . ) with the targets, reagents and substrate being flown over by the different pumps. In FIG. 24(A), element 1815 includes a gate adapted to form a passageway for gas and a barrier for liquid. The actuator unit 1801 may comprise a collapsible enclosure with a fluid (in this case a liquid) so that this element is adapted to actuate the fluid conduit system to manipulate the fluids by manual actuation, e.g. it may be finger-actuated, for instance by finger pressure. The unit with a vent hole 1802 includes a shunt conduit with downstream a gas-permeable liquid-sealed vent hole (e.g. unit with vent hole). Such gas-permeable liquid-sealed vent hole can include a hydrophobic material containing cavities for gas passage be sealed against aqueous liquids, for instance a hydrophobic paper. In a working example such hydrophobic paper had been made from a filter paper, Whatman filter paper, Grade 43 of Merck by impregnation with fluorinated compounds. This was an easy to make and inexpensive method to generate a gas permeable—(water based-) liquid impermeable barrier for being comprised into the unit with the vent hole 1802 or into element 1815.

The technical effect of such element is that this element provides a passage for gas fluid, but it is not a passageway for aqueous fluids. Systems with such gates have a more robust actuation. Gasses will find a passage or will be conveyed into a neighboring fluid conduits. A capillary pump 1807 includes a solid sorbent enclosed in a chamber with entry and outlet access engaged with the fluid conduit system. Vent-holes 1117 for releasing fluid into the external or ambient environment of said the device are included, similarly to the vent-holes 107 of FIGS. 2(A) to 2(D) or in FIGS. 11(A) to 11(E), for example. Inlet 1803 may include a liquid reservoir that with liquid passage port is engaged with the fluid conduit web and eventually (as here is the case) with an intermittent conduit shunt between the fluid conduit web and the reservoir. The reservoir can receive or contain a working fluid to engage in fluid manipulation, as is the case in inlet 1803c. There reservoir can receive or contain a fluid with reagent as is the case in the inlets 1803a and 1803b. The illustration shows the inlets 1803 with sealed reservoir so that it forms an enclosure. Such reservoir can be provided with a seal that is openable or closeable, for instance with a seal that can be in a closed or open position. Or it can be foreseen with a seal that is removable, openable or closable to open or close reservoir. Such reservoir can thus contain a working fluid to engage in the fluid manipulation. Or such reservoir can contain an analyte, a ligand, a biological active molecule, a chemical reactive molecule or a physical reactive molecule. Element 1811 is an intake port adapted to receive a liquid comprising a ligand to be analyzed. This intake port can be engaged with a reservoir. This intake port can be sealed from gas intake by way of sufficient liquid on it, whereby this liquid can be under ambient pressure. This intake port can also be sealed from gas intake by the fact that it is submersed in fluid, for instance an external fluid for sampling and analysing. This way the fluid conduit web comprises a conduit shunt connected with a port for sampling fluid, for instance from an external environment or from an ambient fluid environment. This way the fluid conduit web comprises a conduit shunt physically or functionally connected with a port for sampling fluid, for instance from an external environment or from an ambient fluid environment.

The FIGS. 24(B) to 24(H) demonstrate such device at actuation and in various phases of its operation. Hydrophobic barrier 1 1815 separates the analytical part of the chip (upstream) from the pumping part (downstream) so that the trigger liquid cannot go in the analytical part during prefilling and so that a fluorogenic substrate or reagents 1813, 1814 (prefilled downstream the propulsion pumps) are pushed only over the analytical part. DeltaX define the volume of sample (i.e. body fluids, buffer solutions, functionalized microbeads) that will be pulled into the system. In fact, from the moment the trigger liquid 1816 moves by DeltaX, it reaches the hydrophobic valves (e.g. the gas-permeable liquid sealed unit with vent hole 1802*a*) and from that moment on, the suction pump won't act on the analytical part anymore since it can take the air from the hydrophobic valves (e.g. units with vent hole 1802*a*). This also allows an incubation time over the analytical zone of the sample. The trigger liquid serves also as working liquid to activate the propulsion pump 1807*a* activation trigger. This is made of: a trigger porous material which absorbs the trigger liquid and a hydrophobic barrier 1815*b* which separates the propulsion pump working liquid 1817 from the trigger porous material (e.g. forming the trigger capillary pump 1807*a*). The air expelled by the triggers porous material pushes the propulsion pump working liquid in contact with the propulsion pump porous material and from the moment the propulsion pump working liquid overcome the hydrophobic valve 1802*b* (FIG. 24(C)), the propulsion pump becomes independent from the rest of the circuit and pushes the Fluorogenic substrate or reagent 1814 in the analytical part. Important to notice that the volume of air pushed out from the trigger porous material (for instance included in its capillary pump 1807*a*) must be larger than the volume of working liquid 1817 between the hydrophobic barrier 1815*b* and the hydrophobic valve (unit with vent hole 1802*b*), thus the volume in the first conduit zone 1804, so the back end of the working liquid 1817 can surpass the unit with vent hole 1802*b*, which in turn must be larger than the volume of air between the propulsion pump 1807*b* porous material and the propulsion pump working liquid 1817 front, thus the volume in the third conduit zone 1806, to ensure that the working liquid 1817 can reach the propulsion pump 1807*b*. The distance between the front of the trigger liquid and the interface with the trigger porous material define the delay between the activation of the Suction pump and the activation of the first propulsion pump (for a fixed flowrate). This is also related to the incubation time of the sample (i.e. beads, analyte) on the analytical zone. Moreover, the trigger liquid should be enough to trigger the activation of all the propulsion pumps present (in this case two 1807*a*, 1807*c*) and the suction pump 1807*e* is designed to pull the trigger liquid 1816 sufficiently to activate all the propulsion pumps. The delay between the activation of the propulsion pumps 1807*a*, 1807*c* is determined by the distance between them, which can be tailored under the assumption that the trigger liquid 1816 is being pulled at a constant rate by the suction pump 1807*e*.

Figure 25:
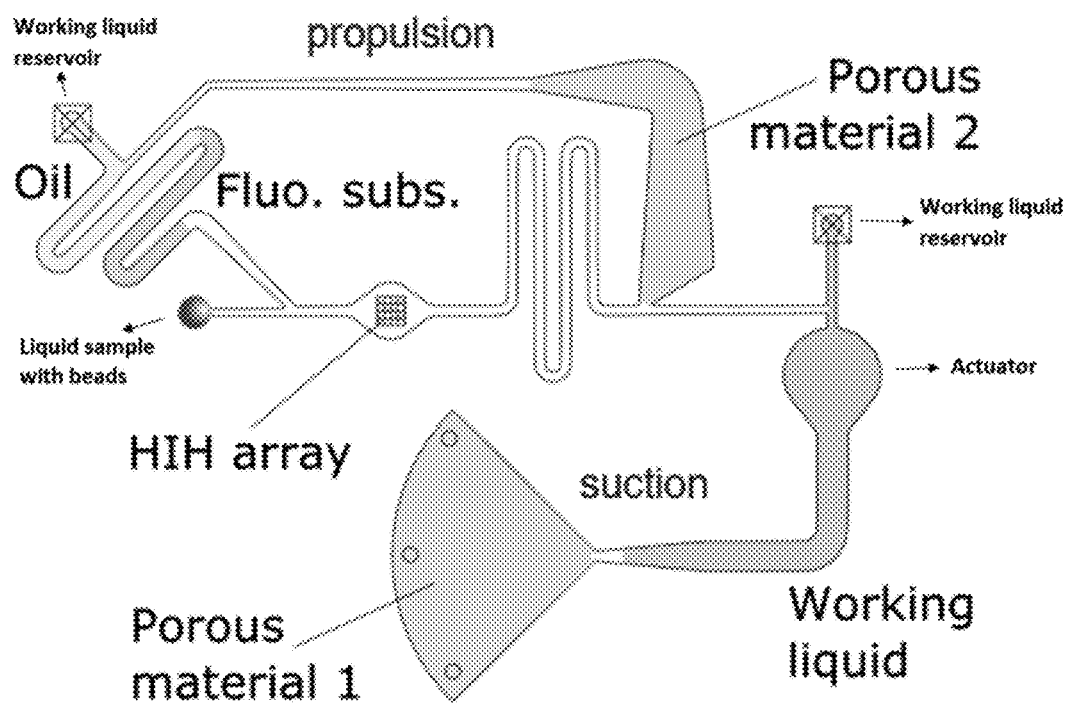
FIG. 25 is a graphic display of a functionally engaged suction pump and propulsion pump integrated into a fluid conduit web or microfluidic network moreover comprising an enclosure hydrophilic-in-hydrophobic (HIH) microtube or microwell grids array in said the fluid conduit system.

FIG. 25 is a graphic display of a functionally engaged suction pump and propulsion pump integrated into a fluid conduit web or microfluidic network moreover comprising an enclosure hydrophilic-in-hydrophobic (HIH) microtube or microwell grids array in said the fluid conduit system. Such array 1812 is also shown in FIG. 24(A).

FIGS. 26(A) to 26(F) are a graphic that demonstrates an embodiment with a suction pump and propulsion pump series with engagement of a hydrophobic valve (HV). FIG. 26(A), initiation: outlet liquid (OL), trigger liquid (TL), working liquid 1 and 2 (WL 1, WL 2) are preloaded in the respective chambers while a droplet of sample (S) is placed on the inlet of analytical channel (AC). Porous material 1 (PM 1) chamber is connected to TL chamber which is then connected to WL 2 chamber.

A hydrophobic valve (HV) is placed between the trigger liquid (TL) and a second working liquid (WL 2) which is more downstream of a first working liquid (WL 1). The technical effect of the hydrophobic valve (HV) with its entry access pore or gate physically and operationally connected to the guidance that is downstream of a working liquid (herein trigger liquid) is that this trigger liquid that is pushed for instance from a pressure build up from air escaping from the output of the enclosure of a upstream propulsion pump into a gas filled guidance that is after the valve intermittent with a working fluid filled guidance, will not move this downstream working before this trigger liquid reaches the valve. The technical effect is of such design is a delay. Thus, the valve has a role in both the activation of the pump and also to delay and trigger the activation of one pump by another.

FIG. 26(B), activation Suction pump: Suction pump is activated and the WL 1 is absorbed by the PM 1. FIG. 26(C), operation (i) Suction pump: a reduced pressure in the AC draws the S in the channel. At the same time the air expelled from the PM 1 pushes the TL forward. The air pushed by the TL does not act on the propulsion pump circuit downstream since it can exit the circuit through the HV. FIG. 26(D), activation propulsion pump: when the TL reach the HV, the air pushed by the TL cannot exit through the HV anymore because the same is blocked by the TL, but pushes the WL 2 in contact with the PM 2 activating the propulsion pump. The volume of TL which pushes the WL2 (at least the volume that surpasses the HV) should be large enough to make the WL2 reach the PM2. At the same time the (i) Suction pump is terminated. FIG. 26(E) propulsion pump operation: the air expelled from the PM 2 pushes the OL towards the outlet. The HV lets the air enter in the WL 2 chamber to replace the WL 2 absorbed by the PM 2. FIG. 26(F) propulsion pump termination: the propulsion pump is terminated either when all WL 2 is absorbed into the PM 2 or when the PM 2 is saturated by the WL 2. Such delay between the activation of the suction pump and the activation of the propulsion pump circuit depends on the volume between the TL front and the HV. However, this volume cannot exceed the maximum volume that can be pushed by the (i) suction pump. If the PM 2 chamber is directly connected to the end of the AC (without prefilling of OL), the same system can be used to push back and forth the S in the A FIG. 27: Schematic work flow for the fabrication of the microwell array grounding plate, using both an Parylene-C shadow mask and an aluminium hard mask. Fabrication of 62,500 femtoliter-sized HIH microwells on glass plate through dry lift-off method: a) deposition of the thin layer of Al, b) deposition of Teflon-AF, c) deposition of parylene C, d) deposition of the Al hard mask, e) UV exposure of the photoresist, f) development of the photoresist and wet etching, g) reactive ion etching, h) dry peel-off method and i) finalization of HIH microwell array.

Figure 28:
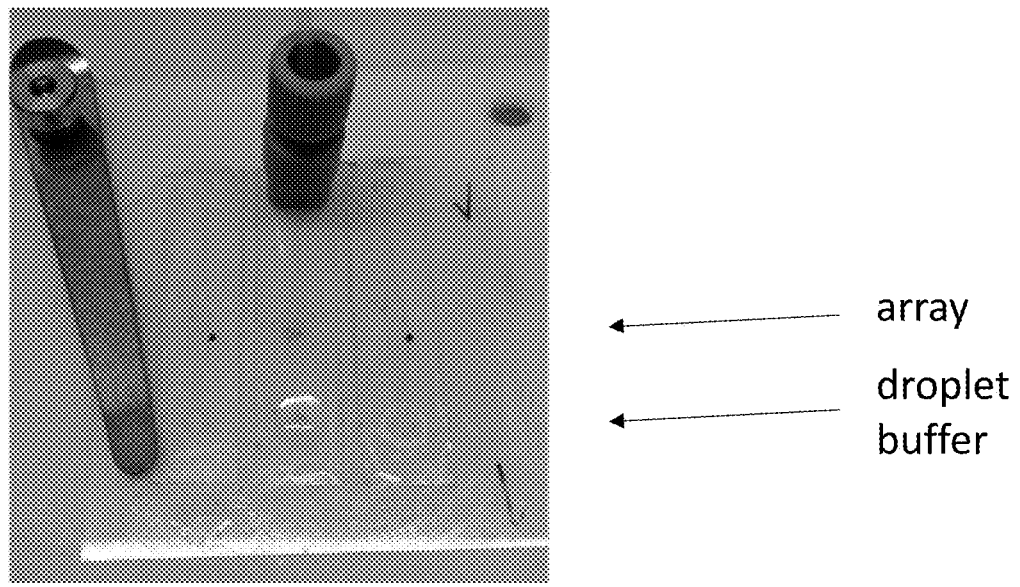
FIG. 28: Microfluidic set-up: outlet connected to a syringe pump, magnet underneath the array and 10 µL droplet of the buffer solution on the inlet.

FIG. 28: Microfluidic set-up: outlet connected to a syringe pump, magnet underneath the array and 10 μL droplet of the buffer solution on the inlet.

Figure 29:
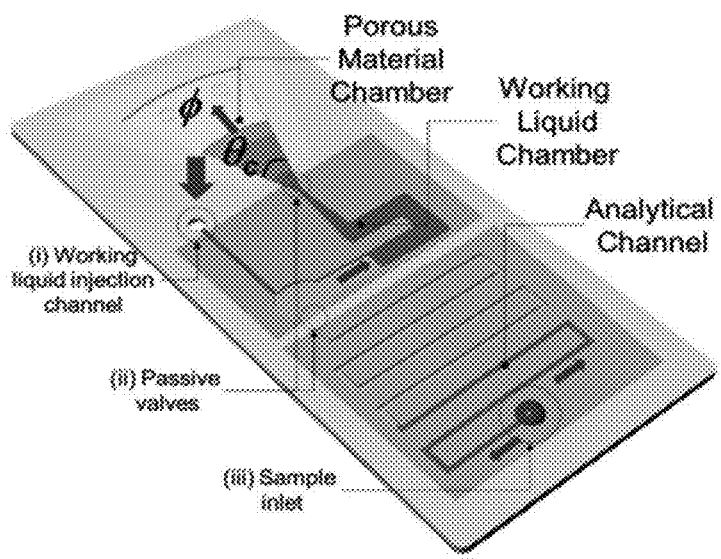
FIG. 29: Overview of the suction pump: i) part of the filter paper, ii) working liquid channel with activation button, and iii) analytical channel with sample inlet.

FIG. 29: Overview of the suction pump: i) part of the filter paper, ii) working liquid channel with activation button, and iii) analytical channel with sample inlet.

Figure 30:
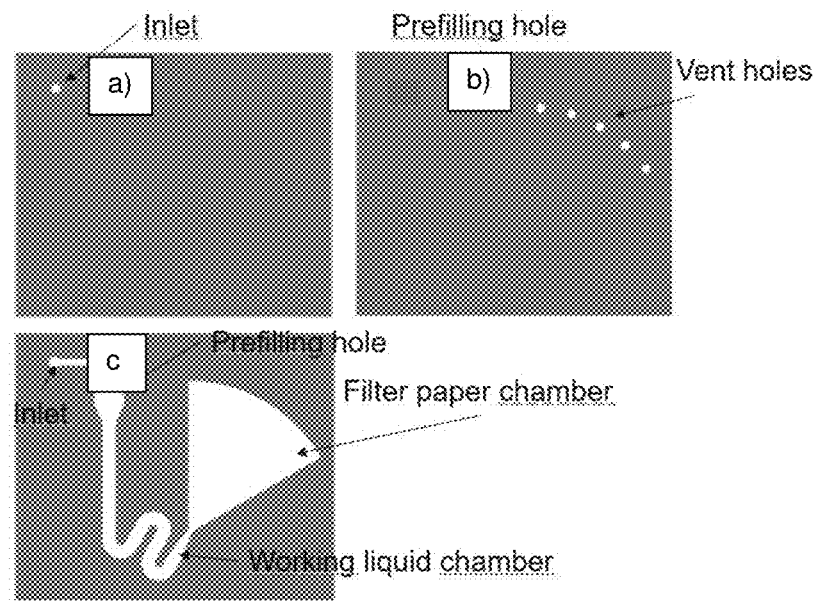
FIG. 30: Design Suction Pump: a) PSA middle layer with channel design, b) top PVC layer with vent-holes and prefilling hole, and c) bottom PVC part with inlet.

FIG. 30: Design Suction Pump: a) PSA middle layer with channel design, b) top PVC layer with vent-holes and prefilling hole, and c) bottom PVC part with inlet.

Figure 31:
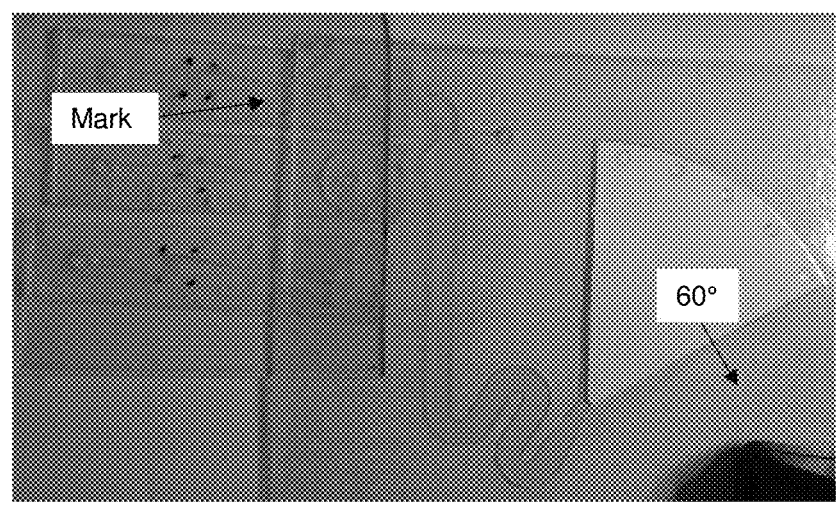
FIG. 31: Microfluidic set-up with well-known volume marks in the PSA layer, outlet of array connected to a prefilled Suction Pump.

FIG. 31: Microfluidic set-up with well-known volume marks in the PSA layer, outlet of array connected to a prefilled Suction Pump.

Figure 32:
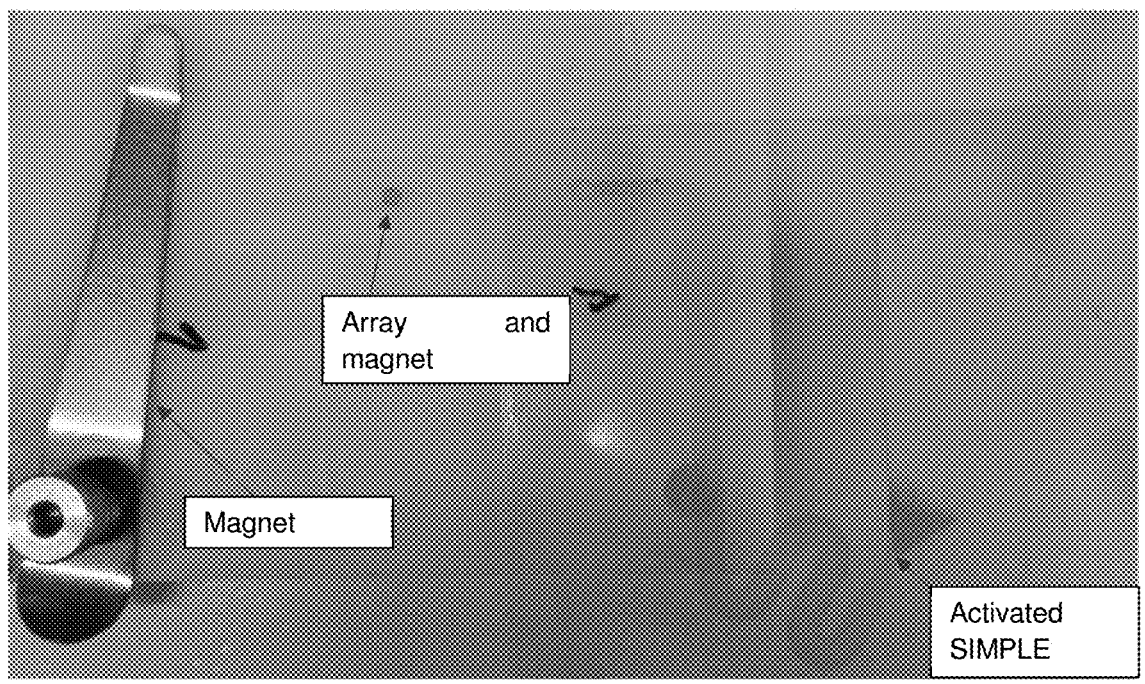
FIG. 32: Microfluidic set-up of prefilled activated Suction Pump connected with the outlet of the microwell array. The microwell array chip is clamped onto the 3D printed magnet holder.

FIG. 32: Microfluidic set-up of prefilled activated Suction Pump connected with the outlet of the microwell array. The microwell array chip is clamped onto the 3D printed magnet holder.

Figure 33:
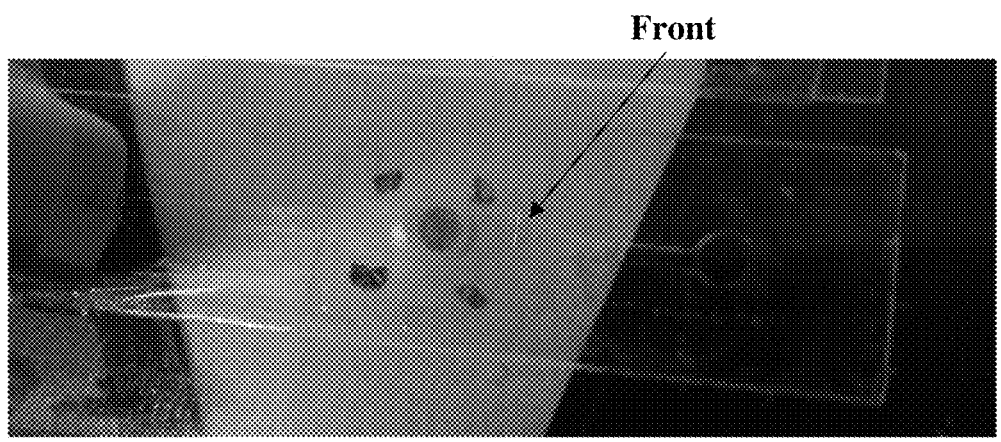
FIG. 33: The plug flow is pushing and seeding the aggregate of beads above the array.

FIG. 33: The plug flow is pushing and seeding the aggregate of beads above the array. The volume of beads solution should be limited (it can be seen as a continuous flow of a long plug). In fact part of the seeding it is achieved thanks to the back meniscus of the plug at the air liquid interface. This interface collect all the beads that are not seeded yet but attracted on the surface of the channel by the magnet and it swipe them over the array into the wells.

Figure 34:
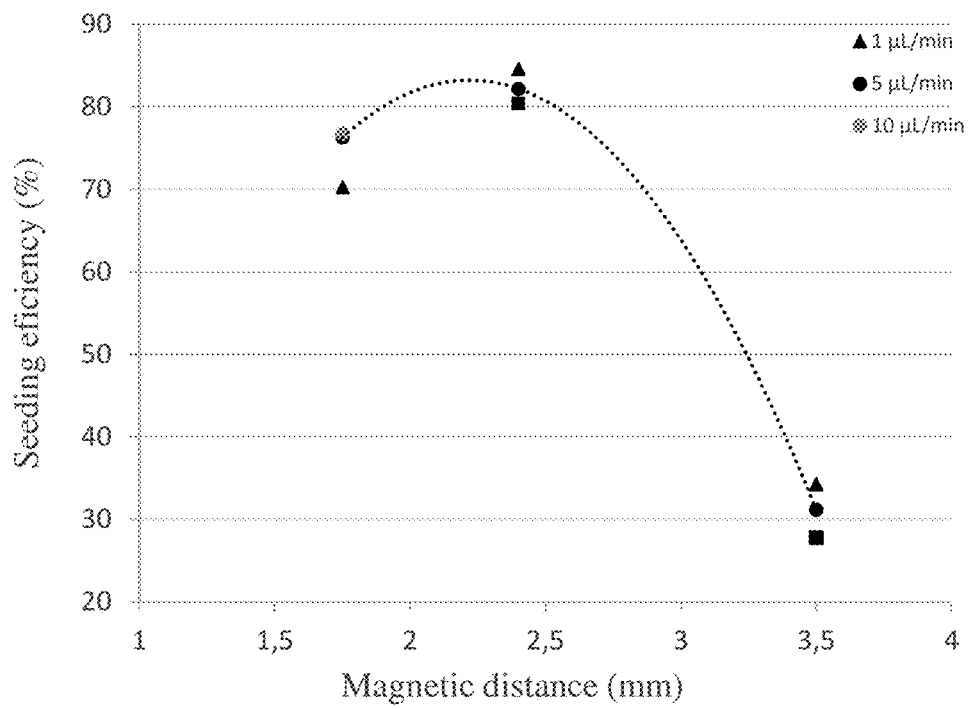
FIG. 34: Fitted results of I-optimal full factorial blocked design of seeding efficiencies at different magnet to array distances with flow rate varied between 1, 5 and 10 µl/min.

FIG. 34: Fitted results of I-optimal full factorial blocked design of seeding efficiencies at different magnet to array distances with flow rate varied between 1, 5 and 10 µl/min.

Figures 35A, 35B, 35C:
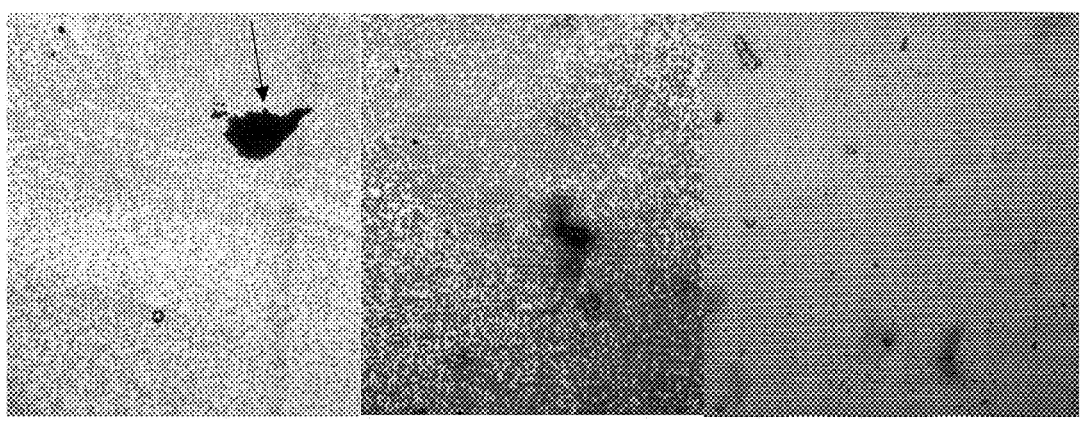
FIGS. 35(A) to 35(C): Overview microscope images for the three different distances.

FIGS. 35(A) to 35(C): Overview microscope images for the three different distances: FIG. 35(A) immobilization of the beads above the array due to too high magnetic attraction (distance of 1.75 mm), FIG. 35(B) good seeding (distance of 2.4 mm), and FIG. 35(C) low seeding due to low magnetic attraction (distance of 3.5 mm).

Figure 36:
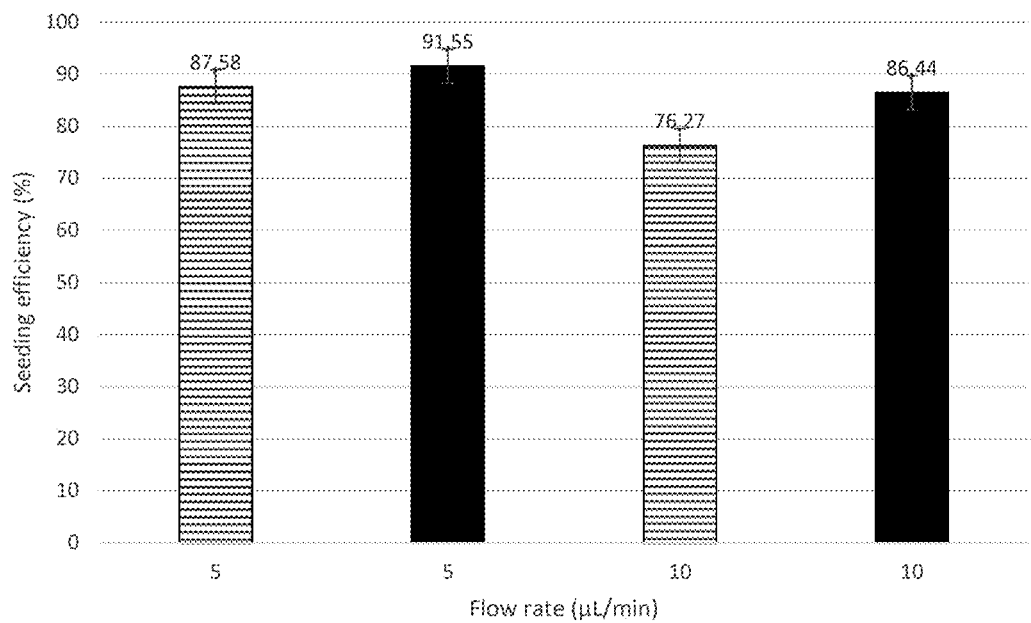
FIG. 36: Fitted results of the two level full factorial block DOE of seeding efficiencies with flow rate of 5 and 10 µL/min and a bead concentration of 2.5 and $5 \times 10^7$ beads/mL.

FIG. 36: Fitted results of the two level full factorial block DOE of seeding efficiencies with flow rate of 5 and 10 µL/min and a bead concentration of 2.5 and $5 \times 10^7$ beads/mL.

Figure 37:
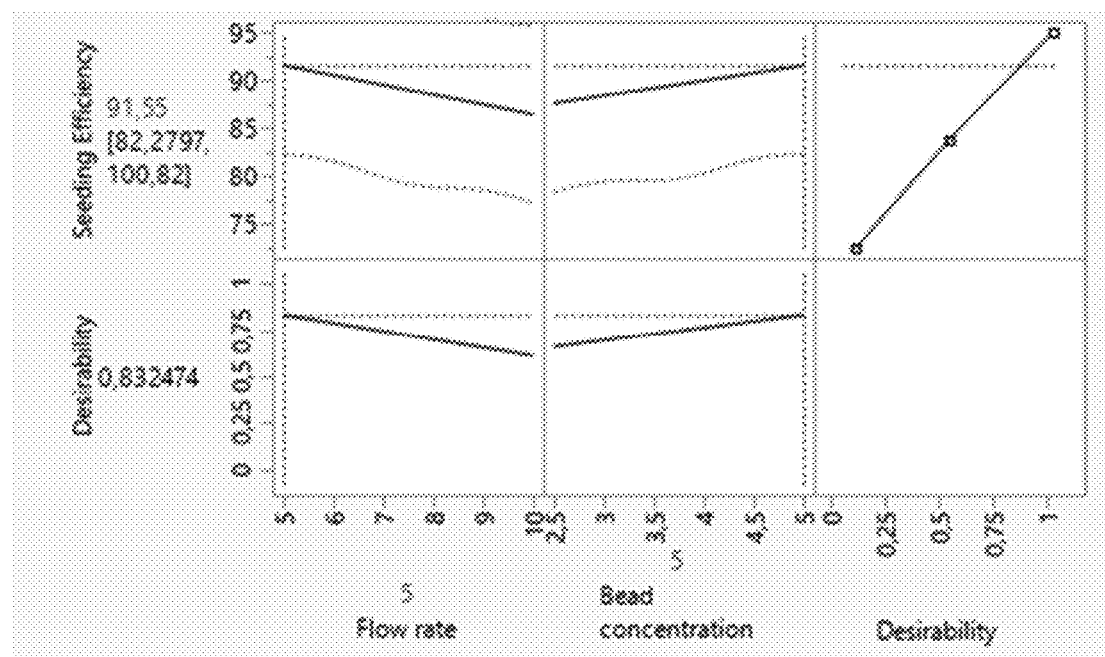
FIG. 37: Prediction profiler set at maximal seeding efficiency in which a seeding efficiency of 91.55% is predicted at settings of 5 µL/min and $5 \times 10^7$ beads/mL.

FIG. 37: Prediction profiler set at maximal seeding efficiency in which a seeding efficiency of 91.55% is predicted at settings of 5 µL/min and $5 \times 10^7$ beads/mL.

Figures 38A, 38B:
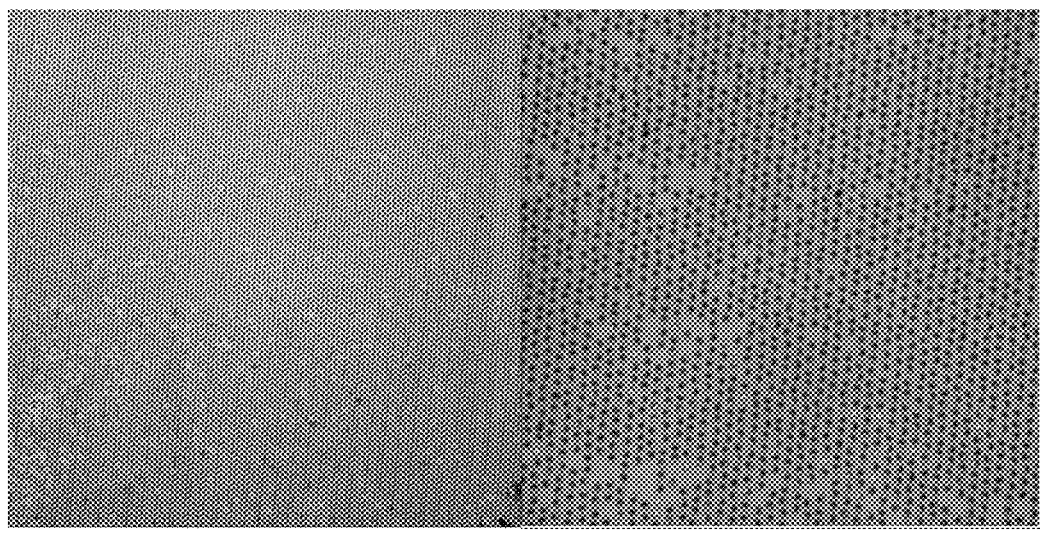
FIGS. 38(A) and 38(B): Brightfield images of seeded beads into the microwell array using the suction pump as pumping mechanism.

FIGS. 38(A) and 38(B): Brightfield images of seeded beads into the microwell array using the suction pump as pumping mechanism: FIG. 38(A) brightfield pictures taken of one array with 15x objective, and FIG. 38(B) pictures taken of second array with some defaults with 40x objective both showing seeding over 92%.

Figure 39A:
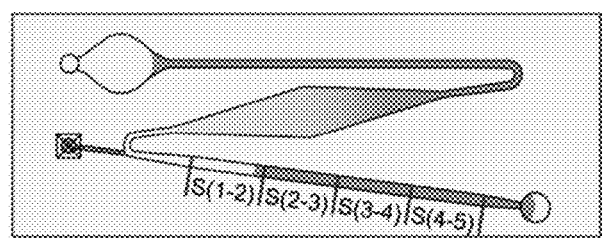
FIG. 39(A) iSIMPLE pump during the operation.
Figure 39B:
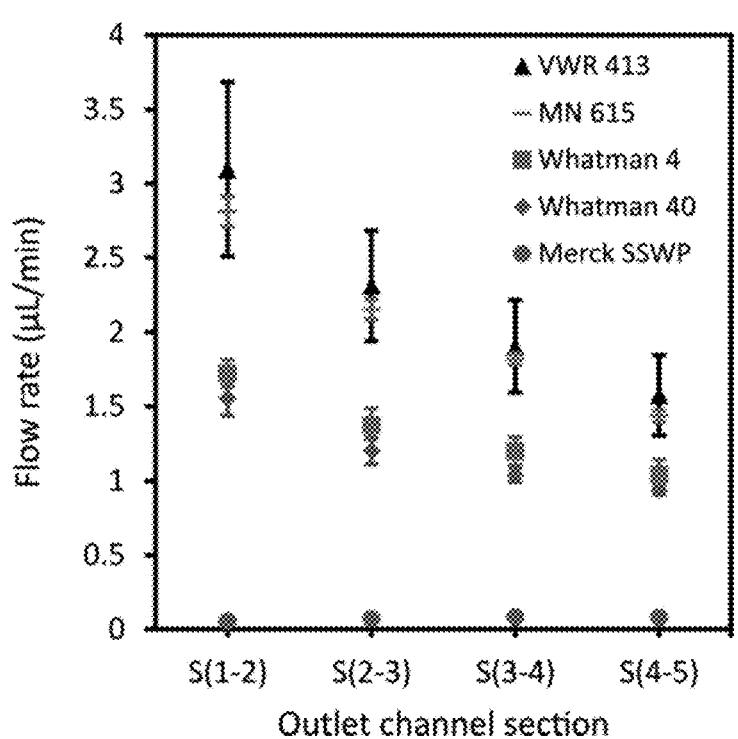
FIG. 39(B) flow rate of the outlet liquid in the different sections for different filter papers.

FIG. 39(A) iSIMPLE pump during the operation. Marks on the side of the outlet channel define equal sections of the outlet channel, each 2.3 µL. FIG. 39(B), the graph depicts the flow rate of the outlet liquid in the different sections for different filter papers. Each point represents the average flow rate values obtained from three independent experiments (error bars represent one standard deviation).

Figure 40A:
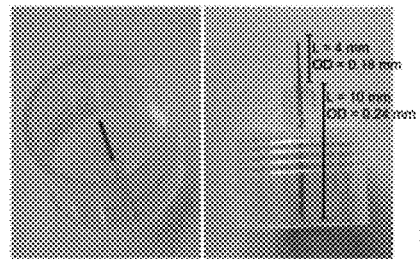
FIG. 40(A) Terumo Nanopass 34 G (0.16 mm) microneedle with internal and needle dimensions.
Figure 40B:
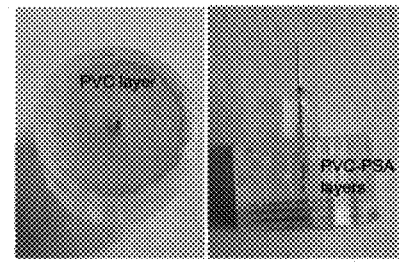
FIG. 40(B) Modified needle housing.
Figure 40C:
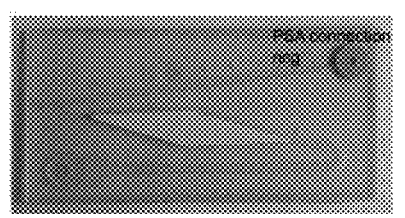
FIG. 40(C) iSIMPLE chip used for drug delivery experiments.
Figure 40D:
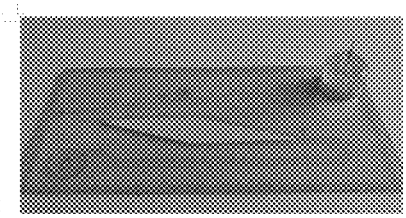
FIG. 40(D) Ready-to-use iSIMPLE chip with the integrated microneedle

FIG. 40(A), Terumo Nanopass 34 G (0.16 mm) microneedle with internal (i.e. within the plastic housing) and external (i.e. outside the plastic housing) needle dimensions. FIG. 40(B), modified needle housing where PSA and PVC layers were used to fill the void space and provide a flat interface. FIG. 40(C), iSIMPLE chip used for drug delivery experiments with the connection ring made of PSA attached on the outlet hole. FIG. 40(D), ready-to-use iSIMPLE chip with the integrated microneedle.

Figure 41:
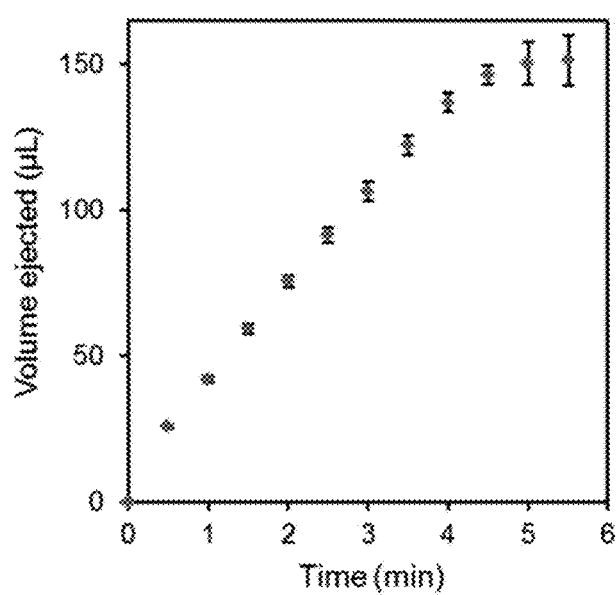
FIG. 41: Volume ejected at the corresponding time during the pump operation.

FIG. 41: The graph shows the volume ejected at the corresponding time during the pump operation. Each point represents the average ejected volume obtained from four independent experiments (error bars represent one standard deviation). More than 150 µL was ejected in 5 min before the pump stopped due to saturation of the porous material with working liquid.

Figure 42:
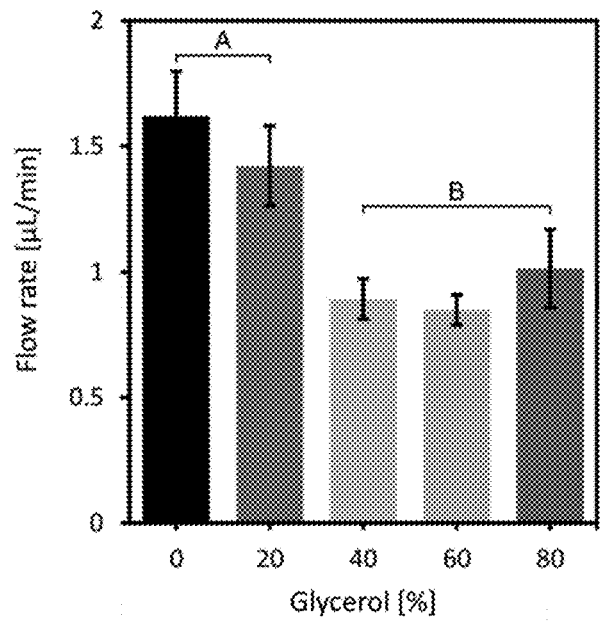
FIG. 42: Viscosity test with iSIMPLE.

FIG. 42: Viscosity test with iSIMPLE. The chart presents the flow rate for different glycerol concentrations ejected from 34 G (0.16 mm) microneedle with iSIMPLE. Each bar represents the average flow rate over section 1 to 5 of the iSIMPLE outlet channel, obtained from three independent experiments (error bars represent one standard deviation). Bars labelled with A and B are statistically different at alfa ≤0.0001.

Figure 43:
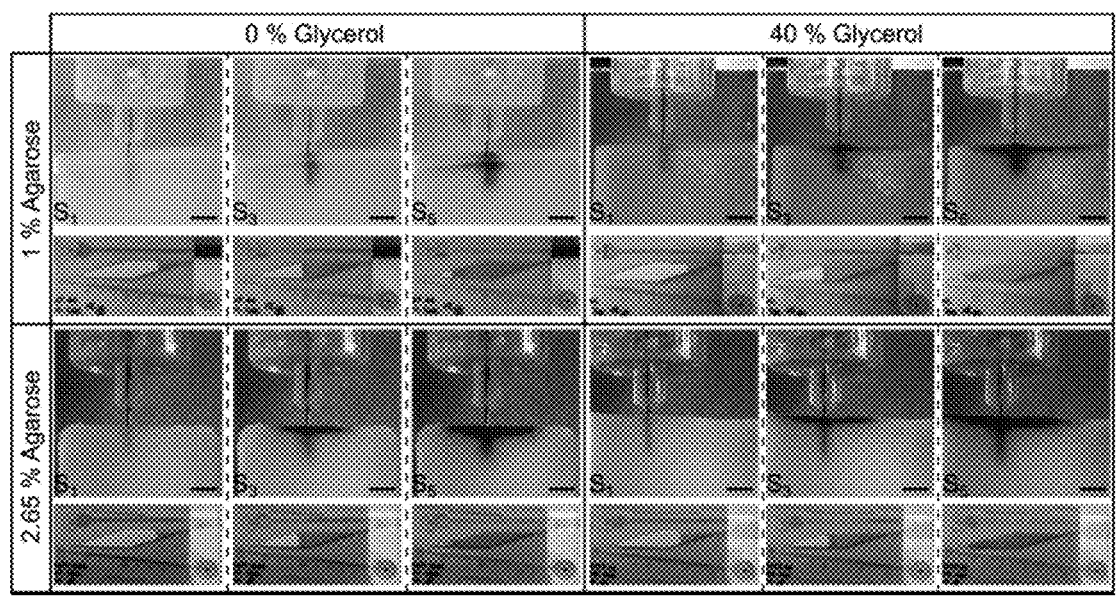
FIG. 43: Overview of injecting different glycerol concentrations (0 and 40%) in different agarose matrices (1 and 2.65%) with iSIMPLE.

FIG. 43: Overview of injecting different glycerol concentrations (0 and 40%) in different agarose matrices (1 and 2.65%) with iSIMPLE. For each combination, magnification of the microneedle and agarose (top) and iSIMPLE pump operation (bottom) are displayed when the outlet liquid reached sections S1, S3, S5 marked on the outside of the outlet channel (as described in FIG. 4A). In total, 15 µL of outlet liquid was injected in the agarose matrix in each experiment. Scale bars represent 2 mm.

Figure 44:
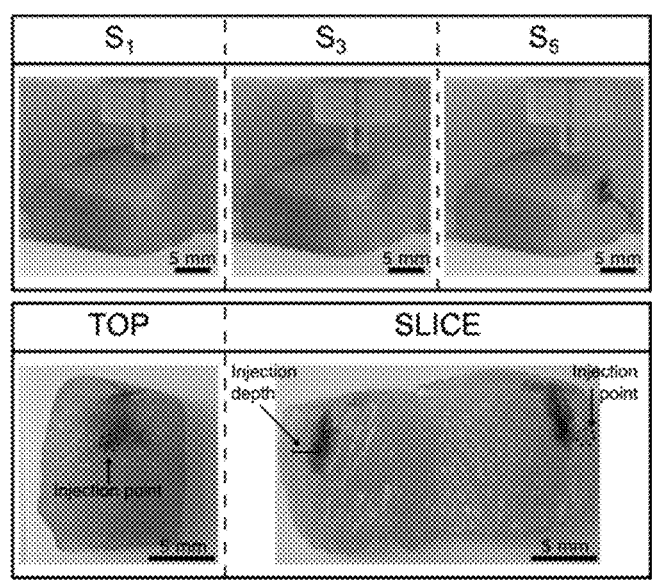
FIG. 44: Injection in chicken breast with iSIMPLE.

FIG. 44 illustrates the Injection in chicken breast with iSIMPLE. The iSIMPLE operation is shown right after activation, when the outlet liquid reached section 1 (S1), half way operation, corresponding to section 3 (S3), and at the end of the pumping, when the outlet liquid reached the last section (S5). Top view of the chicken cube after the injection, indicating the point of needle insertion. The cube was sliced in half in correspondence of the injection point and the injection depth (2 mm) is indicated.

Figure 45A:
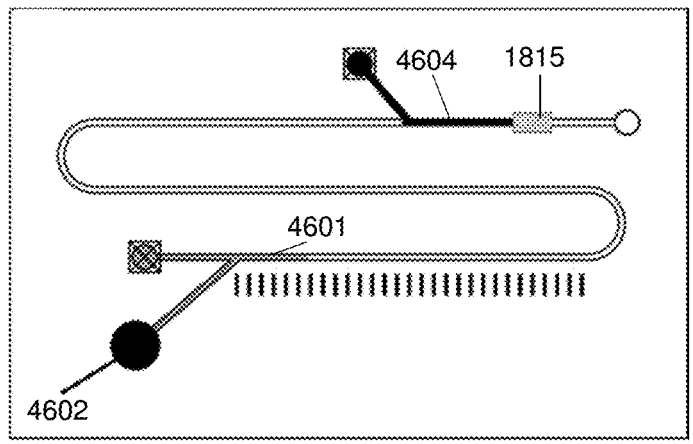
FIGS. 45(A) to 45(C) show, in three steps, the characterization of the burst pressure of a hydrophobic barrier.
Figure 45B:
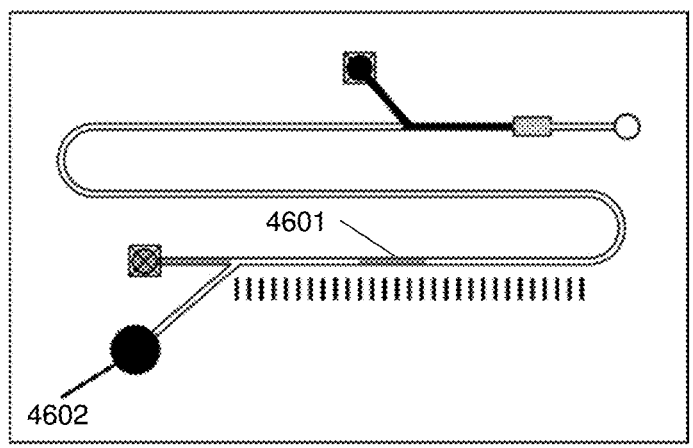
Figure 45C:
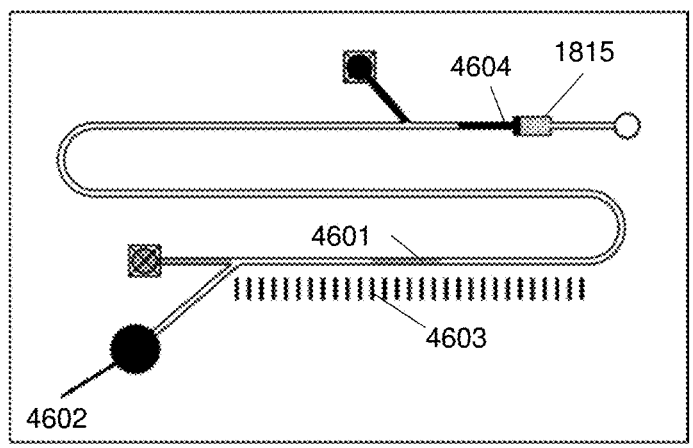

FIGS. 45(A) to 45(C) illustrate the burst pressure characterization of hydrophobic barrier. FIG. 45(A), overview of the microfluidic chip used to calculate the maximum pressure bearable by the developed hydrophobic barrier 1815. FIG. 45(B), the displacement of a measuring plug 4601, due to actuation of a syringe pump 4602, was monitored and quantified using the markings 4603 on the side of the channel. The sample 4604 was blocked by the hydrophobic barrier 1815. FIG. 45(C), when the pressure generated between the measuring plug 4601 and the sample 4604 reached the burst pressure of the hydrophobic barrier, the sample overcame the latter and continued towards the outlet. Scale bars markings 4603 represent 5 mm.

Figure 46:
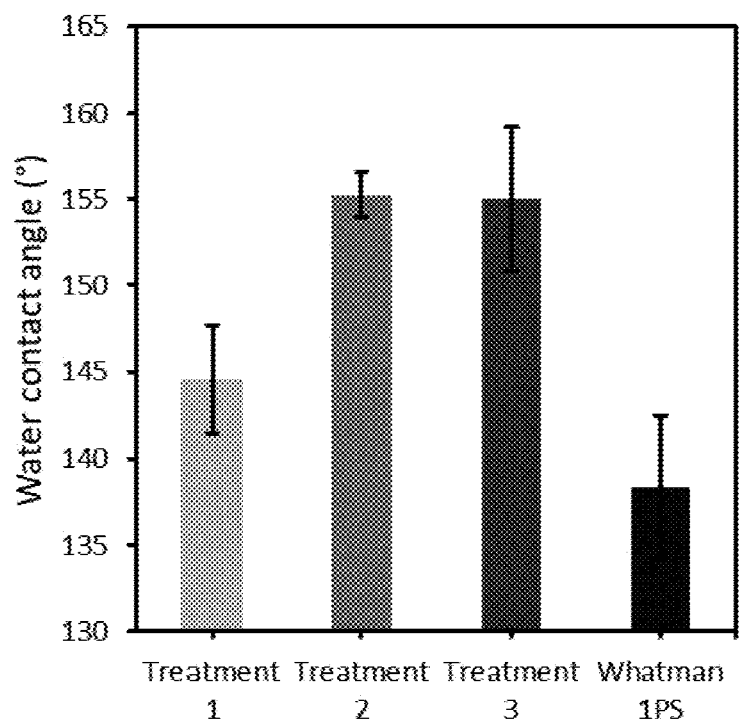
FIG. 46 illustrates measurements of the contact angle of water in contact with hydrophobic filter paper.

FIG. 46 illustrates the water contact angle measurements of hydrophobic filter paper. The average contact angle value is displayed based on measuring four water droplets per each sample (treatment 1, 2 and 3) and the reference Whatman 1PS filter paper. Error bars represent one standard deviation.

Figure 47:
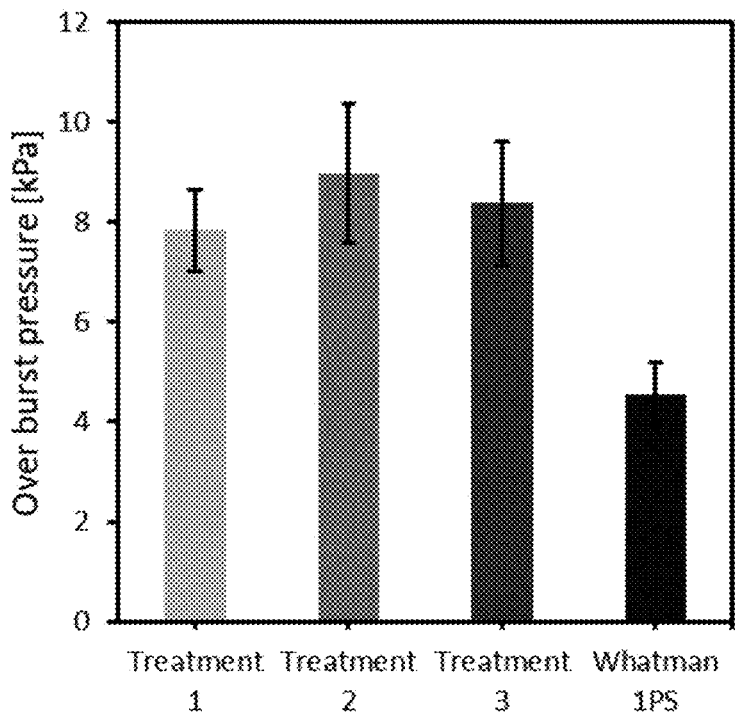
FIG. 47 shows a graph with the results of burst pressure characterization of hydrophobic valve (e.g. its hydrophobic material) used as hydrophobic barrier.

FIG. 47 illustrates the results of burst pressure characterization of hydrophobic valve used as hydrophobic barrier (e.g. a patch including hydrophobic material used as barrier). Each bar represents the average burst pressure, obtained from three independent experiments for each treatment of Whatman 43 with different amounts of Aquapel. Whatman 1PS was used as benchmark. Error bars represent one standard deviation.

FIGS. 48(A) and 48(B) illustrate the use of a hydrophobic vent to improve the iSIMPLE activation robustness. In this example, a case in point of failure of activation is shown in a device with no hydrophobic valve. FIG. 48(A) i: previous iSIMPLE design with WL and outlet liquid prefilled in their chambers. V1 represents the volume of WL in the activation zone, which must be larger than the volume of air between the WL and the porous material (V2). ii: pump activation step where a pressure with a finger is applied on the activation zone of the WL chamber, putting in contact the WL with the porous material. iii: example of failed activation due to improper activation movement, pressure or duration. FIG. 48(B) i: iSIMPLE design with hydrophobic vent and an enclosed air pouch positioned before the WL. ii: by applying a pressure with a finger on the air pouch, the WL surpass the hydrophobic vent (e.g. the valve) and comes in contact with the porous material, activating the pump. iii:

successful pump activation, irrespectively of the activation movement, due to the hydrophobic vent-based system. Scale bars represent 5 mm.

Figure 49A:
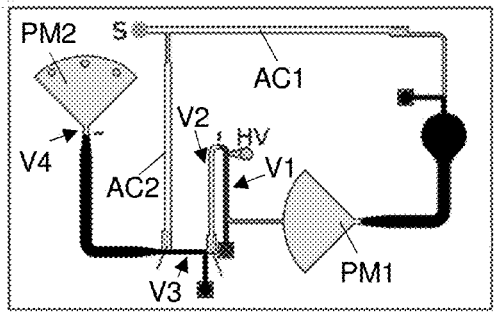
FIGS. 49(A) to 49(E) illustrate a microfluidic system (SIMPLE design) for sample splitting towards multichannel analysis. It also provides a drawing of the phases of the activation of a pulling pump and the splitting of the sample.
Figure 49D:
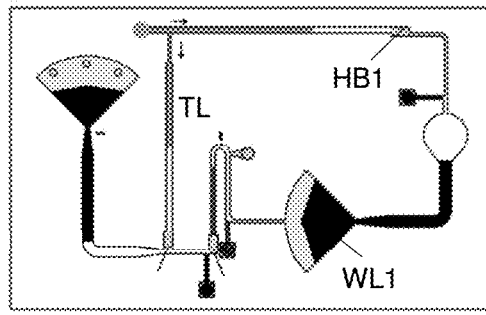
Figure 49B:
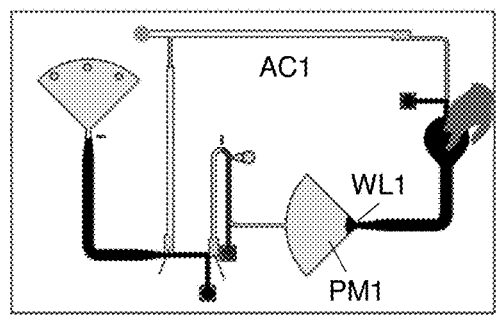
Figure 49E:
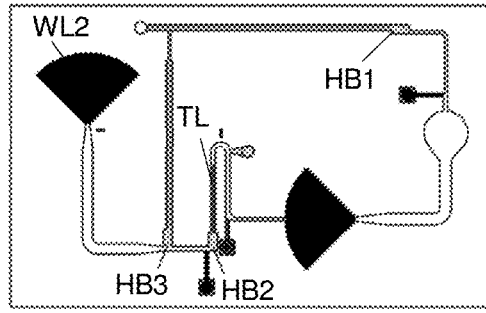

FIGS. 49(A) to 49(E) illustrate SIMPLE-based chip for sample splitting towards multichannel analysis. FIG. 49(A), overview of all the elements present in the chip. Different volumes are indicated on the chip in red: TL before the hydrophobic vent (V1); air between the TL front and the hydrophobic barrier 2, included the air in the PB pores (V2); WL between the hydrophobic barrier 2 and the hydrophobic barrier 3 (V3); air between the WL 2 and the PM 2 (V4). FIG. 49(B), SIMPLE 1 was activated and FIG. 49(C) pulled the S in the AC 1. FIG. 49(D), SIMPLE 1 activated SIMPLE 2 through a trigger system made of hydrophobic vent (e.g. including a hydrophobic vent), PB and hydrophobic barrier. FIG. 49(E), while SIMPLE 1 continued to pull the S into the AC 1, SIMPLE 2 also drew the S in the AC 2. F) SIMPLE 1 and 2 stopped. Scale bars represent 5 mm.

Figure 50A:
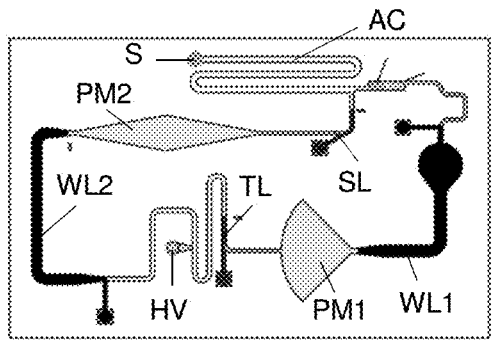
FIGS. 50(A) to 50(G) illustrate a combination of SIMPLE and iSIMPLE designs with hydrophobic valve, hydrophobic barrier and porous barrier for shuttling of liquid on chip.
Figure 50E:
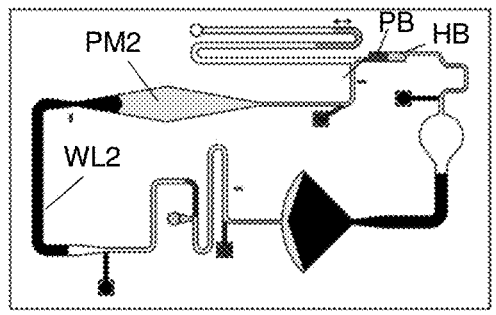
Figure 50B:
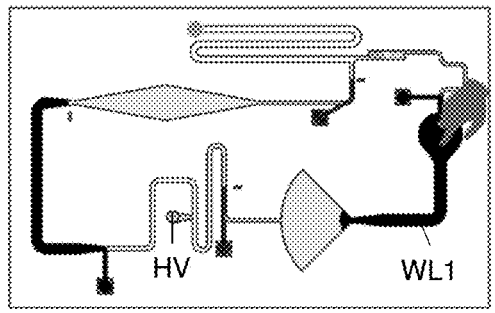
Figure 50F:
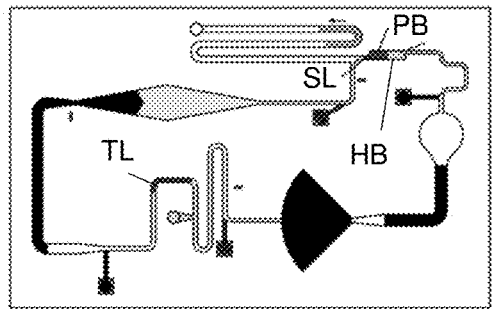
Figure 50C:
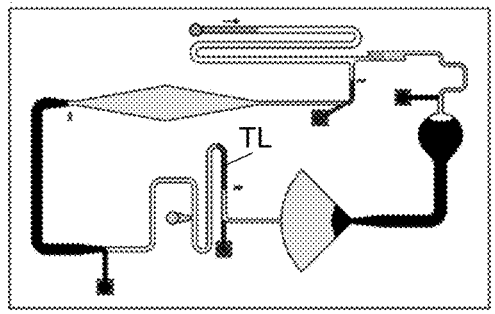
Figure 50G:
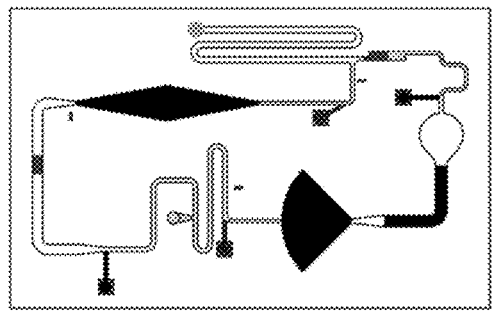
Figure 50D:
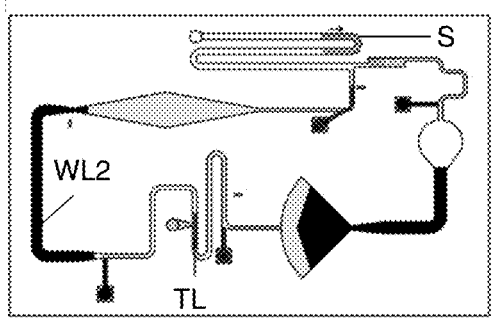

FIGS. 50(A) to 50(G) illustrate a combination of SIMPLE and iSIMPLE with hydrophobic vent, hydrophobic barrier and PB for shuttling of liquid on chip. The forward and backwards movement of the liquid sample S is explained with reference to steps A) to G). FIG. 50(A), overview of all the elements present in the chip. Different volumes are indicated on the chip in red: air pushed by SIMPLE before termination (V1); TL volume (V2); air between the TL front and the hydrophobic vent interface (V3); air between the WL 2 and the PM 2 (V4). FIG. 50(B), SIMPLE was activated and pulled the S in the AC. FIG. 50(C), SIMPLE activated iSIMPLE through a trigger system made of (or comprising) a hydrophobic vent and TL. FIG. 50(D), the SL, pushed by the iSIMPLE, was absorbed by a PB and blocked by a hydrophobic barrier, terminating the SIMPLE. FIG. 50(E), iSIMPLE pushed the S back through the AC. FIG. 50(F), iSIMPLE terminated. Scale bars represent 5 mm.

Figure 51:
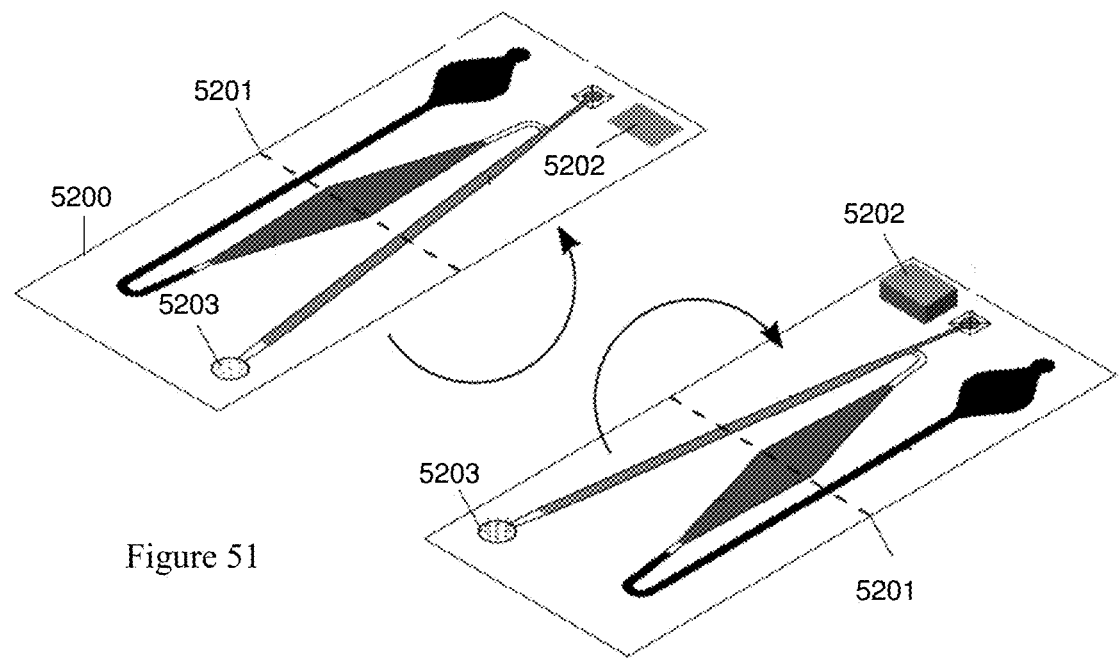
FIG. 51 illustrates an embodiment of a system with a safe disposal, needle disable feature.

FIG. 51: Safe disposal, needle disable feature. A fold-line 5201 in the disposable patch 5200 to enable the user to fold or bend the patch over the needle or microneedle array 5203 thereby sequestering the sharp end(s) of the needle or microneedle array within the patch device. The fold line 5201 provides that the (micro)needles 5203 are embedded in a needle absorbing layer 5202 upon folding of the patch device along the fold line. The needle absorbing layer 5202 accommodates or otherwise sequesters the microneedles 5203 and secures them in place. The needle absorbing layer 5202 is designed such that the height of the needle absorbing layer relative to the surface of the device matches or slightly exceeds the height of the corresponding needle or microneedle array 5203 that is to be sequestered. The needle absorbing layer may be composed of any of the suitable polymer materials that are soft enough to be pierced by the sharp ends of needle or microneedle array. The needle absorbing layer may additionally be coated with an adhesive layer, such that contact to the needle or microneedle array results in a physical bond between the needle absorbing layer and the needle or microneedle array.

Figure 52:
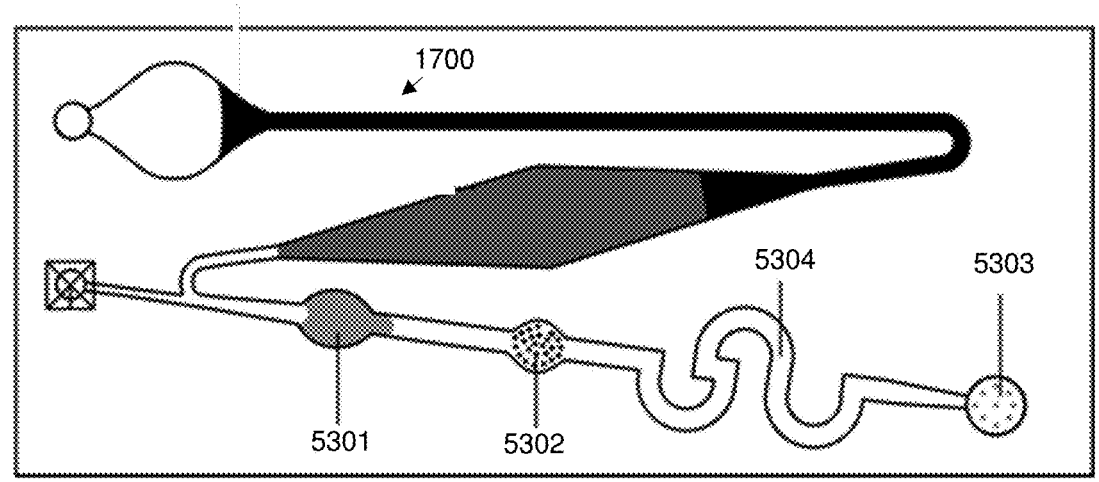
FIG. 52 illustrates an embodiment with multi-chamber/ one-step reconstitution on the device.

FIG. 52: Multi-chamber design/one-step reconstitution on the device. In another embodiment, the (iSIMPLE) propulsion pump allows for the implementation of one-step, on-device reconstitution of active pharmaceutical ingredients, whereby at least one of the components of the active pharmaceutical ingredient or vaccine is a liquid component and at least one other ingredient is a solid component such as a lyophilized vaccine or drug. Due to the ability of the (iSIMPLE) propulsion pump to generate high pressures in microfluidic channels and chambers, the design of a multi-chamber device is enabled. In this design, at least one chamber 5301 contains a liquid component, this said chamber is connected by an adjacent channel to at least one other chamber 5302 that contains a liquid or solid component that together with the first said liquid component constitute an active pharmaceutical ingredient or vaccine. Upon activation of the (iSIMPLE) propulsion pump 1700, the first liquid component is propelled under pressure through a connecting channel to a second liquid or solid component. Upon contacting the second solid component, the first and the second components mix, or otherwise the second solid component is dissolved in the first liquid component and the resulting reconstituted mixture is further propelled along a channel connected to a needle or microneedle array 5303. In order to ensure adequate mixing of the reconstituted components, a "mixing zone" 5304 may be included in the channel connecting the second component and the microneedle array 5303.

Figure 53:
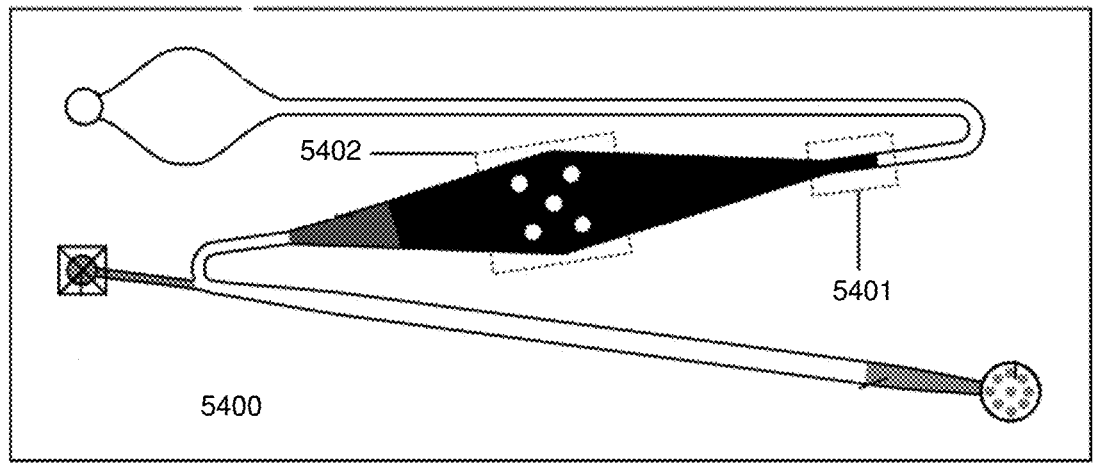
FIG. 53 illustrates an embodiment including features for monitoring of pump function/termination of injection feature/Barcoding/compliance/traceability system.

FIG. 53: Barcoding/compliance/traceability system Monitoring of pump function/termination of injection feature is possible via a passive indicator to inform the user on the successful completion of operation of the pumping mechanism of the disposable patch device 5400. In one embodiment this is achieved by adding a visible color dye to the working liquid, and providing a transparent layer 5401 in part of the device, such that the transparent layer is positioned on top of a channel that houses the working liquid, and makes visible the passage of the working liquid in the said channel. The user is informed of the termination of the working of pumping mechanism, and thereby the successful completion of the working operation of the device when the working liquid completely passes the channel visible through the transparent layer. In another embodiment, the porous material (or a portion 5402 thereof) that comprises either the (iSIMPLE) propulsion pump or the (SIMPLE) capillary pump can be printed with a suitable reactive substance that in an anhydrous form is white or colorless, but that produces a color reaction upon contact with the aqueous working liquid. For example such reactive substance can be anhydrous copper sulfate. Upon saturation of the porous material, the reactive substance turns a visible color. The printed reactive substance can be applied in a pattern that would be unique to each disposable chip. Such pattern can be in the form of a barcode, a dot code or any other form of 2 dimensional matrix symbol codes. Upon hydration of the porous material and the printed reactive substance, the reactive substance can develop into a unique readable code as a priori assigned during the printing process of the reactive substance on the porous material. A transparent layer can then be positioned on top of the porous material containing the printed code to be made visible to the user or be read-off by image acquisition and processing systems. The image acquisition and processing system that reads-off the unique code, such as a smart phone, can then send the result of the read-off to a central information storage and processing system, such as a cloud based ICT system. The result of the read-off can be accessed through the central information storage system by for example medical professionals to confirm that the device has been used as intended. Such a system can, for example, be used to monitor patient compliance to prescribed medications.

Figure 54:
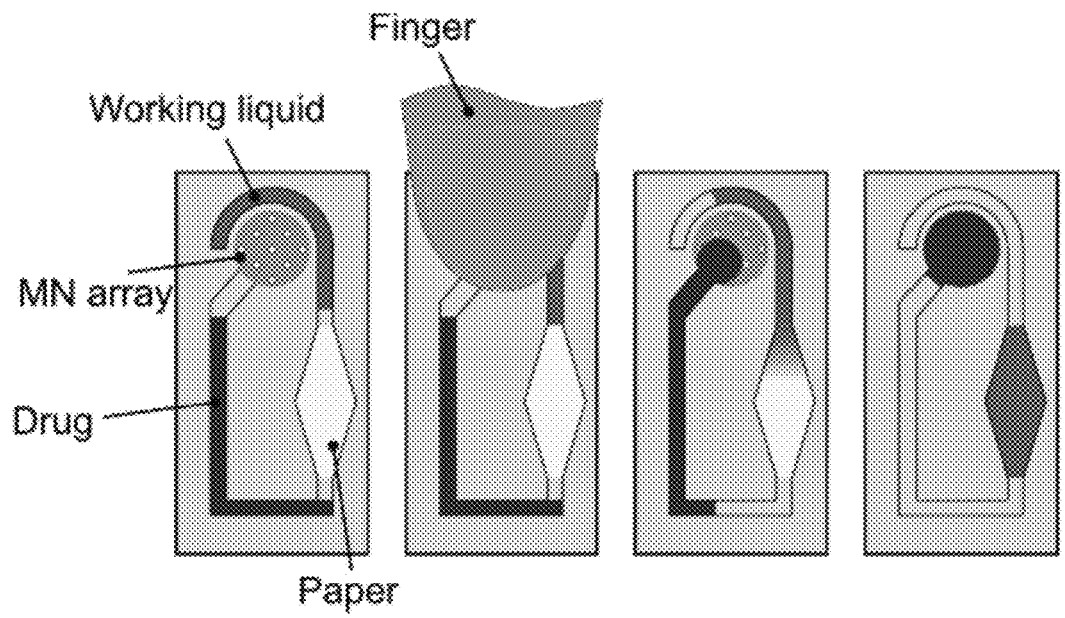
FIG. 54 illustrates a pump activation and (micro)needle application "button".

FIG. 54: A pump activation and (micro)needle application "button". In one embodiment, the (iSIMPLE) microneedle drug or vaccine delivery device is designed such that the physical force, such as a finger push, that is applied used to activate the propulsion pump is also useful to provide the mechanical force to push or insert the needle or microneedle array into the skin. This can be achieved by positioning the activation button for initiation of the population pump on top on of the needle or microneedle array. Such button could be configured to be "activatable" only through sufficient force, to prevent premature activation and to allow positioning of the device on skin prior to activation. As an example of a such configuration, the activation button could be a domed diaphragm that is depressible only when a certain sufficient force is applied, by for example, finger pressure.

It is to be noted that the embodiments shown in FIGS. 51, 52, 53 and 54 may further include a unit with a vent hole, e.g. a hydrophobic valve, according to embodiments of the present invention, placed along the conduit, in order to provide robust actuation. For example, these embodiments may include a hydrophobic valve 1706 as shown in FIGS. 17(A) to 17(D)

Description

EXAMPLES

Example 1: Fabrication of a Propulsion Pump According to the Present Invention Using Double-Sided Pressure Sensitive Adhesive and Filter Paper as Solid Sorbent Materials and Reagents Double-sided pressure sensitive adhesive (PSA) tape (200MP 7956MP) and adhesive transfer tape (467MP) were acquired from 3M (USA). Two different thickness of PVC transparent foils (180 µm or 300 µm) were tested. Filter papers with different pore sizes (0.22-13 µm) (413, VWR, Belgium; SSWP, RAWP, HATF, HVLP, GSTF, Merck Millipore, Belgium) were used. Poly(methyl methacrylate) (PMMA) plate, 2 mm thick, was shaped with laser cutter. A digital tabletop craft cutter (Cameo, Silhouette, USA) was used to cut all the PSA, filter paper and PVC foil elements of the microfluidic device. A digital camera (D3200, Nikon, Japan) with a zoom lens (AF-S DX Zoom-NIKKOR 18-55 mm f/3.5-5.6G ED II, Nikon, Japan) was used to video record the experiments.

Different filter papers used are specified in Table 1.

TABLE 1

Properties of the filter papers. Particle retention represents the typical particle size that is retained by the paper matrix. All the thickness values have been provided by the manufacturer, except for the one marked with an asterisk, which was internally measured.

| Company | Product # | Thickness [µm] | Particle retention [µm] | Filtration speed | Material |
|---|---|---|---|---|---|
| VWR | 413 | 150* | 5-13 | medium | cellulose |
| Whatman | Grade 4 | 210 | 25 | very fast | cellulose |
| Whatman | Grade 40 | 210 | 8 | medium | cellulose |
| Whatman | Grade 113 | 420 | 30 | very fast | cellulose |
| Macherey-Nagel | 615 | 160 | 4-12 | medium-fast | cellulose |
| Merck Millipore | SSWP | 150 | 3 | NA | mixed cellulose |
| Merck Millipore | HVLP | 125 | 0.45 | fast | PVDF |

Device Fabrication

The microfluidic device was fabricated according to the low-cost and rapid prototyping method presented in Yuen et al. and Kokalj et al.[1,8] A digital craft cutter was used to obtain the microfluidic channel in the PSA layer. Using this simple, cheap and fast fabrication method, a device with channel width down to 400 µm was obtained in a reproducible way. Microfluidic channel height was determined by the PSA thickness, in our case 6 mils (around 152 µm). The PSA layer was sandwiched between a bottom and a top PVC layers, where the top layer was designed with inlet, outlet and vent-holes. Filter paper, shaped with the digital craft cutter, was inserted into the porous material chamber during the fabrication. For specific applications, adhesive transfer tape was used to seal the porous material to the top and bottom PVC layers. For the pressure measuring system of FIGS. 6(A) to 6(D) a PMMA plate was attached to the bottom PVC layer to increase the robustness of the device. The four basic elements of a propulsion pump of embodiments of the present invention, were assembled together as shown in FIGS. 3(A) to 3(C).

Device Prefilling

After the fabrication, the devices were prefilled for an immediate use or long-term storage. The working liquid and the outlet liquid were injected in the respective chambers manually or with a syringe pump (PHD2000, Harvard Apparatus, USA). A Teflon tube was connected to one side of the syringe via HPLC connector (Peak Finger Tight Fitting, Perkin Elmer, Belgium) and to the other side to a custom made PMMA adapter which was pressed onto the injection channel opening for precise filling of the chamber (FIGS. 4(C) and 4(D)). Blue and red food color dyes were diluted in distilled water and used respectively as working liquid and outlet liquid in our experiments. During the prefilling step, a vent-hole connected to the porous material chamber was needed to inject the outlet liquid in its channel. In this way, the air present in the outlet channel was replaced by the outlet liquid and expelled through the vent-hole without pushing back the working liquid (FIGS. 4 (E) and 4(F)). Once the device was prefilled, the vent-hole was closed with a PSA patch (FIGS. 4 (G) and 4(H)).

Example 2: Operation of an Embodiment of a Propulsion Pump Fabricated According to Example 1

The mechanism underlying the operation of the propulsion pump according the previous examples the porous material used as solid sorbents, such as a filter paper have a given wherein the pores are filled with a gas, typically air. If the porous material is placed between the inlet and outlet of a microfluidic system, when a liquid present in the inlet side of the circuit, namely working liquid, gets in contact with the porous material, the working liquid is absorbed. At the same time, it pushes the air out of the porous material into the outlet channel. If the outlet channel is prefilled with an outlet liquid, the latter is pushed by the air towards the outlet of the microfluidic device. FIGS. 5(A) to 5(D) provide a step by step illustration of a propulsion pump according the present invention.

Example 3: Flow Rate of the Forward Pumped Fluid in a Propulsion Pump System According to Example 2 in Relation to the Geometry and/or Pore Size of the Filter Paper When it comes to a microfluidic system, one of the most important characteristics to take into account is the flow rate of the liquids that flow through the network. Different methods can be adopted to tune the flow rate, such as changing the channel geometry to increase or decrease the flow resistance or acting on the pumping mechanism. In the latter case for paper microfluidic solutions, it means to change paper type, shape and size. Although any water absorbing porous material could be used in the iSIMPLE concept, we selected a laboratory filter paper since its properties are well defined, it is easy to cut and it is compatible with our fabrication method.

To test this, the device was designed and prepared as described above with the overall size of the device being slightly bigger than a standard microscopy slide (35×80 mm). The size of the filter paper was constant (surface of 144.3 mm$^2$) in all the experiments and was selected to ensure enough air volume for pushing forward the outlet liquid, assuming a 70% porosity.

It was shown that flow rate is influenced by paper geometry; for instance, a circular sector with wider angle leads to a higher flow rate than with a more acute angle. We selected one particular shape of the filter paper, namely a diamond shape, as it has been shown previously that flow rate is influenced by paper geometry. The diamond shape can be seen as the combination of two specular circular sectors that provide a constant flow in the first expanding part and, in the second restriction part, ensuring a smooth transition to the outlet channel without trapping air bubbles in the porous material chamber. In the proof-of-a-concept device, the inlet channel was 1 mm wide with an expanded section that facilitates the activation of the pump with the finger. Five different filter papers were tested here (VWR 413, MN 615, Whatman grade 4, Whatman grade 40, Merck SSWP) differing in their porosity, retention capacity, and filtration speed, as detailed in Table 1. After the activation, the outlet liquid was pushed towards the outlet hole and the entire operation was video recorded for further analysis (FIG. 39(A)). Equal sections were marked on the outside of the outlet channel during the fabrication (i.e. S(1-2), ..., S(4-5)) in order to simplify the analysis and calculation of the flow rate. The flow rate of the liquid between two marks was determined by analyzing the recorded video sequences and taking into account the geometrical parameters of the device (FIG. 39(B)).

The four filter papers tested (VWR 413, Whatman grade 4, Whatman grade 40, MN 615) resulted in flow rates ranging from 3 to 1 µL/min and all showed a decrease in the flow rate along with the pump operation (FIG. 39(B)). The fifth paper tested (Merck SSWP) led to a significantly lower flow rate (0.07 µL/min on average) and much longer time (131±16 min) needed to eject the same volume (9 µL) compared to the other four: 4.48±0.73 min (VWR 413), 4.75±0.07 min (MN 615), 7.15±0.57 min (Whatman grade 4) and 8.05±0.35 min (Whatman grade 40). These experiments proved a wide range of flow rates that can be achieved with the iSIMPLE depending on the selection of porous materials. Based on the specific application, the iSIMPLE can provide faster or slower flow-rate, giving an extraordinary flexibility in liquid manipulations.

Further it was shown that the higher capillary forces associated with smaller pore sizes resulted in an increasing flow rate with decreasing pore size. Within a device set-up as shown in FIGS. 5(A) to 5(D) (example 2) it was demonstrated using video analyses that the flow rate gradually increased when using filter paper having a pore size of 5-13, 3, 1.2, 0.45, 0.22 µm, respectively.

Example 4: Testing the Pressure Generation in a Pump According to Embodiments of the Present Invention Several POC microfluidic applications (i.e. drug delivery, insulin injection) require that a sufficient pressure is generated to overcome the resistance of a barrier, for instance the skin. Currently, microfluidic pumps still require external power supply (up to hundreds of volts) to reach a limited pressure (up to few tens of kPa). Obviously these specifications do not fit the requirements of a POC device.

To show that the propulsion pump according to embodiments of the present invention can reach higher pressure without any external power, the device presented in FIGS. 6(A) to 6(D) was developed. In order to generate the highest possible pressure, a porous material with small (i.e. 0.45 µm) pore size (HVLP, see Table 1) was used, since it has been shown that the capillary pressure increases with the decreasing size of the pores. The liquid plug was as close as possible to the porous material to minimize the air volume between the two elements. In fact, this volume can be compressed during the iSIMPLE operation resulting in an underestimation of the real pressure generated. An excess of working liquid (to saturate the porous material) was added on the inlet opening. When the porous material started absorbing the working liquid, the liquid plug was pushed towards the closed end of the measuring channel compressing the air in that part of the channel.

The porous material chamber was positioned just after the inlet opening and further physically or functionally connected to the measuring channel where a liquid plug between 0.5 and 1 µl, was preloaded. After the activation of the device by adding a drop of working liquid on the inlet opening, the porous material started absorbing the working liquid and the liquid plug was pushed towards the close end of the measuring channel. This caused an increased pressure between the liquid plug and the end of the measuring channel. In this experiment, the filter paper was squeezed between two layers of transfer tape to ensure a proper sealing with the PVC top and bottom layers in the porous material chamber. This extra step in the fabrication process was needed to prevent the air, present in the porous material, from flowing back through the gap between the filter paper and the PVC layers and to prevent it from escaping by the inlet of the device due to the high pressure generated. The latter was observed when no proper sealing of the porous material in the porous material chamber was assured and resulted in a much smaller increase of pressure. Similar to the previous experiments, 300 µm thick PVC layers were used with a difference here of adding a PMMA plate with an extra layer of PSA to the bottom PVC layer in order to reinforce the device due to the pressure increase.

To correlate the displacement of the liquid plug to the change of pressure in the measuring channel, we applied Boyle's law:

$$P_2 = P_1 \frac{d_1}{d_2}$$

where the final pressure in the measuring channel ($P_2$) can be calculated knowing the initial pressure ($P_1$) and the initial ($d_1$) and final ($d_2$) distance between the liquid plug and the closed end of the measuring channel (width and height of the channel are constant). Using this theoretical model, validated in a pressure chamber and applied to the video recorded sequences of the operation, the pressure increment was measured with sufficient accuracy. The pressure increase over the atmospheric pressure as a function of time is presented in FIG. 7.

As depicted in FIG. 7, an increase of 65.3 kPa above the atmospheric pressure was achieved in 24 minutes, and kept constant after termination of the pumping until the porous material dried out. This value is higher or at least comparable to all the microfluidic pumps presented in literature, with the substantial difference that our approach is completely self-powered.

Moreover, the theoretical estimations predict that higher pressures can be achieved with the iSIMPLE by further improving the fabrication methods. For example, by achieving better contact and sealing between the porous material and its chamber, leakage of air can be completely prevented, leading to even higher pressure generation. In fact, according to Young-Laplace equation, the capillary pressure achievable by a porous material with 0.45 µm pore diameter in contact with water, is 640 kPa, which is 10 times higher than the one achieved in this work. Although the variability of the pressure generated over the same amount of time (i.e. 24 min) was relatively high (CV ~20%), this was mostly due to the limitations of the fabrication process, as mentioned above.

Example 5: A Microfluidic System Comprising a Suction Pump and a Propulsion Pump According to the Present Invention The microfluidic system was prepared using PVC foils, filter paper and a PSA layer as explained in Example 1. The Microfluidic system comprises a propulsion pump according to embodiments of the present invention having a wing-shaped solid sorbent (filter paper) operably connected to a suction pump wherein said suction pump serves as an activation means or actuator for said propulsion pump. Before its activation (FIG. 8(A)), the microfluidic system comprises a SIMPLE[1] suction pump comprising an enclosed filter paper PM1 in the shape of a circle sector. The enclosure of said filter paper comprises several vent-holes and an opening, which connects via a channel to a reservoir having a flexible or depressible wall. Said channel and reservoir comprise a working liquid and are operably connected to the propulsion pump via a channel comprising an analyte inlet (analytical zone). A droplet of a first liquid analyte A1 is placed on the inlet of the analytical channel. The enclosure of the wing-shaped filter paper PM2 of the propulsion pump comprises a first opening connecting said enclosure to the analytical channel and a second opening connecting to an outlet channel. In turn the outlet channel is physically or functionally connected to an analyte storage channel, which connects to the analytical channel. The analyte storage channel is preloaded with a second liquid analyte A2.

The suction pump is activated by compressing the reservoir comprising the working liquid (FIG. 8(B)), such that the working liquid is brought into contact with the filter paper PM1 initiating the absorption of the working liquid by the filter paper PM 1.

After activation of the suction pump (SIMPLE), the absorption of the working liquid by the filter paper PM1 results in a reduced pressure in the analytical channel whereby the droplet of the first liquid analyte A1 is drawn into in the analytical channel.

When the first liquid analyte A1 contacts the enclosed wing-shaped filter paper PM2 of the propulsion pump, it is absorbed and expulses the air from the filter paper pores into the outlet channel. This inflow of the air in the outlet channel pushes the second liquid analyte A2 from the analyte storage channel into the analytical channel. The action of the suction pump terminates when all working liquid is absorbed into the filter paper PM1 or when the filter paper PM1 is saturated by the working liquid.

The operation of the propulsion pump according to embodiments of the present invention terminates either when all first liquid analyte A1 is absorbed into the wing-shaped filter paper PM2 or when the wing-shaped filter paper PM2 is saturated by the first liquid analyte A1.

Example 6: A Microfluidic System Comprising a Suction Pump Simultaneously Activating Propulsion Pumps According to the Present Invention A microfluidic system was prepared according to the general scheme of FIGS. 9(A) to 9(E) using the material and methods of Example 1.

Example 7: A Microfluidic System Comprising a Suction Pump Sequentially Activating Propulsion Pump According to the Present Invention A microfluidic system was prepared according to the general scheme of FIGS. 10(A) to 10(F) using the material and methods of Example 1.

Example 8: A Microfluidic System Comprising a Suction Pump being Activated by a Propulsion Pump According to the Present Invention Wherein Said Activating Pump Simultaneously Acts as a Suction Pump A microfluidic system was prepared according to the general scheme of FIGS. 11(A) to 11(E) using the material and methods of Example 1.

Example 9: Microfluidic System Comprising Two Propulsion Pumps According to the Present Invention Wherein One Propulsion Pump Activates the Other and Wherein Said Activating Pump Also Acts as a Suction Pump A microfluidic system was prepared according to the general scheme of FIGS. 12(A) to 12(F) using the material and methods of Example 1.

Example 10: Microfluidic Assay System Comprising Two Propulsion Pumps According to the Present Invention Combined with a Suction Pump A microfluidic assay system was prepared according to the general scheme of FIGS. 13(A) to 13(F) using the material and methods of Example 1.

In a specific embodiment the microfluidic assay system of this Example 10 involves a detection system comprising silver enhancement of captured gold coated nanoparticles as previously described. The reference DZ, S, WB, R1, R2, WB, MZ as used below refer to the corresponding items in FIGS. 13(A) to 13(F). The goal of this bioassay is to capture gold nanoparticles (AuNPs) functionalized with streptavidin contained in a sample (S) on a surface (detection zone, DZ) pre-functionalized with biotinylated antibodies. In order to generate a signal that can be detected with bare eyes (for qualitative detection, i.e. yes/no) or with a photodiode (for semi-quantitative detection), a silver enhancement was performed. Silver solution (made of mixed reagent 1 (R1) and reagent 2 (R2)) is brought over the detection zone (DZ), and catalyzed by the AuNPs, it forms an opaque dark layer. For semi-quantitative detection, an electrical circuit comprising a LED, a photodiode and a microcontroller is used (FIG. 14) to measure the intensity loss of LED light due to reflection of the silver layer. Only the light that pass through was picked up by a photodiode and this information was processed by the microcontroller, which then displayed the result of the test on an LCD screen. So the less light the photodiode receives, the darker and thicker the silver layer is, due to higher concentration of AuNPs. The immobilisation of biotinylated hIgE antibodies on the PMMA bottom plate within the detection zone (DZ) was done by physisorption. Concentration of streptavidin-AuNPs was optimized and 1:20 dilutions from stock concentration was used to maximize signal generation avoiding at the same time clustering of nanoparticles. The silver enhancement protocol was adapted from Hacker et al. (1988). The Reagent 1 (R1) (100 mg of silver acetate in 25 ml water) and Reagent 2 (R2) (125 mg of hydroquinone in 25 ml citrate buffer pH 3.8) cannot be premixed before the incubation in the detection zone and for this reason they were separately prefilled in the respective chambers (R1, R2). A washing step was performed between the Strep-AuNPs incubation (15 minutes) and the Silver mix incubation (30 minutes), by pumping a washing buffer (WB) that was prefilled in the mixing zone (MZ) of the microfluidic assay system, to remove unbounded AuNPs from the detection zone.

Example 11: Microfluidic Assay System Comprising Two Propulsion Pumps According to the Present Invention Combined with a Suction Pump A microfluidic assay system was prepared according to the general scheme of FIGS. 15(A) to 15(D) using the material and methods of Example 1 and as further specified in the legend to FIGS. 15(A) to 15(D).

In this specific example, the goal was to detect the presence of creatinine in plasma with an enzymatic reaction and a spectrophotometric readout. More particularly a plasma sample S comprising spiked creatinine was mixed with reagents (R1 and R2) during the microfluidic assay procedure. Both R1 and R2 comprise a creatinine probe, creatinase, creatininase and creatinine enzyme mix as available in the Sigma Aldrich creatinine assay kit (Catalog number: MAK080). The sample S was diluted in the reagents R1 and R2 in a 1:8 ratio and was subsequently mixed with said reagents by passage through the mixing zone MZ. In a specific embodiment 5 µl of S was diluted in and mixed with 17.5 µl of both R1 and R2. The height of the detection zone DZ of a microfluidic device according to this example is preferably higher than that of the other parts of the microfluidic system, for instance through the use of multiple stacked layers of double side tape, in order to obtain an increased path length facilitating spectrophotometric detection. In a particular embodiment the microfluidic network other than the DZ had a height of 254 µm, while the height of detection zone was 508 µm. Preferably both the top and bottom layer enclosing the detection zone are transparent or translucent.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Example 12: Microfluidic Capillary Propulsion Pumps and Capillary Suction Pump Injection Device for Delivering of Bioactive Molecules Nanopass 34 G (0.16 mm) microneedles were acquired from Terumo (Belgium). Glycerol bidistilled 99.5% and agarose powder were acquired from VWR (Belgium) and Melford (UK), respectively. Chicken breast was acquired at the local butcher.

In order to evaluate the compatibility of the iSIMPLE with drug delivery applications, a microneedle was connected to the iSIMPLE. Nanopass 34 G (0.16 mm) (Terumo, Belgium) microneedle was selected since it is the smallest microneedle available on the market (external length (i.e. length outside the plastic housing): 4 mm, eternal outer diameter (OD): 0.18 mm, external inner diameter: 0.08 mm). To make the integration with the iSIMPLE chip possible, the plastic housing of a microneedle was first modified. Briefly, the void space between the larger part of the needle and the plastic housing was filled with multiple PSA and PVC layers and everything was sealed with super glue. This modification provided a flat surface which was connected to the outlet hole on the iSIMPLE via a connection ring made of PSA (FIG. 41). This connection provided a fast and easy but robust and leakage free sealing between the microfluidic chip and the microneedle.

A capillary propulsion pump (so called iSIMPLE) had been coupled to microneedles to inject a tissue of present invention for drug delivery. This iSIMPLE 7000 was provided with hydrophobic valve (as displayed in FIGS. 17(A) to 17(D). In the initiation the working liquid (WL) and outlet liquid (OL) were preloaded in the respective chambers while a porous material (PM) was housed in its chamber during the fabrication. A hydrophobic valve (HV 7001) comprising a filter paper treated to become hydrophobic, was positioned on a side of the WL chamber, for example in a cavity with a vent hole, forming the gas-permeable liquid-sealed unit with vent hole and connected to the WL chamber via a shunt conduit, after the WL prefilling point. The other side of the HV is open to the air. A needle or microneedle is coupled to the outlet of the outlet channel. The system was activation by pushing on the activation zone, the WL gets in contact with the PM and overcome the HV interface. During operation the WL is absorbed into the PM, it pushes out the air present in the PM. This air pushes the OL out of the needle/microneedle. The HV lets the air enter in the WL reservoir to replace the WL absorbed by the PM. The propulsion pump (so called iSIMPLE) is terminated either when all WL is absorbed into the PM or when the PM is saturated by the WL. The needle/microneedle was connection to the propulsion pump (so called iSIMPLE) chip. The device is shown on side view: i) bottom layer, ii) outlet channel (OC) cut in PSA, iii) top layer with outlet hole. A connection ring (CR) made of PSA is used to connect the outlet of the propulsion pump (so called iSIMPLE) chip with the inlet of the needle/microneedle.

A propulsion pump (so called iSIMPLE) chip for drug delivery assembled and prefilled with an array of five 32G (0.2 mm) needles was used for injecting in 1% agarose matrix with a red colored outlet liquid. This was injected in the matrix without liquid spoil (as can be seen in FIGS. 20(A) to 20(D)). The pressure was calculated (using Hagen-Poiseuille law) needed to eject a liquid with different viscosity (0-100% glycerol concentrations) through a needle of different diameter (i.e. 26G (0.404 mm) and 34G (0.16 mm)) at 20° C. using a flow rate of 0.8 μl/min.

Example 13: A Method of Seeding According to the Present Invention

Lodestar superparamagnetic beads (2.7 mm diameter) functionalized with streptavidin were purchased from Agilent Technologies (USA). Phosphate-buffered saline (PBS) (Sigma-Aldrich, Belgium), Tween 20 (Biochemica, UK) and superblock buffer (ThermoFisher, Belgium) were used. All buffers were prepared with deionized water. Double-sided pressure sensitive adhesive (PSA) tape (200MP-7945MP) was provided by 3M (USA). PVC transparent foils (180 μm) and COC foils (PE 135 X, Tekniplex, Belgium) were utilized. Whatman qualitative filter paper grade 40 was acquired from The Merck group—Sigma Aldrich (Belgium) Bright filed microscope images were taken with Nikon Ti Eclipse inverted fluorescent microscope (Nikon, Japan). The microfluidic designs were done in the CAD software Inkscape and they were cut using a digital table top craft cutter KLIC-N-KUT MAXX Air (KNK, USA). Videos of the microfluidic operations were taken with Logitech c920 webcam and analyzed with the software tracker (AAPT, USA). The PHD 2000 syringe pump (Harvard Apparatus, USA) was used. A 2 mm diameter permanent neodymium-iron-boron (NdFeB) magnets, purchased from Supermagnete (Belgium), with a magnet strength of 1.3 T were used.

Microwell Array Fabrication

Figure 27:
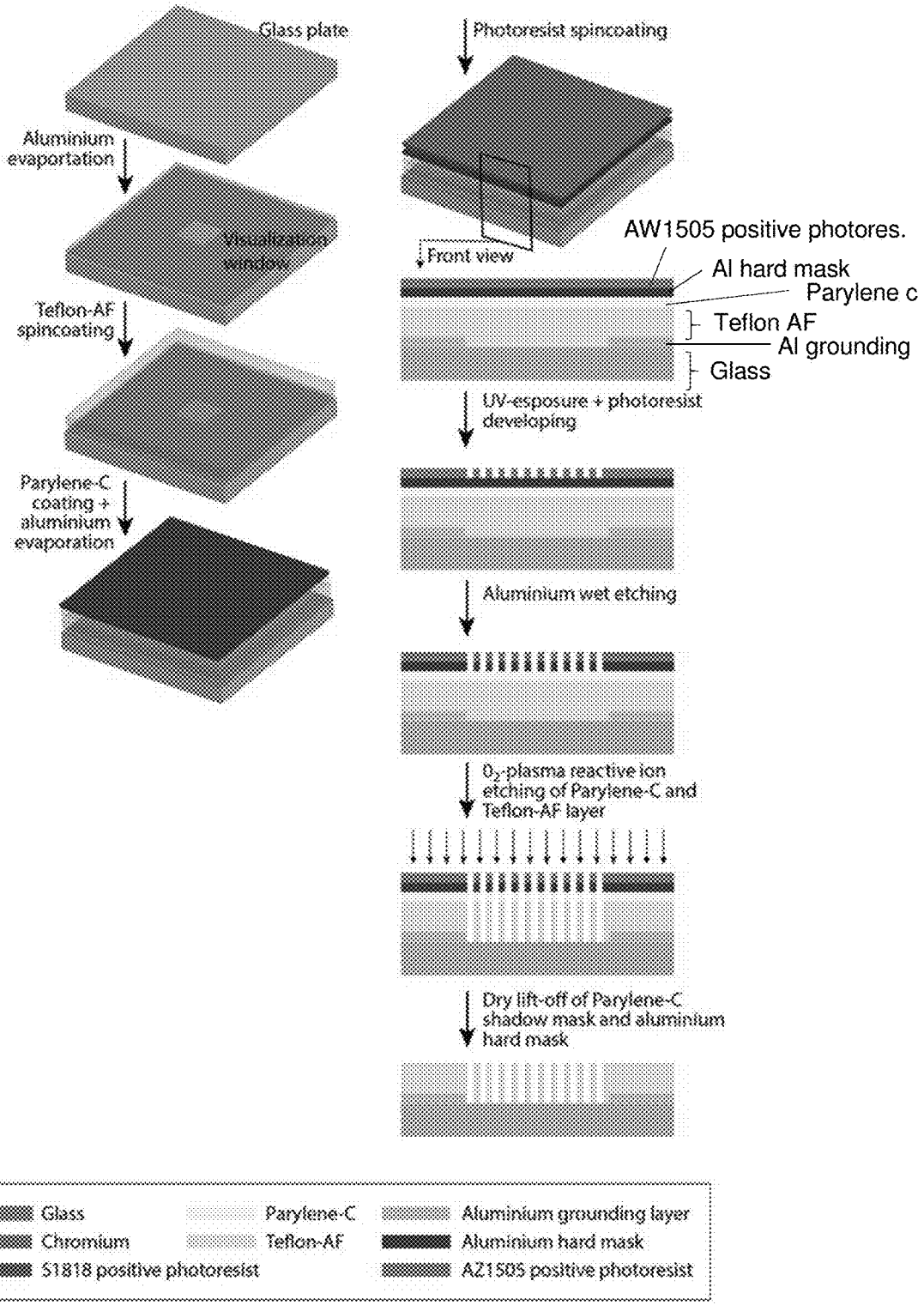
FIG. 27: Schematic work flow for the fabrication of the microwell array grounding plate, using both a Parylene-C shadow mask and an aluminum hard mask.

Prototypes with microwell arrays were fabricated in a cleanroom following the protocol briefly presented in FIG. 27. This fabrication process resulted in 62,500 femtoliter-sized microwells of 4.5 μm diameter and 3 μm depth with an 8 μm center-to-center spacing, in a square patch of 2×2 mm². The volume of each microwell is around 38 fL. The femtoliter-sized HIH microwells on a glass plate was achieved through a dry lift-off method resulting in a very hydrophobic Teflon-AF as top layer. This hydrophobic layer has ideal flow properties, keeps the water based fluorogenic substrate in the wells to create microchamber reactions.

Other materials such as PVC, PMMA, COC and OSTE which can reduce the complexity and the cost of the fabrication process can be used as well.

Microfluidic Chip Fabrication and Microfluidic Set-Up

In order to achieve continuous flow seeding of beads in the HIH wells array, the prototypes with microwells were integrated in a microfluidic chip. The microfluidic channel was designed using the CAD software Inkscape and was cut with a digital craft cutter in a PSA foil and attached to the bottom layer with the HIH wells array. The microfluidic channel was sealed with a top layer of COC which contains inlet and outlet holes.

The outlet of the microfluidic chip is connected to the suction system (i.e. syringe pump or suction pump, SIMPLE) in order to precisely control the flow rate in the channels. A 2×1 mm NdFeB cylindric permanent magnet was integrated in a 3D printed holder to ensure the proper distance between the magnet and the chip and ensure the correct alignment of the magnet with the array (FIG. 28). The technical aspect of the distance between the magnet and the array is as follows: if the magnet is too close to the array, this results in clustering of beads on the array, if it is positioned too far seeding is suboptimal. The optimal distance was calculated and experimentally determined. The sample (i.e. 10 μL) was then deposited on the inlet of the chip and pulled into the network by suction system (i.e. syringe pump or suction pump, SIMPLE).

Optimization Magnet Distance

This corresponds to three different distances of 1.75, 2.4 and 3.5 mm respectively. The seeding efficiency is calculated by analyzing bright field microscope images with a 10× objective resulting in ±27,000 microwells visualized. Two pictures were taken in every experiment, one before the seeding to count the total number of wells and check the presence of leftover beads from previous experiments, and one after to count the total number of seeded wells. Images where more than 85% seeding was achieved are considered as 'good'. An I-optimal full factorial design (Table 2) was set up with two factors and three levels, one of which being the center point on which to investigate the effect of the magnetic distance on the seeding efficiency Running the full complement of all possible factor combinations means that the main effects, interaction effects and even possible quadratic effects can be estimated.

TABLE 2

I-optimal full factorial DOE of the optimization magnet distance experiment.

| | Block | Flow rate (μL/min) | Magnet distance (mm) |
|---|---|---|---|
| 1 | 4 | 1 | 1.75 |
| 2 | 1 | 5 | 1.75 |
| 3 | 2 | 10 | 1.75 |
| 4 | 2 | 1 | 2.4 |
| 5 | 5 | 5 | 2.4 |
| 6 | 3 | 10 | 2.4 |
| 7 | 6 | 1 | 3.5 |
| 8 | 1 | 5 | 3.5 |
| 9 | 3 | 10 | 3.5 |

Optimization Beads Concentration and Flow Rate

After the optimal distance of the magnet was found, different bead concentrations and flow rates were investigated to further maximize the seeding efficiency. The concentration of the beads concentration needs to be balanced based on the magnet distance and flowrate. The number of beads must be larger than the number of wells in the array. The flow rate of the pump needs to be balanced based on the magnet distance, if the flowrate is too high beads do not have "time" to reach the array, if the rate is too slow aggregation might occur. As a follow up experiment two different concentrations of beads were tested, 2.5 and $5 \times 10^7$ beads/mL because these concentrations are commonly used in digital assay protocols. Respectively, 5 and 10 μL of the beads stock solution were diluted by adding 155 μL SBT after two washing steps. Two different flow rates were also tested, 5 and 10 μL/min, being within the range of the flow rate achievable with the suction pump platform. The microfluidic set-up used was the same as the one presented in FIG. 28 and a two level full factorial block design (Table 3) with replication was set up and was divided in two blocks taking the variance of different arrays into account.

TABLE 3

Two level full factorial block DOE of the Optimization beads concentration and flow rate experiment.

| | Block | Flow rate (µL/min) | Bead concentration (×10⁷ beads/mL) |
|---|---|---|---|
| 1 | 1 | 10 | 2.5 |
| 2 | 1 | 5 | 2.5 |
| 3 | 1 | 10 | 5 |
| 4 | 1 | 5 | 5 |
| 5 | 2 | 10 | 2.5 |
| 6 | 2 | 5 | 2.5 |
| 7 | 2 | 10 | 5 |
| 8 | 2 | 5 | 5 |

Suction Pump Platform

The suction pump platform (FIG. 29) is an innovative self-powered, robust, disposable and easy to use microfluidic pumping system. It consists of a porous material (e.g. filter paper), a working liquid chamber and an analytical channel through which a sample can flow. It uses the advantage of paper microfluidics, i.e. no energy input needed to pull liquid, combined with traditional channel based microfluidic, where the sample does not get in contact with the porous material. The working liquid is first prefilled in its chamber and the sample is placed on the sample inlet. After that, the suction pump is activated by applying pressure (i.e. finger press) on the working liquid chamber in order to bring the working liquid in contact with the porous material, which starts to absorb the working liquid due to capillary forces. This creates an under pressure in the analytical channel, pulling the sample into it. Air from the porous medium exits the chip through vent-holes. The capillary pressure exerted on the working fluid depends on the porosity and structure of the porous material (in this case Whatman grade 40 filter paper was used), as well as its degree of saturation. The flow rate and the amount of liquid pulled can be tuned by changing the shape and size of the porous material (e.g. wider angle of a circular sector shaped porous material results in faster flow rate).

In the present invention, a specific design of a suction pump was made to replace the syringe pump as pumping system and to replicate the conditions used in the optimization phase in terms of flow rate and sample volume handled. The microfluidic channel should be designed to ensure a proper flow of the beads without bubble formation and should accommodate the entire array. At the same time the width of the channel shouldn't be too large than the array width to make sure that most of the bead in solution must go over the array. The surfaces properties of the array and bottom channel should be such that they do not show affinity to the microbeads to avoid unwanted aggregation/immobilization of beads in the channel or over the array. The microfluidic design of the suction pump chip used is shown in FIG. 30. The microfluidic channel was cut in the PSA layer and was sandwiched between a bottom and a top PVC layer. The top layer was designed with outlet and the bottom layer was designed with inlet. A porous material, in this case Whatman grade 40 filter paper, shaped with the digital craft cutter, was inserted into the porous material chamber during the fabrication. Prefilling of the working liquid was done through the prefilling hole, which was then sealed.

Validation Flow Rate on Suction Pump

The flow rate of the suction pump is characterized and tuned to match the one found in the optimization phase with the syringe pump. The suction pump was fabricated as presented in FIG. 30 using as porous material a 60° circular sector of Whatman grade 40 filter paper. The suction pump was then connected with the outlet of the microfluidic chip with the microwell array. Here however, the middle layer of the microfluidic chip (PSA layer) is marked in well-known volumes to determine the flow rate (volume in function of time) (FIG. 31). The pump is activated and colored liquid is pipetted on the inlet. The experiments were recorded with a webcam and the videos were analyzed using the software tracker. The flow rate of this system was measured and resulted to be 6.59±0.78 µL/min over six repetitions. This experiment proved that this microfluidic system in which the SIMPLE ensures the pumping power, provide a constant flow rate in the optimal range and can successfully replace the syringe pump from the fluid manipulation point of view.

Seeding with Suction Pump

The optimization of the parameters on the syringe pump and the Suction Pump flow rate validation experiments are now combined into one microfluidic set-up (FIG. 32). 15 seconds after the activation of the Suction Pump (to reach the constant flow rate phase of the Suction Pumping) the beads are seeded on the HIH microwell array by pipetting a droplet of 10 µL SBT containing 5×10⁷ beads/mL onto the inlet of the channel. The optimized conditions are integrated on the Suction Pump platform as proof of the concept of seeding superparamagnetic beads in HIH microwells with a self-powered microfluidic platform for digital assay implementation towards POC test applications.

Optimizing the Magnet Distance: An Experimental Approach

To optimize the distance of the magnet from the array experimentally, three different distances of 1.75, 2.4 and 3.5 mm were tested. In each experiment 10 µL of 2.5×10⁷ beads/mL in SBT was deposited onto the inlet of the channel Each distance was tested for three different flow rates (1, 5, 10 µL/min) and the seeding efficiency for every combination is shown in Table 4.

TABLE 4

The result of I-optimal full factorial blocked design of seeding efficiencies at different distances with flow rate varied between 1, 5 and 10 µL/min.

| | Block | Flow rate (µL/min) | Magnet distance (mm) | Seeding Efficiency (%) |
|---|---|---|---|---|
| 1 | 4 | 1 | 1.75 | 70.3 |
| 2 | 1 | 5 | 1.75 | 76.3 |
| 3 | 2 | 10 | 1.75 | 76.8 |
| 4 | 2 | 1 | 2.4 | 84.6 |
| 5 | 5 | 5 | 2.4 | 82.2 |
| 6 | 3 | 10 | 2.4 | 80.4 |
| 7 | 6 | 1 | 3.5 | 34.3 |
| 8 | 1 | 5 | 3.5 | 31.2 |
| 9 | 3 | 10 | 3.5 | 27.8 |

From Table 4, it can be seen that at the largest distance (i.e. 3.5 mm) really low seeding was achieved. On the other hand, the maximum seeding should be around 82% based on Table 4 and in between the first two distances. By fitting these results the maximum can nicely be visualized (FIG. 34).

These results are supported by the microscope images for the three different distances. As shown in FIGS. 35(A) to 35(C), at a distance of 1.75 mm aggregation of bead is present while at 3.5 mm low seeding is present. When the distance is set at 2.4 mm, the seeding efficiency increase and the optimal distance is expected to be between 1.75 mm and 2.4 mm.

The data obtained is now being analyzed, this is done using the feature fit model in JMP and this will find which factors are significant or not significant. The aim is to find the optimal distance to maximize the seeding efficiency. After estimating all the main effects, interaction effects and even possible quadratic effects (Table 5), it can immediately be seen that the flow rate has no influence on the seeding efficiency and no interaction with the magnetic distance. So the flow rate can be excluded from the model since the probability is higher than 0.05%.

TABLE 5

Parameter estimates of all main, interaction and quadratic effects of the full factorial I-optimal design with standard error and probability values.

| Term | Estimate | Std Error | Prob > \|t\| |
|---|---|---|---|
| Intercept | 81.46 | 1.50 | <0.001 |
| Flow rate | 1.15 | 1.19 | 0.4069 |
| Magnet distance | 17.15 | 3.25 | <0.0132 |
| Flow rate × Magnet distance | −3.37 | 1.31 | 0.0825 |
| Flow rate × Flow rate | −0.79 | 1.67 | 0.6675 |
| Magnet distance × Magnet distance | −33.64 | 2.32 | <0.0007 |

Example 14: Optimizing Flow Rate And Bead Concentration

The optimal magnet distance was estimated at 2.2 mm and a holder was made at this distance in order to continue with experiments and reduce the variability between the experiments. Due to limits in the 3D-printer the distance of the holder turned out to be 1.95 mm. The model predicts a seeding efficiency of 80.4% which lies in between the RMSE interval of ±2.3%. In fact, no immobilization was observed in future experiments which only indicates a closer distance and thus a higher magnet force which ensure higher seeding efficiencies. Besides the magnet distance, two other important parameters were considered being the bead concentration (2.5 and 5×10$^7$ beads/mL) and the flow rate (5 and 10 μL/min). The two level full factorial block DOE results with replication are shown in Table 6.

TABLE 6

The results of the two level full factorial block DOE of seeding efficiencies with flow rates of 5 and 10 μL/min and a bead concentration of 2.5 and 5 × 10$^7$ beads/mL.

| Block | Flow rate (μL/min) | Bead concentration (10$^7$ beads/mL) | Seeding Efficiency (%) |
|---|---|---|---|
| 1 | 1 | 10 | 2.5 | 74.7 |
| 2 | 1 | 5 | 2.5 | 93.2 |
| 3 | 1 | 10 | 5 | 88.9 |
| 4 | 1 | 5 | 5 | 92.9 |
| 5 | 2 | 10 | 2.5 | 77.8 |
| 6 | 2 | 5 | 2.5 | 82.0 |
| 7 | 2 | 10 | 5 | 83.9 |
| 8 | 2 | 5 | 5 | 90.2 |

Table 6 shows immediately that the chosen factor levels are already a good estimation of good efficiencies, even 90%+ being common. By fitting the mean of the results of Table 6 the maximum set of conditions can be nicely visualized along with the standard deviation (FIG. 36).

To determine the optimal settings for these parameters in this DOE, the desirability for seeding efficiency was set to be maximized, this is done with the prediction profiler feature in JMP, resulting in the desirability plot of FIG. 37. With this, it can be observed how the prediction model changes when the settings of the individual factors are changed. A seeding efficiency of 91.6% is predicted for a distance of 1.95 mm at settings of 5 μL/min and 5×10$^7$ beads/mL.

TABLE 7

Comparison between experimental derived predictive model, the validation experiment and scaling to the maximum of the model.

| | Predictive model (%) | Validation experiment (%) | Scaling to model maximum (%) |
|---|---|---|---|
| FR 5, BC 2.5 × 10$^7$ | 87.6 | 84.6 | 85.9 |
| FR 5, BC 5 × 10$^7$ | 91.6 | 90.3 | 91.6 |
| FR 10, BC 2.5 × 10$^7$ | 76.3 | 79.3 | 80.4 |
| FR 10, BC 5 × 10$^7$ | 86.4 | 89.3 | 90.6 |

Moreover, the settings identified from the model as being optimal, turned out to effectively be the one that resulted in the highest seeding efficiency and the ratios are somewhat maintained (RMSE=4.1%).

The optimal conditions of a distance of 1.95 mm, a flow rate of 5 μL/min and a bead concentration 5×10$^7$ beads/mL were found to have a maximal seeding efficiency predicted at 91.6%.

Example 15: Validation Flow Rate

The fabrication and flow rate of the Suction Pump platform is investigated and tuned to match the requirement of a flow rate of 5 μL/min. The Suction Pump will be used to replace the syringe pump as microfluidic tool to manipulate the beads on chip.

In previous experiments, it was found that a Suction Pump with a 60° circular sector porous material (Whatman grade 40) resulted in a constant flow rate of 7.00±1.01 μL/min after 15 seconds of its activation with a standard deviation 1.02 μL/min. This value is in between 5 and 10 μL/min, flow rates found to be optimal in the previous Section. Here, the design of the Suction Pump was adapted for being able to connect the Suction Pump to the chip with the microwell array. The flow rate of this system was measured and resulted to be 6.59±0.78 μL/min over six repetitions which is sufficiently close to the one obtained in the previous SUCTION PUMP characterization experiments. This experiment proved that this microfluidic system in which the SUCTION PUMP ensures the pumping power, provide a constant flow rate in the optimal range and can successfully replace the syringe pump from the fluid manipulation point of view.

Example 16: Seeding with Suction Pump

The optimized conditions found in the previous examples were implemented in the Suction Pump powered chip. In particular, the magnet was set at a distance 1.95 mm, and the beads (5×10$^7$ beads/mL) were flown over the array with the Suction Pump characterized previously (average flow rate of 6.59 μl/min). According to the predictive model a flow rate of 6.59 μL/min with a bead concentration of 5×10$^7$ beads/ mL at optimal magnetic distance should give a seeding efficiency of 89.9% and because the RSME is 4.1% and the maximal prediction is 91.6% the design of the Suction Pump can be kept.

Combining the microfluidic set-up and replacing the syringe with the Suction Pump, FIGS. 38(A) and 38(B) show very high seeding efficiencies:

In Table 8 the seeding efficiencies of seeding with the Suction Pump are shown confirming seeding efficiencies of more than 90%:

TABLE 8

Seeding efficiencies of seeding with the Suction Pump using the optimized conditions.

| | Seeding Efficiency (%) |
|---|---|
| Array 1 | 93.5 |
| Array 2 | 97.3 |
| Array 3 | 91.7 |

Example 17: Seeding in Combination with a Propulsion Pump

Combination of a suction pump, used for the seeding and propulsion pump, used to flow the fluorogenic substrate and subsequently oil as presented in FIGS. 24(A) to 24(H) and FIG. 25 results in self-powered microfluidic chip that:
Requires no power or external equipment
Is programmable, automated, portable, disposable, low-cost and user-friendly
Does not need trained personnel to be operated
Requires a single activation steps
Achieves high seeding efficiency (>90%) in a reproducible way (3% CV)
Uses a combination of continuous flow and magnetic attraction to seed the beads
Requires only one passage of the beads solution over the array
Does not require necessarily super hydrophobic surfaces, since the continuous flow approach can pull the beads solution over simply hydrophobic surfaces (contact angle >60°)
Achieves the sealing step (fluorogenic substrate in the well and oil on top to prevent evaporation) without any extra steps by the user
Receives in input functionalized beads and give in output a chip ready to be visualized under a microscope for the final read-out.

Example 18: Ejection of a Large Volume of Liquid with iSIMPLE

Microfluidic pumps need to be versatile in handling a range of liquid volumes in order to adapt to different applications. In the previous experiments, a small volume of liquid (9 µL) was successfully pushed in a reproducible way using the iSIMPLE pump. To test the ability of the iSIMPLE to eject larger volumes, we further adjusted its design. This was achieved by simply increasing the height of the channels from 153 to 306 µm when using two layers of PSA between the top and the bottom PVC layer. In this way, we boosted the capacity of the chip to host increased volumes of both working and outlet liquid while keeping the overall size of the chip limited (100×120 mm). To avoid any gap between the top and bottom PVC layer, we used here a diamond shaped porous material slightly thicker than the height of the chamber (Whatman grade 113, Table 1), which was still possible to fit between the layers. Moreover, the diameter of the outlet hole was increased to accommodate the larger volumes for ejecting. The ejection of the outlet liquid was monitored until the pump terminated due to saturation of the porous material with the working liquid. As depicted in FIG. 41, the iSIMPLE ejected more than 150 µL in 5 min. Moreover, using this porous material and design, an average flow rate of 30 µL/min was obtained, expanding even more the range of flow rates achievable with the iSIMPLE pump. The four tested pumps demonstrated a high reproducibility (CV<3%) of the ejected volume during operation (0 min-4.5 min). The pumps stopped at slightly different times, reaching different ejected volumes, which led to an increased error from 5 min onwards, however, still with a CV<6% (data not shown).

Example 19: Ejection of Viscous Liquids Through Microneedle with a Propulsion Pump One of the current limitations of the self-powered microfluidic approaches is the difficulty to handle highly viscous liquids through small channels, mainly because of the high pressure needed. For this reason, self-powered LOC devices are mostly limited to water based fluids with low viscosity. However, for both POCT and drug delivery applications, the most relevant fluids have much higher viscosity than water ($0.93*10^{-3}$ Pa*s at 25° C.). For instance, body fluids that are often used as samples in the POCT can have viscosities ranging from $1.08*10^{-3}$ Pa*s at 20° C. and $0.84*10^{-3}$ Pa*s at 37° C. for urine until $3.79*10^{-3}$ Pa*s-$4.50*10^{-3}$ Pa*s at 25° C. and around $2.66*10^{-3}$ Pa*s at 37° C. for whole blood. For drug delivery applications, drugs and vaccines show even higher viscosity ranging between $20*10^{-3}$ Pa*s and $40*10^{-3}$ Pa*s when containing proteins or therapeutic antibodies (i.e. Infliximab, Adalimumab, IgG$_1$ monoclonal antibodies, at concentrations ranging between 100 and 200 mg/mL).

To test the capacity of the iSIMPLE for handling highly viscous fluids, we diluted glycerol in water to achieve five different concentrations, namely 0, 20, 40, 60, 80% (v/v) corresponding to $0.93*10^{-3}$ Pa*s, $1.66*10^{-3}$ Pa*s, $3.68*10^{-3}$ Pa*s, $10.53*10^{-3}$ Pa*s, $55.88*10^{-3}$ Pa*s, respectively.

The dynamic viscosity of different glycerol concentrations is well known for defined temperatures. However, since temperature has a strong effect on the dynamic viscosity, the temperature of each glycerol concentration was measured right before the experiment using a thermocouple and the HOLEX 9917 digital multimeter. In particular, experiments with 0, 20, 40, 60, 80% of glycerol were performed at 25, 25, 23, 23, and 24° C., respectively. To calculate the correct viscosity for the specific experimental temperature, we first established the correlation between the viscosities at different temperatures for each glycerol concentration. Then, in the second step we used this correlation to calculate the viscosity for each glycerol concentration at specific experimental temperature (i.e. 25° C.).

Moreover, the theoretical pressure needed to eject these solutions through the 34 G (0.16 mm) was calculated using the Hagen-Poiseuille equation.

$$\Delta P = \frac{8 \times \mu \times L_1 \times Q}{\pi \times R_1^4} + \frac{8 \times \mu \times L_2 \times Q}{\pi \times R_2^4}$$

where µ [Pa·s] is the dynamic viscosity of the fluid, Q is the average volumetric flow rate [m$^3$/s], $L_1$ and $L_2$ [m] are the length of the internal (10 mm) and external part (4 mm) of the needle, respectively and $R_1$ and $R_2$ [m] are the radii of the internal (0.09 mm) and external part (0.04 mm) of the needle, respectively. Table 9 shows the pressure needed to eject each glycerol concentration at its specific flow rate at the experimental temperature.

TABLE 9

Theoretical pressure needed to eject different glycerol concentrations at specific flow rate and temperature through a 34 G microneedle with the iSIMPLE platform.

| Temperature [° C.] | Glycerol [%] | Dynamic viscosity ($\mu$) [cP] [$10^{-3}$ Pa*s] | Vol. flow rate (Q) [$\mu$l/min] | $\Delta P$ [Pa] |
|---|---|---|---|---|
| 25 | 0 | 0.93 | 1.57 | 94.3 |
| 25 | 20 | 1.66 | 1.39 | 150.2 |
| 23 | 40 | 3.68 | 0.88 | 209.2 |
| 23 | 60 | 10.53 | 0.85 | 576.9 |
| 24 | 80 | 55.88 | 0.99 | 3588.7 |

It is important to note that liquids with higher viscosity were not investigated because $50*10^{-3}$ Pa*s was reported as the empirical viscosity threshold for injections. Moreover, to show the potential of the iSIMPLE platform for drug delivery, a microneedle (34 G (0.16 mm) diameter) was attached to the outlet hole. The selection of 34 G (0.16 mm) microneedle was based on its successful use in a preclinical test for intradermal delivery of influenza vaccine. Whatman grade 40 was chosen as a porous material in the iSIMPLE for these experiments since it showed the smallest variability when measuring the flow rate.

Using the iSIMPLE platform, 15 μL of outlet liquids with different viscosities was ejected through a microneedle. The average flow rate between section 1 and 5 (marked on the outlet channel as explained in paragraph Flow rate as a function of filter paper characteristics) was found to be 1.57±0.12, 1.39±0.12, 0.88±0.07, 0.85±0.06 and 0.99±0.11 μl/min for 0, 20, 40, 60 and 80% of glycerol, respectively (FIG. 42). As depicted in the bar chart, although the flow rate decreases in function of the glycerol concentration from 0 to 40%, no significant differences could be observed among 40, 60 and 80% glycerol concentrations. These results suggest that the iSIMPLE behaviour becomes viscosity independent above a certain level (i.e. 40%). Moreover, the flow rates for all the conditions were reproducible (CV≤10%) and constant during pump operation.

To calculate the theoretical pressure generated by the iSIMPLE for each condition, we used the Hagen-Poiseuille equation. These calculations resulted in 94.3, 150.2, 209.2, 576.9 and 3588.7 Pa for 0, 20, 40, 60 and 80% (v/v) of glycerol in water, respectively, proving once more that the iSIMPLE can generate high pressures as a self-powered microfluidic pumping system. Moreover, it is important to note that, compared to the previous experiment where 64.0 kPa was achieved with the CV of 20%, the reproducibility of the iSIMPLE operation significantly improved in this experiment when lower pressure was generated (CV of ≤10% for maximal 3.6 kPa reached in this experiment).

Example 20: Injection of Solutions into Skin-Mimicking Matrix with iSIMPLE

Foley et al. reported that a pressure of 3.5 kPa was sufficient to inject a dye into a mice brain while in the work of Gupta et al., a pressure around 13 kPa was needed to inject a large volume (100 μL) into a human forearm at high flow rate (300 μL/min). Even though this pressure was successfully reached by the iSIMPLE (see previous two paragraphs), in order to fully demonstrate its potential for drug delivery applications, we tested here the injection of a different glycerol concentrations in a skin-mimicking matrix.

Agarose was chosen as skin model system since it is widely reported in literature as one of the best synthetic models for human skin. Moreover, its partial transparency allows a visual inspection of the liquid injection. Two different agarose concentrations (1 and 2.65% (w/v)) were used to mimic the mechanical properties of the human skin. In order to mimic the mechanical properties of the human skin, agarose substrate was prepared starting from the agarose powder (Melford, UK) that was added to distilled water to reach the proper concentration (i.e. 1% w/v, 2.65% w/v). The solution was heated on a hot plate with magnetic stirring until the agarose powder was completely dissolved. The solution was then poured into a petri dish and cooled down at RT. Several agarose parallelepipeds (15×15×10 mm) were cut and used as skin mimicking matrix for the experiment.

Based on the results from the previous paragraph, only two glycerol concentrations (i.e. 0 and 40%) were selected here for testing since there was no significant difference in the flow rate between 0 and 20% or among 40, 60 and 80%. Following the standard procedures of performing intradermal injections at the depth of 1-5 mm, the microneedle was inserted for approximately 2 mm in an agarose matrix. The same iSIMPLE design was used in these experiments as described in the previous paragraph.

An overview of the different tested conditions is presented in FIG. 43. For each condition, the outlet liquid was initially delivered from the needle tip and diffused around the needle walls (sections $S_1$). Irrespectively of the glycerol or agarose concentration, the outlet liquid was progressively delivered into the matrix (sections S3) to finally reach a Gaussian-shaped diffusion around the needle towards the surface of the agarose matrix (sections S5). Nevertheless, all the outlet liquid remained into the matrix and back-flow of liquid out of the agarose block was not observed. These results demonstrated that iSIMPLE has a huge potential to be used as a self-powered finger actuated patch system for delivering liquids of different viscosities in a controlled way over time. In fact, taking into account the results presented in the previous paragraphs, the flexibility of designing iSIMPLE with different properties (flow rate and pumping volume) can meet various specific requirements for the delivery of drugs or vaccines.

Example 21: Drug Delivery in Ex Vivo Skin Model System with iSIMPLE

Finally, the potential of the iSIMPLE for drug delivery was tested in ex vivo experiments. To do this, we selected chicken breast as biological matrix mimicking human skin, since it was previously described in similar drug delivery work. Blue colored water (i.e. 0% glycerol concentration) was used as outlet liquid to facilitate the visualization into the chicken flesh. The iSIMPLE design and set up were comparable to the one presented in the previous paragraph, with the needle tip inserted into the chicken breast at approximately 2 mm depth.

Using the iSIMPLE coupled to a 34 G (0.16 mm) microneedle, after a simple finger activation, we were able to inject 15 μL of solution into the chicken breast flesh in less than 20 min on average ($S_1$, $S_2$, $S_3$ in FIG. 44). As can be seen from the cross section of the ex vivo matrix (FIG. 44, Slice), the liquid was dispensed horizontally at the depth of the needle tip. Because the needle was inserted perpendicularly to the muscle fibers direction, this suggests that the liquid diffused between the fibers. It is important to notice that no back flow was observed since all the solution was delivered at the injection depth and none escaped along the needle shaft back to the flesh surface. This final experiment clearly proved that the iSIMPLE, coupled to a microneedle, has all the requirements to be used as innovative completely autonomous intradermal drug delivery system.

Example 22: Hydrophobic Valve Fabrication and Characterisation

Whatman quantitative filter papers grade 40 and 43 and Whatman 1PS phase separator filter paper were acquired from The Merck group—Sigma Aldrich (Belgium). Double-sided pressure sensitive adhesive (PSA) tape (200MP 7956MP) from 3M (USA) and PVC transparent foils 0.18 mm thick (Delbo, Belgium) were utilized. Aquapel solution was bought from Aquapel (USA). A digital webcam (C920, Logitech, Switzerland) was used to video record the experiments. The images extracted from the videos were modified with Adobe Lightroom to enhance contrast and saturation. For the pressure burst characterization of the hydrophobic barrier, the recorded videos were used to monitor the displacement of the measuring plug based on the markings cut on the side of the channels.

In order to make the filter paper hydrophobic but at the same time gas permeable, we used Whatman grade 43 and applied a fluorinated compound, being Aquapel. Before the Aquapel treatment, the filter paper was cut with a digital tabletop craft cutter (Cameo, Silhouette, USA) either in a rectangular shape (3×1.5 mm) to be used as a hydrophobic barrier, or droplet shape (with the same surface area) to be used as hydrophobic vent (e.g. in a hydrophobic valve). Differences between these two structures and their applications are explained more in details in the results paragraphs 3.2 and 3.3, respectively. Three different volumes of Aquapel (4) were tested per surface unit (mm2) for the hydrophobic barrier (i.e. 0.0364, being the minimum amount of Aquapel that could be pipetted on the hydrophobic barrier; 0.182 and 0.364, the latter already oversaturating the surface). For the hydrophobic vent, only one volume of Aquapel was used (0.182 µL/mm2). Afterwards, the samples were dried at 50° C. for 24 hours.

For assessing the hydrophobicity of the treated filter paper in function of the amount of Aquapel, larger patches of 25×10 mm were made while keeping the same volume of Aquapel per surface unit. These patches were subjected to water contact angle measurements using a digital goniometer (CAM 200, KSV, Finland). The contact angle was measured for four droplets per patch, each droplet being approximately 9 µL of distilled water.

For measuring the burst pressure, a microfluidic chip was designed similarly to previous works.28 Briefly, a measuring channel was connected on one side to a syringe pump (PHD 2000, Harvard Apparatus, US) and on the other side to an open outlet. A measuring plug (blue liquid, 0.4 µL) and sample (red liquid, 0.7 µL) were prefilled in the channel separated by a known volume of air (FIG. 45(A)). The sample was prefilled until it reached the hydrophobic barrier, which was inserted during the fabrication in the microfluidic network to serve as a physical barrier for the sample and positioned before the outlet. When the measuring plug was pushed at a constant flow rate (i.e. 2 µL/min) using the syringe pump, its displacement was monitored by means of the markings on the side of the measuring channel (offset 0.5 mm) (FIG. 45(B)). Initially, the sample did not show any movement because it was blocked by the hydrophobic barrier. Only when the pressure between the measuring plug and the sample reached the burst pressure, the sample overcame the barrier and flew towards the outlet (FIG. 45(C)).

Example 23: Microfluidic Chips Fabrication

The SIMPLE and iSIMPLE microfluidic devices were fabricated according to the low-cost and rapid prototyping method presented in Yuen et al. Lab Chip 2010 and Dal Dosso et al. Anal. Chim. Acta 2017. In short, the microfluidic channels were cut in the PSA layer by using a digital tabletop craft cutter (Maxx Air 24", KNK, USA). Microfluidic channel height was determined by the PSA thickness, in this case being 0.153 mm. The PSA layer was sandwiched between a bottom and top PVC layer, with the latter one featuring the necessary inlet, outlet, prefilling and vent-holes. Porous materials (i.e. filter papers) were cut with a digital craft cutter (Cameo, Silhouette, USA) and inserted into their respective chambers during the assembly. The number of porous materials and their type was determined by the application. In particular, Whatman grade 40 was used as porous material for the SIMPLE/iSIMPLE pumps while Whatman grade 43 was used for the hydrophobic vent (e.g. for the hydrophobic material in a hydrophobic valve including a vent) and hydrophobic barrier. Each microfluidic chip was then prefilled with different liquids based on the specific design. Colored water was used for a better visualization of the microfluidic manipulation, in particular, blue, red, orange and green food colors diluted in distilled water (1:20) as working liquid (WL), sample (S), trigger liquid (TL) and stop liquid (SL), respectively. As reported in Dal Dosso, et al. Anal. Chim. Acta 2017 liquids were pipetted into the respective chambers through the prefilling holes, which were then sealed with a PSA patch.

Example 24: Investigating Hydrophobicity of Developed Microfluidic Valve

Commercially available filter paper (i.e. Whatman 43) was treated with a fluorinated compound (i.e. Aquapel) to make its fibers hydrophobic. The substrate maintained its porous structure to allow gas flow, but became impermeable to liquid. The obtained combination of gas permeability and liquid impermeability makes this approach distinct from other methods, like wax patterning commonly used in paper based microfluidic, since the latter would make the filter paper hydrophobic but not gas permeable due to complete sealing of the paper pores by the wax (Gerbers, et al. Lab Chip 2014; Cate, et al. Anal. Chem. 2015; Hitzbleck and Delamarche. Chem. Soc. Rev. 2013).

To determine the hydrophobicity degree of the developed hydrophobic valve, we measured a contact angle of a water droplet in function of different Aquapel amounts (0.0364, 0.182, 0.364 µL) applied per mm2 of a surface (will be referred to as treatment 1, 2 and 3, respectively). As shown in FIG. 47, the obtained water contact angles were 144.6±3.1°, 155.3±1.3°, 155.0±4.2°, respectively. As a reference, we used Whatman 1PS filter paper, which is a commercially available hydrophobic paper that owes its hydrophobicity to silicon-based treatment and is used for phase separation. Under the same experimental conditions, this paper revealed a value of 138.3±4.1° for a water contact angle. These results proved not only that the developed valves are hydrophobic in nature, but that they have also reached the threshold (set at 150°) to be considered super-hydrophobic (Song and Rojas. Nord. Pulp Pap. Res. Journa 2013). Moreover, the obtained values were in line with those previously reported in literature where different treatments, such as plasma enhanced etching (Balu, et al. Contact Angle, Wettability, Adhes. 2009) and surface coating or dipping (Hu, et al. Eng. Asp. 2009; Baidya, et al. ACS Nano 2017; Bashar, et al. RSC Adv. 2017) were applied to obtain (super)hydrophobic paper substrates (Samyn. J. Mater. Sci. 2013). However, these methods relied on either complicated and multistep fabrication methods or expensive instrumentation and as such are not widely accepted. Contrary, our one step method does not require any special equipment or trained operator, and consists of simply applying sufficient amount of Aquapel on the paper substrate and waiting until it dries. Importantly, our hydrophobic valves maintained the same hydrophobicity over time, with a shelf-life at room temperature of at least six months after the fabrication (data not shown).

Example 25: Burst Pressure Characterization

A second crucial parameter for a microfluidic valve (e.g. for a hydrophobic material or patch thereof), in particular if used as a hydrophobic barrier (i.e. a physical barrier for a liquid in microfluidic channel), is the maximum pressure bearable before breaking. As reported in literature, passive hydrophobic valve can resist pressures ranging from 0.5 to 4 kPa. (Feng, et al. Sensors Actuators A Phys. 2003; Riegger, et al. J. Micromechanics Microengineering 2010; Andersson, et al. Sensors Actuators B Chem. 2001). These valves rely on hydrophobic zone created on the channel walls of the microfluidic network to delay or stop the liquid flow. In this work, a hydrophobic barrier was inserted into the microfluidic channel matching both its width (1.5 mm) and height (0.153 mm). The burst pressure was measured using the microfluidic chip as shown in FIGS. 45(A) to 45(C). Similarly to previous work (Srivastava and Burns. Lab Chip 2007) and following the Boyle's law, the pressure increase in the measuring channel was calculated based on the displacement of the measuring plug. This was done for hydrophobic barrier made with different amounts of Aquapel and the results were compared with the hydrophobic barrier made of Whatman 1PS as a reference material (FIG. 47).

Based on these results, we concluded that: i) no significant difference was observed in burst pressure when using different amounts of Aquapel (7.38±0.82, 8.97±1.39, 8.38±1.24 kPa for treatment 1, 2, and 3, respectively), and ii) the developed hydrophobic paper could withstand higher pressure than commercial Whatman 1PS paper (4.53±0.65 kPa) or other reported hydrophobic burst valve.20, 22, 23 Taking into account these results together with the hydrophobic characterization, all hydrophobic valves were made for the remaining experiments using mid-range of tested Aquapel volumes (i.e. treatment 2). This amount was selected to avoid using excess of Aquapel (as for treatment 3) or to avoid non-uniform coverage of the patch if using too little of it (i.e. treatment 1).

In the followings paragraphs, the potential of the hydrophobic valves for channel-based microfluidic systems was exploited by integrating them with the SIMPLE and iSIMPLE platform. Three different cases were investigated where hydrophobic valves were used for: i) improving the iSIMPLE activation system, ii) allowing the splitting of a sample in two independent channels operated by two SIMPLE pumps, and finally iii) enabling the shuttling of a liquid by joining the SIMPLE and iSIMPLE pumping concepts in a single platform.

Example 26: Hydrophobic Valve Improves the Robustness of iSIMPLE Activation

Previously described iSIMPLE chip27 was activated by a single finger press on the activation zone (i.e. enlargement of the WL channel connected to the inlet hole, FIG. 48(A), which drives a WL in contact with a porous material (in this case Whatman 40). As a consequence, the absorption of the WL pushes the air present in the pores of the porous material into the outlet channel where the prefilled outlet liquid is eventually pushed forward by the pressurized air. However, when using this original design, the chip activation was often failing as it was subjected to a proper user activation. In other words, when we tested three different activation movements (each at least three times), the activation was successful at the first attempt only in 40% of the cases. In particular, a short (<1 s) or long (>3 s) pressure in the center of the activation zone, needed two or more activation attempts before effectively activating the chip. Only a rolling movement led to a successful activation but cannot be considered user-friendly and robust since consists of four steps: i) closing the inlet hole, ii) pushing the WL, iii) opening the inlet hole, and finally iv) removing the pressure from the WL.

To improve this activation step, we developed here a different activation system based on a hydrophobic valve used as hydrophobic vent (FIG. 48B-i) and implemented it on the otherwise same iSIMPLE chip design. The hydrophobic vent (magnification of FIG. 48B-i) was connected with the microfluidic channel on one side (containing working (blue) liquid), and opened to the atmosphere on the other. When the WL was prefilled, an enclosed air pouch was created at the beginning of the channel, representing an activation zone in this new design. Before activation, the hydrophobic vent was in the close configuration (its channel interface is blocked by the WL), thus the upstream air pouch was connected to the downstream part of the chip. When pressing on the air pouch, the WL came in contact with the PM and iSIMPLE was activated. Importantly, to achieve successful activation and operation, the volume values between different chip elements must fulfill the following rule: V1>V2>V3, respectively representing the air volume of the activation zone, the volume of WL before the hydrophobic vent, and the volume of air between the WL and the porous material (magnification of FIG. 48B-i). This is because V1>V2 results in the back front of the WL surpassing the hydrophobic vent interface (hydrophobic vent in open configuration, e.g. a valve with its vent open) and becoming the air source for the pump operation. If V1<V3, the WL is not pushed far enough to reach the porous material, whereas if V2<V3, the WL surpasses the hydrophobic vent before it gets in contact with the porous material.

When using this new design of the iSIMPLE chip, all the activations (10 independent repetitions) were successful irrespectively of the force, duration or position of the finger press. The only requirement was to apply sufficient pressure to bring the WL in contact with the porous material (i.e. to bridge a 1.5 mm gap). This dramatic improvement in the efficiency of iSIMPLE activation was because the hydrophobic vent divided the microfluidic network into two parts after the WL moved beyond the hydrophobic vent. In that condition, the air pouch, upstream the hydrophobic vent, was not connected any more with the downstream circuit, meaning that different activations movement or even multiple pressure did not affect the pump operation.

Example 27: Hydrophobic Valves Allow Combining Two SIMPLE Pumps to Enable Sample Splitting Important for Multiplexing Analysis A SIMPLE-based chip was developed to split a sample in two independent channels with a single user activation. The chip featured two SIMPLE pumps in addition to one hydrophobic vent and three hydrophobic barrier, as depicted in FIGS. 49(A) to 49(E). SIMPLE 1 was made of an analytical channel 1 (AC 1), a prefilled working liquid 1 (WL 1), a hydrophobic barrier 1 inserted between the AC 1 and the WL 1 chamber, and a porous material 1 (PM 1). SIMPLE 2 consisted of an analytical channel 2 (AC 2), a prefilled working liquid 2 (WL 2) and a porous material 2 (PM 2) (FIG. 49(A)). AC 1 and AC 2 merged at the inlet of the chip where a droplet of sample (S) was deposited before activation. To be able to split the sample into the two AC with a single user activation, SIMPLE 1 and SIMPLE 2 should be activated one after the other. For this purpose, a trigger system that enables the activation of SIMPLE 2 by SIMPLE 1 was developed and was made of: i) a trigger liquid (TL) prefilled between the PM 1 chamber and WL 2 chamber, ii) a hydrophobic vent positioned on a side of the TL chamber and blocked by the TL, iii) a porous barrier (PB) made of untreated Whatman 43 filter paper and hydrophobic barrier 2 inserted between the TL front and the WL 2 chamber, iv) a hydrophobic barrier 3 positioned between the AC 2 and the WL 2 chamber (FIG. 49(A)).

Figure 49C:
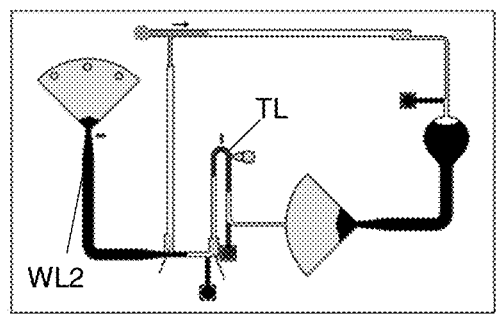

After activating SIMPLE 1 (FIG. 49(B)), an under pressure was created in the AC 1, which pulled the sample into the channel (FIG. 49(C)). At this point, the air expelled from PM 1 pushed the TL forward since SIMPLE 1 was not connected to any outlet hole. On its turn, the air pushed by the TL activated SIMPLE 2 by bringing in contact the WL 2 and the PM 2 (FIG. 49(D)). Here the role of the hydrophobic barrier 3 can be appreciated since it ensured that the WL 2 was pushed towards the PM 2 instead of into the AC 2 (FIG. 49(D)). FIG. 49(E) depicts both SIMPLE pumps pulling the sample into the respective analytical channels. In particular, the combination of a PB and hydrophobic barrier 2 ensured that SIMPLE 2 pulled only the sample and not the TL since the latter was absorbed and blocked by the PB and the hydrophobic barrier 2, respectively. Also, the essential role of the hydrophobic vent can be appreciated here: the hydrophobic vent served as vent for the air expelled during the SIMPLE 1 operation after the TL back front surpassed its interface (FIG. 49(E)). Finally, the two SIMPLE pumps stopped (FIG. 49(F)). In particular, SIMPLE 1 was terminated when the sample reached the hydrophobic barrier 1. In fact, at this point, the SIMPLE 1 was not connected to an air intake anymore and an excessive under pressure was created in the WL 1 chamber. This pulled back the WL 1 that lost contact with the PM 1. On the other hand, the SIMPLE 2 was terminated when all WL 2 was absorbed into the PM 2.

Importantly, this concept is versatile and can be adapted to specific application requirements. In fact, every channel is governed by a SIMPLE that could be designed to pump different volumes of sample at different flow rates by changing type, shape or dimension of the porous materials, as previously shown.26 The design can be expanded with more than two pumps in order to split the sample in three or more independent channels, increasing even more the multiplexing capability of this platform. The only requirement to respect in the presented design is the relationship between the volumes (V2>V1>V3>V4) indicated in FIG. 49(A). The rationale behind the importance of respecting these design guidelines is presented in Supplementary Information (section S2).

It is also interesting to notice how the delay between the activation of the SIMPLE 1 and SIMPLE 2 circuits, for fixed pumps characteristics, depends on the volume between the TL front and the hydrophobic vent. If the former covers the latter interface, as in the case of FIGS. 49(A) to 49(E), the activation of the SIMPLE 1 and SIMPLE 2 is almost simultaneous (delay of around 40 seconds). On the other hand, if the TL front is before the hydrophobic vent interface, the volume between the two defines the delay between the activations of the two SIMPLE pumps, which can be stretched for several minutes. In fact, in this case, the SIMPLE 1 will act on the SIMPLE 2 circuit only when the hydrophobic vent is blocked, since otherwise the air pushed by the TL due to the SIMPLE 1 action, could escape from the hydrophobic vent without affecting the downstream network.

Another important role of the hydrophobic barrier 1, hydrophobic barrier 2, and hydrophobic barrier 3 was ensuring a successful prefilling of the two working liquids. In fact, during the prefilling step, the hydrophobic barrier 1 ensured that the WL 1 flew in its chamber and not towards the AC 1. Similarly, the hydrophobic barrier 2 and hydrophobic barrier 3 were necessary to prevent the flowing of the WL 2 into the TL chamber and AC 2, respectively.

The chip presented here has the potential to be used for sample (i.e. blood, urine, saliva) splitting in two (or more) parallel channels, enabling the possibility to perform multiplexing analysis in a self-powered POC device. This would overcome one of the biggest drawbacks of the current self-powered POC devices that are limited in the liquid manipulation capability making the implementation of complex bioassay protocols difficult.

Example 28: SIMPLE and iSIMPLE Combined with Hydrophobic Valves for Shuttling of Liquid on Chip In the context of self-powered, easy to fabricate and inexpensive microfluidic chip, not many complex liquid manipulations have been demonstrated, limiting bioassay implementation for POC applications. In particular, self-powered platform cannot usually work in infusion and withdraw mode at the same time, for instance to shuttle a liquid back and forth in a microfluidic channel. The SIMPLE and iSIMPLE concept can respectively pull and push a liquid but they have never been combined to act on the same liquid.

Here, we combined for the first time the SIMPLE and iSIMPLE concept to manipulate a liquid back and forth in a channel thanks to the integration of the developed hydrophobic valve. The chip shown in FIGS. 50(A) to 50(G) is made of one SIMPLE that initially pulls the S into the AC, an iSIMPLE which eventually pushes the sample back and one hydrophobic vent, one hydrophobic barrier and one PB that allow the proper timing of the operations. SIMPLE was made of an AC, a prefilled WL 1, a porous barrier (PB) and hydrophobic barrier (HB) inserted between the AC and the WL 1 chamber, and a PM 1. iSIMPLE consisted of a prefilled WL 2 and a PM 2. In order to shuttle the S in the AC and operate the chip with a single user activation step, the iSIMPLE should be automatically activated after the SIMPLE pulled the S in the AC. For this reason, a trigger system, similar to the one presented in paragraph 3.4, that enables the activation of iSIMPLE by SIMPLE was developed and was made of: i) a TL prefilled between the PM 1 chamber and WL 2 chamber and ii) a hydrophobic vent in open configuration positioned on a side of the TL chamber after the TL front and before the WL 2. Because the SIMPLE should stop after the iSIMPLE is activated, a stopping system was also integrated on this chip and consisted of: i) a stop liquid (SL) prefilled after the PM 2 and before the insertion of the iSIMPLE circuit into the AC and ii) a PB and hydrophobic barrier inserted one after the other in the AC between the iSIMPLE insertion and the WL 1 chamber (FIG. 50(A)).

When SIMPLE was activated with a finger press on the WL chamber, the under pressure created into the AC pulled the S (red liquid) into it (FIG. 50(B)). At the same time the air expelled from the PM 1 pushed the TL forward. Thanks to the hydrophobic vent in the open configuration, the air pushed by the TL did not act on the iSIMPLE circuit downstream since it escaped through the hydrophobic vent. Only when the TL reached and blocked the hydrophobic vent, the air pushed by the TL could not exit through the hydrophobic vent anymore and instead pushed the WL 2 in contact with the PM 2 activating the iSIMPLE circuit (FIG. 50(C)). After the iSIMPLE activation, the air expelled from the PM 2 pushed the SL (green liquid) into the AC, and due to the combined effect of iSIMPLE and SIMPLE, it was absorbed by the PB (FIG. 50(D)). Thanks to the combination of the PB and the hydrophobic barrier, a barrier for both liquid and gases was created, which terminated the SIMPLE circuit due to the lack of an air intake (FIG. 50(D)). As a result, the S was not anymore pulled by SIMPLE. At the same time, the TL surpassed the hydrophobic vent which became the air intake port for iSIMPLE (FIG. 50(D)). At this point, iSIMPLE acted only on the AC (thanks to the PB and hydrophobic barrier) and pushed the S back along the AC (FIG. 50(E)). After the S was pushed back to the inlet, iSIMPLE terminated due to complete absorption of WL 2 into PM 2 (FIG. 50(F)).

It is important to notice that the two pumps are independent from each other, which allows for a tailored design for each of them. For instance, in this case, the PM 1 of SIMPLE was designed as a 90° circular sector, which resulted in a faster flow rate then the 10° diamond shaped PM 2 of iSIMPLE. The volume handled by the two pumps can also be different, expanding even more the flexibility of this platform. Moreover, the delay between the activation of SIMPLE and the activation of iSIMPLE circuit can be tuned by varying the initial volume (V3) between the TL front and the hydrophobic vent.

Another important role of the hydrophobic barrier was ensuring a successful prefilling of the WL 1 in its chamber rather than flowing towards the AC. Moreover, the only requirement to respect in the presented design is the relationships between the volumes (V1>(V3+V2)>V3>V4 and V2>V4) indicated in FIG. 50(A).

Example 29: Safe Disposal, Needle Disable Feature

A fold-line in the disposable patch to enable the user to fold or bend the patch over the needle or microneedle array thereby sequestering the sharp end(s) of the needle or microneedle array within the patch device (FIG. 51). The fold line provides that the (micro)needles are embedded in a needle absorbing layer upon folding of the patch device along the fold line. The needle absorbing layer accommodates or otherwise sequesters the microneedles and secures them in place. The needle absorbing layer is designed such that the height of the needle absorbing layer relative to the surface of the device matches or slightly exceeds the height of the corresponding needle or microneedle array that is to be sequestered. The needle absorbing layer may be composed of any of the suitable polymer materials that are soft enough to be pierced by the sharp ends of needle or microneedle array. The needle absorbing layer may additionally be coated with an adhesive layer, such that contact to the needle or microneedle array results in the a physical bond between the needle absorbing layer and the needle or microneedle array.

Example 30: Multi-Chamber Design/One-Step Reconstitution on the Device

In another embodiment, the (iSIMPLE) propulsion pump allows for the implementation of one-step, on-device reconstitution of active pharmaceutical ingredients, whereby at least one of the components of the active pharmaceutical ingredient or vaccine is a liquid component and at least one other ingredient is a solid component such as a lyophilized vaccine or drug (FIG. 52). Due to the ability of the (iSIMPLE) propulsion pump to generate high pressures in microfluidic channels and chambers, the design of a multi-chamber device is enabled. In this design, at least one chamber contains a liquid component, this said chamber is connected by an adjacent channel to at least one other chamber that contains a liquid or solid component that together with the first said liquid component constitute an active pharmaceutical ingredient or vaccine. Upon activation of the (iSIMPLE) propulsion pump, the first liquid component is propelled under pressure through a connecting channel to a second liquid or solid component. Upon contacting the second solid component, the first and the second components mix, or otherwise the second solid component is dissolved in the first liquid component and the resulting reconstituted mixture is further propelled along a channel connected to a needle or microneedle array. In order to ensure adequate mixing of the reconstituted components, a "mixing zone" may be included in the channel connecting the second component and the mixing zone.

Example 31: Monitoring of Pump Function/Termination of Injection Feature Barcoding/Compliance/Traceability System A passive indicator to inform the user on the successful completion of operation of the pumping mechanism of the disposable patch device. In one embodiment this is achieved by adding a visible color dye to the working liquid, and providing a transparent layer in part of the device, such that the transparent layer is positioned on top of a channel that houses the working liquid, and makes visible the passage of the working liquid in the said channel (FIG. 53). The user is informed of the termination of the working of pumping mechanism, and thereby the successful completion of the working operation of the device when the working liquid completely passes the channel visible through the transparent layer. In another embodiment, the porous material that comprises either the (iSIMPLE) propulsion pump or the (SIMPLE) capillary pump can be printed with a suitable reactive substance that in an anhydrous form is white or colorless, but that produces a color reaction upon contact with the aqueous working liquid. For example such reactive substance can be anhydrous copper sulfate. Upon saturation of the porous material, the reactive substance turns a visible color. The printed reactive substance can be applied in a pattern that would be unique to each disposable chip. Such pattern can be in the form of a barcode, a dot code or any other form of 2 dimensional matrix symbol codes. Upon hydration of the porous material and the printed reactive substance, the reactive substance can develop into a unique readable code as a priori assigned during the printing process of the reactive substance on the porous material. A transparent layer can then be positioned on top of the porous material containing the printed code to be made visible to the user or be read-off by image acquisition and processing systems (FIG. 53). The image acquisition and processing system that reads-off the unique code, such as a smart phone, can then send the result of the read-off to a central information storage and processing system, such as a cloud based ICT system. The result of the read-off can be accessed through the central information storage system by for example medical professionals to confirm that the device has been used as intended. Such a system can, for example, be used to monitor patient compliance to prescribed medications.

Example 32: A Pump Activation and (Micro)Needle Application "Button"

In one embodiment, the (iSIMPLE) microneedle drug or vaccine delivery device is designed such that the physical force, such as a finger push, that is applied used to activate the propulsion pump is also useful to provide the mechanical force to push or insert the needle or microneedle array into the skin. This can be achieved by positioning the activation button for initiation of the population pump on top on of the needle or microneedle array (FIG. 54). Such button could be configured to be "activatable" only through sufficient force, to prevent premature activation and to allow positioning of the device on skin prior to activation. As an example of a such configuration, the activation button could be a domed diaphragm that is depressible only when a certain sufficient force is applied, by for example, finger pressure.

It is noted that Examples 29 to 32 may include a hydrophobic valve according to embodiments of the present invention, for example as shown in Example 12 (with reference to FIGS. 17(A) to 17(D)).

The invention claimed is:

1. A fluid conduit device comprising
a capillary pump, comprising a solid sorbent enclosed in an enclosure and having an inlet and an outlet;
a fluid conduit operationally connected to the inlet of the capillary pump;
a gas-permeable liquid-sealed unit with a vent hole wherein said unit is gas-permeable to the outside through the vent hole, the unit being engaged with the fluid conduit at a predetermined location; and
an actuator unit upstream of the fluid conduit;
wherein the fluid conduit comprises at least three interconnected zones, the at least three interconnected zones comprising:
i) a first conduit zone prefilled with a first volume of trigger liquid, upstream of the unit with the vent hole and downstream of the gas-permeable liquid-sealed unit with the vent hole,
ii) a third conduit zone with a further volume, upstream of the capillary pump and downstream of the gas-permeable liquid-sealed unit with the vent hole, and
iii) a second conduit zone pre-filled with a working liquid before actuation of the actuator unit, the second conduit zone positioned downstream of the gas-permeable liquid-sealed unit with the vent hole and between the first conduit zone and the third conduit zone and functionally connected to both, and directly connected to the first conduit zone,
wherein the first volume is proportionally larger than or equal to the further volume of the third conduit zone.

2. The device according to claim 1, further comprising a barrier wherein the barrier comprises a gas-permeable liquid-sealed patch to allow passage of gas and stop liquid and wherein the barrier is provided in the fluid conduit between two interconnected zones.

3. The device according to claim 1, wherein the gas-permeable liquid-sealed unit with a vent hole comprises a hydrophobic material containing cavities for gas passage, for instance a hydrophobic paper.

4. The device according to claim 1, wherein the solid sorbent of the pump has cavities with pore diameter of a value between 0.1 to 35 µm.

5. The device according to claim 1, further comprising downstream of said capillary pump and connected thereto a fluid conduit output comprising microneedles.

6. The device according to claim 1, wherein the solid sorbent of the pump is shaped in a 10° to 150°, for example 50° to 70° circular sector so that the pump is adapted to pump at pressures of 50 to 100 kPa, 0.1 µl to 1000 µl volume liquid through the resistance of a biological tissue barrier, for instance a skin.

7. The device according to claim 1, the fluid conduit device comprising a network configuration of channels and/or fluid reservoirs and wherein pumps, fluid reservoirs, the gas-permeable liquid-sealed unit with vent, and optionally at least one gas-permeable liquid-sealed barrier unit are engaged in the conduit device to mix different fluids, to sequentially deliver different fluids or to push forward and back in a same conduit zone.

8. The device according to claim 1, wherein the device is a microfluidic device and the capillary pump comprises a solid sorbent containing cavities and being enclosed in an enclosure, the microfluidic device further comprising a sample delivery section for applying a liquid containing magnetic beads operationally connected to a detection zone with one or more recessed parts and a magnet positioned in the proximity of the detection zone and wherein the solid sorbent is shaped in a 10° to 150° circular sector to provide a flow rate of about 4 to 10 µl/min so that when operational the beads are immobilized in the recessed part of the detection zone in one continuous flow.

9. The device according to claim 8, wherein the magnet has a strength of about 1.3 T and is positioned about 1.5 to 2.5 mm below the recessed part, wherein the bead concentration in the liquid is about $2*10^7$ to $10*10^7$ beads/ml.

10. The device according to claim 1, further comprising downstream of said capillary pump a chamber adapted for receiving powder reagents or with a powder reagents and wherein the device is adapted to mix powder reagents with pumped liquid by the solid sorbent of the pump.

11. The device according to claim 8, wherein the capillary pump is a propulsion pump comprising a solid sorbent enclosed in an enclosure, said solid sorbent containing cavities comprising a first fluid,
wherein said enclosure of the solid sorbent comprises a first opening through which said solid sorbent can be contacted with a liquid and a second opening connecting the enclosure to an outlet channel; and
wherein said propulsion pump is adapted for being activated by contacting said solid sorbent with a liquid via said first opening resulting in the absorption of at least part of said liquid by the solid sorbent;

wherein this absorption is associated with the expulsion of at least part of said first fluid from the cavities of said solid sorbent into said outlet channel, wherein the flow of said first fluid into the outlet channel allows for propulsing and/or compressing a second fluid contained in said outlet channel and/or in a channel or reservoir connected to said outlet channel.

12. The device according to claim 11, wherein the pump is adapted to pump second fluid at pressures of 50 to 100 kPa by the solid sorbent of the pump having cavities with pore diameter of a value between 0.1 to 35 µm.

13. The device according to claim 12, wherein the solid sorbent of the pump is adapted to move liquids with a viscosity in the range of $0.5*10^{-3}$ Pa*s to $75*10^{-3}$ Pa*s.

14. The device according to claim 1, wherein the device can be actuated manually and operates with no additional energy consumption.

15. The device according to claim 1, further comprising at least a further capillary pump, the device being adapted to activate the capillary pump and the at least a further capillary pump simultaneously, with exit in a same zone, when operational to mix their fluid.

16. The device according to claim 1, comprising at least a further capillary pump, the device being adapted to activate the capillary pump and the at least a further capillary pump sequentially with exit in a same zone, when operational to sequentially deliver their fluid to the same zone.

17. The device according to claim 1, comprising at least a further capillary pump, wherein the capillary pump is engaged to activate the at least a further capillary pump, or vice versa.

18. The device according to claim 1, wherein the fluid conduit comprises a conduit shunt physically or functionally connected with a port for sampling fluid for instance ambient or bodily fluid.

19. The device according to claim 1, wherein the fluid conduit comprises a conduit shunt physically or functionally connected with a reservoir for containing any one of the group consisting of a working fluid, an analyte, a ligand, a biological active molecule, a chemical reactive molecule and a physical reactive molecule.

20. The device according to claim 1, wherein the capillary pump comprises a solid sorbent being enclosed in an enclosure, wherein said enclosure of the solid sorbent comprises an opening connecting the enclosure to an outlet channel, wherein an analytical zone is in fluid connection to the outlet channel, the analytical zone being adapted for receiving an analyte, the analytical zone furthermore being provided with a detector unit for detecting properties of analyte in the analytical zone.

* * * * *